(12) United States Patent
Inoue et al.

(10) Patent No.: US 8,664,383 B2
(45) Date of Patent: Mar. 4, 2014

(54) ORGANOMETALLIC COMPLEX, AND LIGHT-EMITTING ELEMENT AND DISPLAY DEVICE USING THE ORGANOMETALLIC COMPLEX

(75) Inventors: Hideko Inoue, Kanagawa (JP); Nobuharu Ohsawa, Kanagawa (JP); Satoko Shitagaki, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 153 days.

(21) Appl. No.: 13/242,311

(22) Filed: Sep. 23, 2011

(65) Prior Publication Data

US 2012/0095226 A1    Apr. 19, 2012

(30) Foreign Application Priority Data

Oct. 15, 2010    (JP) ................. 2010-233014

(51) Int. Cl.
*C07F 15/00*    (2006.01)

(52) U.S. Cl.
USPC ....................................... 544/225

(58) Field of Classification Search
USPC ....................................... 544/225
See application file for complete search history.

(56) References Cited

U.S. PATENT DOCUMENTS

| | | | |
|---|---|---|---|
| 6,780,528 | B2 | 8/2004 | Tsuboyama et al. |
| 6,803,720 | B2 | 10/2004 | Kwong et al. |
| 6,821,646 | B2 | 11/2004 | Tsuboyama et al. |
| 6,953,628 | B2 | 10/2005 | Kamatani et al. |
| 7,094,477 | B2 | 8/2006 | Kamatani et al. |
| 7,147,935 | B2 | 12/2006 | Kamatani et al. |
| 7,220,495 | B2 | 5/2007 | Tsuboyama et al. |
| 7,589,203 | B2 | 9/2009 | Stossel et al. |
| 7,960,038 | B2 | 6/2011 | Ohsawa et al. |
| 7,993,494 | B2 | 8/2011 | Inoue et al. |
| 2002/0063516 | A1 | 5/2002 | Tsuboyama et al. |
| 2005/0221123 | A1 | 10/2005 | Inoue et al. |
| 2006/0127696 | A1 | 6/2006 | Stossel et al. |
| 2006/0228583 | A1 | 10/2006 | Kamatani et al. |
| 2006/0263636 | A1 | 11/2006 | Ohsawa et al. |
| 2007/0129545 | A1 | 6/2007 | Inoue et al. |
| 2007/0244320 | A1 | 10/2007 | Inoue et al. |
| 2008/0286604 | A1 | 11/2008 | Inoue et al. |
| 2008/0305361 | A1 | 12/2008 | Inoue et al. |
| 2008/0312437 | A1 | 12/2008 | Inoue et al. |
| 2009/0015143 | A1 | 1/2009 | Inoue et al. |
| 2009/0033209 | A1 | 2/2009 | Seo et al. |
| 2010/0105902 | A1 | 4/2010 | Inoue et al. |
| 2010/0145044 | A1 | 6/2010 | Inoue et al. |
| 2010/0181905 | A1 | 7/2010 | Inoue et al. |
| 2011/0082296 | A1 | 4/2011 | Inoue et al. |
| 2011/0245495 | A1 | 10/2011 | Inoue et al. |
| 2012/0104373 | A1 | 5/2012 | Inoue et al. |

FOREIGN PATENT DOCUMENTS

| | | |
|---|---|---|
| EP | 1 191 612 A2 | 3/2002 |
| JP | 2004-515895 | 5/2004 |
| JP | 2005-314414 | 11/2005 |
| JP | 2006-120762 | 5/2006 |
| JP | 2006-352102 | 12/2006 |
| JP | 2007-176917 | 7/2007 |
| WO | WO 02/47457 A2 | 6/2002 |

OTHER PUBLICATIONS

O'Brien, D.F. et al, "Improved Energy Transfer in Electrophosphorescent Devices," Applied Physics Letters, vol. 74, No. 3, Jan. 18, 1999, pp. 442-444.
Inoue, H. et al, "A Reaction of Singlet Oxygen with an Unsaturated Organic Molecule, 6.1.4, Quencher and Photosensitizer," *Basic Chemistry Course Photochemistry I*, Maruzen Co., Ltd., Sep. 30, 1999, pp. 106-110 (with English abstract).
Tsutsui, T. et al, "High Quantum Efficiency in Organic Light-Emitting Devices with Iridium-Complex as a Triplet Emissive Center," Japanese Journal of Applied Physics, vol. 38, part 2, No. 12B, Dec. 15, 1999, pp. L1502-L1504.
Baldo, M.A. et al, "High-Efficiency Fluorescent Organic Light-Emitting Devices Using a Phosphorescent Sensitizer," Nature, vol. 403, Feb. 17, 2000, pp. 750-753.
Thompson, M.E. et al, "Phosphorescent Materials and Devices," Proceedings of the 10th International Workshop on Inorganic and Organic Electroluminescence, EL '00, Dec. 4, 2000, pp. 35-38.
Duan, J.-P. et al, "New Iridium Complexes as Highly Efficient Orange-Red Emitters in Organic Light-Emitting Diodes," Advanced Materials, vol. 15, No. 3, Feb. 5, 2003, pp. 224-228.
Zhang, G-L et al, "Synthesis and Phosphorescence of a New Iridium(III) Pyrazine Complex," Wuli Huaxue Xuebao, Acta Physico-Chimica Sinica, vol. 19, No. 10, Oct. 19, 2003, pp. 889-891 (with English abstract).

(Continued)

*Primary Examiner* — Brian McDowell
(74) *Attorney, Agent, or Firm* — Husch Blackwell LLP

(57) ABSTRACT

Disclosed is an organometallic complex capable of variable phosphorescence characteristics and yellow emission at high luminance The organometallic complex has a structure represented by a formula (G6), where at least one of $R^4$, $R^5$, $R^6$, and $R^7$ is a phenoxy group, M is a Group 9 metal or a Group 10 metal, and L is a monoanionic ligand.

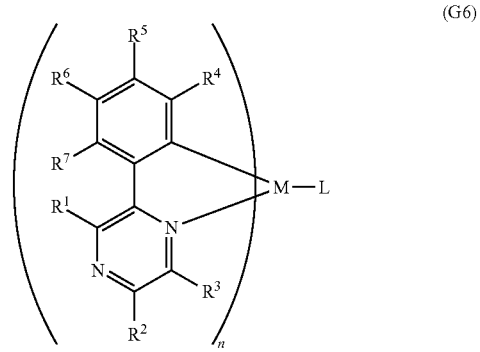

11 Claims, 17 Drawing Sheets

(56) References Cited

OTHER PUBLICATIONS

Slater, J.W. et al, "Cyclometallated Nitrogen Heterocycles," Journal of Organo Metallic Chemistry, vol. 688, Aug. 29, 2003, pp. 112-120.
Zhang, G-L et al, "Synthesis and Luminescence Property of a New Yellow Phosphorescent Iridium(III) Pyrazine Complex," Chemical Journal of Chinese Universities, vol. 25, No. 3, Mar. 1, 2004, pp. 397-400 (with English abstract).
Tao et al., Metal Complex Polymer for Second Harmonic Generation and Electroluminescence Applications, Appl. Phys. Lett., Mar. 24, 1997, vol. 70, No. 12, pp. 1503-1505.
Steel et al., Cyclometallated Compounds V. Double Cyclopalladation of Diphenyl Pyrazines and Related Ligands, Journal of Organometallic Chemistry, 1990, vol. 395, pp. 359-373.
Baldo et al., Very High-Efficiency Green Organic Light-Emitting Devices Based on Electrophosphorescenece, Applied Physics Letters, Jul. 5, 1999, vol. 75, No. 1, pp. 4-6.
Adachi et al., High-Efficiency Red Electrophosphorescence Devices, Applied Physics Letters, Mar. 12, 2001, vol. 78, No. 11, pp. 1622-1624.
Zhang et al., "Synthesis and Phosphorescence Property of a New Pyrazine Iridium (III) Complex", Wuli Huaxue Xuebao, Acta Physico-Chimica Sinica, Oct. 19, 2003, pp. 889-891 vol. 19 (No. 10) , (with English translation).
Zhang et al., "Synthesis and Luminescence Property of a New Yellow Phosphorescent Iridium (III) Pyrazine Complex, Chemical Journal of Chinese Universities", Mar. 1, 2004, pp. 397-400, vol. 25 (No. 3), (with English translation).

7100

7200

7300

7400

7500

ORGANOMETALLIC COMPLEX, AND LIGHT-EMITTING ELEMENT AND DISPLAY DEVICE USING THE ORGANOMETALLIC COMPLEX

BACKGROUND OF THE INVENTION

1. Field of the Invention

The present invention disclosed in this specification relates to an organometallic complex. In particular, the invention relates to an organometallic complex that can provide light emission from a triplet excited state. In addition, the invention relates to a light-emitting element and a light-emitting device each using the substance.

2. Description of the Related Art

In recent years, there have been the active research and product development of light-emitting elements in each of which an organic or inorganic compound having a light-emitting property is used as a light-emitting material. Especially light-emitting elements called EL (electroluminescence) elements have characteristics such as feasibility of being thinner and more lightweight and responsive to input signals, because the basic structure of such elements is a simple structure in which a layer containing a light-emitting material (a light-emitting layer) is just provided between a pair of electrodes (an anode and a cathode).

The light emission mechanism of an organic EL element is as follows: voltage application between a pair of electrodes causes electrons injected from the cathode and holes injected from the anode which serve as carriers to recombine in the light emission center of a light-emitting layer, a light-emitting substance is brought into an excited state, and energy is released when the molecular excitons return to the ground state; thus light is emitted. An organic EL element is also referred to as a carrier-injection element because of this mechanism.

A singlet excited state (S*) and a triplet excited state (T*) are known as types of the above excited state, and light emission can be obtained through either of the excited states. Note that, in a light-emitting element, the statistical generation ratio of the singlet excited state (S*) to the triplet excited state (T*) is considered to be 1:3.

It can be estimated in terms of the above generation ratio that, when the number of the injected carriers is 100%, about 25% of the light (photons) emitted by a light-emitting element is light emission from the singlet excited state (S*) and about 75% is light emission from the triplet excited state (T*).

Note that in this specification, light emission from the singlet excited state (S*) is referred to as "fluorescence" and a compound that emits fluorescence is referred to as a "fluorescent compound". Further, in this specification, light emission from the triplet excited state (T*) is referred to as "phosphorescence" and a compound that emits phosphorescence is referred to as a "phosphorescent compound".

Thus, use of a phosphorescent compound as well as a fluorescent compound for a light-emitting element enables the ratio of generated photons to injected carriers (hereinafter, referred to as internal quantum efficiency) to be increased to 75 to 100%. In other words, it is possible to realize three to four times as high emission efficiency as that of an element using only a fluorescent compound. For such a reason, light-emitting devices including light-emitting elements using phosphorescent compounds have been under active development in recent years so that highly-efficient light-emitting elements can be realized (e.g., see Non-Patent Document 1). As phosphorescent compounds, organometallic complexes that have iridium or the like as a central metal have particularly attracted attention because of their high phosphorescence quantum yield.

Further, a light-emitting element using a phosphorescent compound is disclosed which uses a light-emitting layer containing an organic low molecular hole-transport substance and an organic low molecular electron-transport substance as host substances and the phosphorescent compound as a dopant and has improved emission efficiency (see Patent Document 1).

The mainstream research have focused on application of light-emitting devices including such light-emitting elements having high emission efficiency to image display devices typified by organic EL displays.

At the same time, due to recent attention to the energy problems, power consumption is becoming a major factor controlling the trends in consumer purchases and application of light-emitting elements to lighting devices is also being actively examined.

In application of light-emitting elements to lighting devices, it is preferable to use color with high luminance (the luminance means the degree of brightness perceived by humans and is expressed as the proportion of the degree of the brightness of a perceivable wavelength on the assumption that the wavelength of light which is the most strongly perceived by human eyes (555 nm) is 1). One of such color with high luminance is yellow (Y).

Note that yellow (Y) has advantageous effects on image display devices as well, since addition of yellow to the three primary colors (red (R), green (G), and blue (B)) for image display devices creates features such as higher luminance and more brilliant display of dark yellow or bright green.

[References]

Patent Document 1: Japanese Translation of PCT International Application No. 2004-515895

Non-Patent Document 1: Zhang, Guo-Lin and five others, Gaodeng Xuexiao Huaxue Xuebao, 2004, vol. 25, No. 3, pp. 397-400.

SUMMARY OF THE INVENTION

Light-emitting substances capable of emitting light with high efficiency are expected to have a variety of uses. Furthermore, organometallic complexes which are highly-efficient light-emitting substances that emit phosphorescence are required to have adjustable light-emitting characteristics (e.g., emission color or emission efficiency) so as to suit a variety of uses.

Therefore, an object of one embodiment of the present invention is to provide an organometallic complex whose phosphorescence characteristics can be adjusted by varying the structure of a ligand.

Another object of one embodiment of the present invention is to provide a light-emitting element having high emission efficiency by varying the structure of a ligand.

Another object of one embodiment of the present invention is to provide an organometallic complex capable of emitting yellow phosphorescence with high luminance.

Another object of one embodiment of the present invention is to provide an organometallic complex capable of emitting phosphorescence for which the time and cost for the synthesis are saved.

Another object of one embodiment of the present invention is to provide a highly efficient light-emitting element using any of the above organometallic complexes.

Another object of one embodiment of the present invention is to provide a light-emitting device with high added value using the above light-emitting element.

The present invention aims to achieve at least one of the above-described objects.

Specifically, one embodiment of the present invention is an organometallic complex that has a structure represented by a general formula (G1) below and is formed in such a way that a phenylpyrazine derivative represented by a general formula (G0) below is ortho-metalated by an ion of a Group 9 metal or of a Group 10 metal.

[Chemical formula 1]

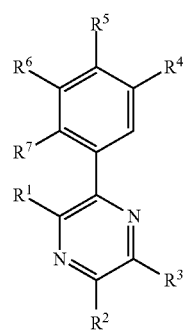

(G0)

[Chemical formula 2]

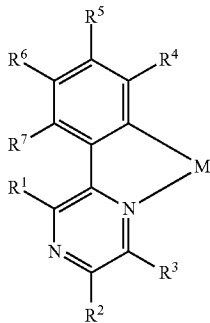

(G1)

In the above general formula (G1), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ and $R^3$ separately represent hydrogen or an alkyl group having 1 to 4 carbon atoms. Furthermore, at least one of substituent groups $R^4$, $R^5$, $R^6$, and $R^7$ includes a substituent group represented by a general formula (G2) below, and the other or others of the substituent groups represent any of hydrogen, an alkyl group having 1 to 4 carbon atoms, an alkoxy group having 1 to 4 carbon atoms, a halogen group, a trifluoromethyl group, and a phenyl group. Note that a phenyl group may be bonded to the alkyl group. In addition, M is a central metal and represents either a Group 9 element or a Group 10 element.

[Chemical formula 3]

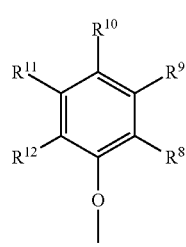

(G2)

In the above general formula (G2), $R^8$, $R^9$, $R^{10}$, $R^{11}$, and $R^{12}$ separately represent any of hydrogen, an alkyl group having 1 to 4 carbon atoms, an alkoxy group having 1 to 4 carbon atoms, a halogen group, a trifluoromethyl group, and a phenyl group. Note that a phenyl group may be bonded to the alkyl group.

Here, specific examples of the alkyl group having 1 to 4 carbon atoms for any of $R^1$ to $R^{12}$ are a methyl group, an ethyl group, a propyl group, an isopropyl group, a butyl group, a sec-butyl group, an isobutyl group, and a tert-butyl group. In addition, specific examples of the alkoxy group having 1 to 4 carbon atoms for any of $R^1$ and $R^4$ to $R^{12}$ are a methoxy group, an ethoxy group, a propoxy group, an isopropoxy group, a butoxy group, a sec-butoxy group, an isobutoxy group, and a tert-butoxy group. Further, specific examples of the alkoxycarbonyl group having 1 to 5 carbon atoms are a methoxycarbonyl group, an ethoxycarbonyl group, a propoxycarbonyl group, an isopropoxycarbonyl group, a butoxycarbonyl group, a sec-butoxycarbonyl group, an isobutoxycarbonyl group, and a tert-butoxycarbonyl group. In addition, examples of the halogen group for any of $R^4$ to $R^{12}$ are a fluoro group, a chloro group, a bromo group, and an iodine group, and especially a fluoro group is preferred.

With the organometallic complexes having a structure represented by the above general formula (G1), phosphorescence characteristics can be adjusted by varying the structure of the ligand.

Further, one embodiment of the present invention is an organometallic complex having a structure represented by the following general formula (G3).

[Chemical formula 4]

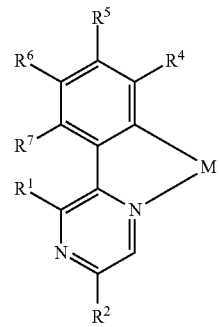

(G3)

In the above general formula (G3), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ represents hydrogen or an alkyl group having 1 to 4 carbon atoms. Furthermore, at least one of the substituent groups $R^4$, $R^5$, $R^6$, and $R^7$ has a structure represented by the general formula (G2) below, and the other or others of the substituent groups separately represent any of hydrogen, an alkyl group having 1 to 4 carbon atoms, an alkoxy group having 1 to 4 carbon atoms, a halogen group, a trifluoromethyl group, and a phenyl group. Note that a phenyl group may be bonded to the alkyl group. In addition, M is a central metal and represents either a Group 9 element or a Group 10 element.

[Chemical formula 5]

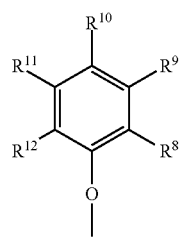

(G2)

In the above general formula (G2), $R^8$, $R^9$, $R^{10}$, $R^{11}$, and $R^{12}$ separately represent any of hydrogen, an alkyl group having 1 to 4 carbon atoms, an alkoxy group having 1 to 4 carbon atoms, a halogen group, a trifluoromethyl group, and a phenyl group. Note that a phenyl group may be bonded to the alkyl group.

In the organometallic complex represented by the general formula (G3), the substituent group $R^3$ in the general formula (G1) is hydrogen, so that steric hindrance of the pyrazine derivative can be reduced; thus, the effect of enhancing the synthesis yield of the organometallic complex can be obtained.

Further, one embodiment of the present invention is an organometallic complex having a structure represented by the following general formula (G4).

[Chemical formula 6]

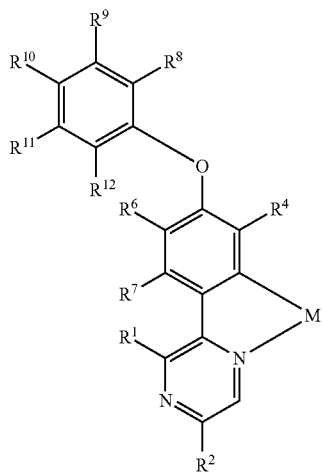

(G4)

In the above general formula (G4), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ represents hydrogen or an alkyl group having 1 to 4 carbon atoms. Furthermore, $R^4$, $R^6$, and $R^7$ separately represent any of hydrogen, an alkyl group having 1 to 4 carbon atoms, an alkoxy group having 1 to 4 carbon atoms, a halogen group, a trifluoromethyl group, and a phenyl group. Further, $R^8$, $R^9$, $R^{10}$, $R^{11}$, and $R^{12}$ separately represent any of hydrogen, an alkyl group having 1 to 4 carbon atoms, an alkoxy group having 1 to 4 carbon atoms, a halogen group, a trifluoromethyl group, and a phenyl group. Note that a phenyl group may be bonded to the alkyl group. In addition, M is a central metal and represents either a Group 9 element or a Group 10 element.

In the organometallic complex represented by the general formula (G4), the substituent group $R^3$ in the general formula (G1) is hydrogen and the substituent group $R^5$ is the substituent group represented by the general formula (G2), so that yellow phosphorescence with high luminosity can be emitted.

Further, one embodiment of the present invention is an organometallic complex having a structure represented by the following general formula (G5).

[Chemical formula 7]

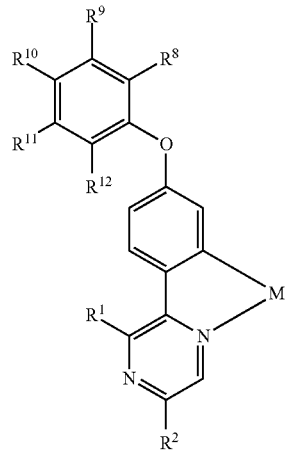

(G5)

In the above general formula (G5), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ represents hydrogen or an alkyl group having 1 to 4 carbon atoms. Further, $R^8$, $R^9$, $R^{10}$, $R^{11}$, and $R^{12}$ separately represent any of hydrogen, an alkyl group having 1 to 4 carbon atoms, an alkoxy group having 1 to 4 carbon atoms, a halogen group, a trifluoromethyl group, and a phenyl group. Note that a phenyl group may be bonded to the alkyl group. In addition, M is a central metal and represents either a Group 9 element or a Group 10 element.

The organometallic complex represented by the above general formula (G5) is easy to synthesize and thus preferable.

Further, one embodiment of the present invention is an organometallic complex represented by the following general formula (G6).

[Chemical formula 8]

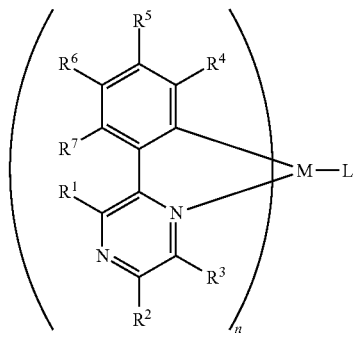

(G6)

In the above general formula (G6), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ and $R^3$ separately represent hydrogen or an alkyl group having 1 to 4 carbon atoms. Furthermore, at least one of substituent groups $R^4$, $R^5$, $R^6$, and $R^7$ has the substituent group represented by the general formula (G2) below, and the other or others of the substituent groups represent any of hydrogen, an alkyl group having 1 to 4 carbon atoms, an alkoxy group having 1 to 4 carbon atoms, a halogen group, a trifluoromethyl group, and a phenyl group. Note that a phenyl group may be bonded to the alkyl group. In addition, M is a central metal and represents either a Group 9 element or a Group 10 element. Further, L represents a monoanionic ligand. In addition, n is 2 when the central metal M is a Group 9 element, or n is 1 when the central metal M is a Group 10 element.

[Chemical formula 9]

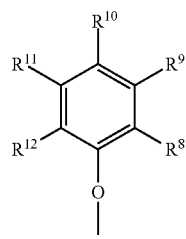

(G2)

In the above general formula (G2), $R^8$, $R^9$, $R^{10}$, $R^{11}$, and $R^{12}$ separately represent any of hydrogen, an alkyl group having 1 to 4 carbon atoms, an alkoxy group having 1 to 4 carbon atoms, a halogen group, a trifluoromethyl group, and a phenyl group. Note that a phenyl group may be bonded to the alkyl group.

The organometallic complex represented by the above general formula (G6) is easy to synthesize and thus preferable.

Further, one embodiment of the present invention is an organometallic complex represented by the following general formula (G7).

[Chemical formula 10]

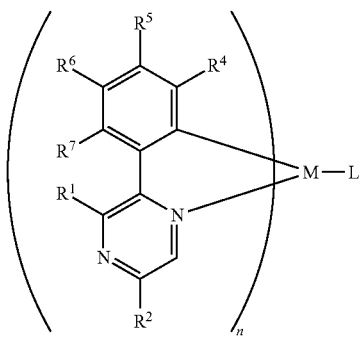

(G7)

In the above general formula (G7), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ represents hydrogen or an alkyl group having 1 to 4 carbon atoms. Furthermore, at least one of the substituent groups $R^4$, $R^5$, $R^6$, and $R^7$ has a structure represented by the general formula (G2) below, and the other or others of the substituent groups separately represent any of hydrogen, an alkyl group having 1 to 4 carbon atoms, an alkoxy group having 1 to 4 carbon atoms, a halogen group, a trifluoromethyl group, and a phenyl group. Note that a phenyl group may be bonded to the alkyl group. In addition, M is a central metal and represents either a Group 9 element or a Group 10 element. Further, L represents a monoanionic ligand. In addition, n is 2 when the central metal M is a Group 9 element, or n is 1 when the central metal M is a Group 10 element.

[Chemical formula 11]

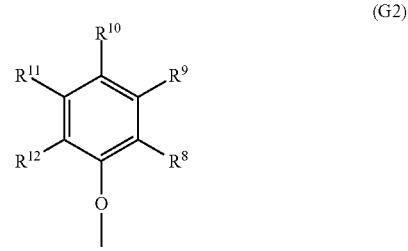

(G2)

In the above general formula (G2), $R^8$, $R^9$, $R^{10}$, $R^{11}$, and $R^{12}$ separately represent any of hydrogen, an alkyl group having 1 to 4 carbon atoms, an alkoxy group having 1 to 4 carbon atoms, a halogen group, a trifluoromethyl group, and a phenyl group. Note that a phenyl group may be bonded to the alkyl group.

The organometallic complex represented by the above general formula (G7) is easy to synthesize and thus preferable.

Further, one embodiment of the present invention is an organometallic complex represented by the following general formula (G8).

[Chemical formula 12]

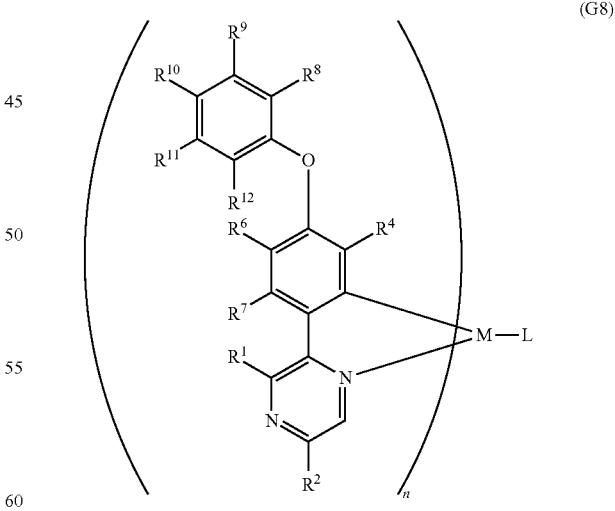

(G8)

In the above general formula (G8), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ represents hydrogen or an alkyl group having 1 to 4 carbon atoms. Furthermore, $R^4$, $R^6$, and $R^7$ separately represent any of hydrogen, an alkyl group having 1 to 4 carbon atoms, an alkoxy group having 1 to 4 carbon atoms, a halogen group, a trifluoromethyl group, and a phenyl group. Further, $R^8$, $R^9$, $R^{10}$, $R^{11}$, and $R^{12}$ separately represent any of hydrogen, an alkyl group having 1 to 4 carbon atoms, an alkoxy group having 1 to 4 carbon atoms, a halogen group, a trifluoromethyl group, and a phenyl group. Note that a phenyl group may be bonded to the alkyl group. In addition, M is a central metal and represents either a Group 9 element or a Group 10 element. Further, L represents a monoanionic ligand. In addition, n is 2 when the central metal M is a Group 9 element, or n is 1 when the central metal M is a Group 10 element.

The organometallic complex represented by the above general formula (G8) is easy to synthesize and thus preferable.

Further, one embodiment of the present invention is an organometallic complex represented by the following general formula (G9).

[Chemical formula 13]

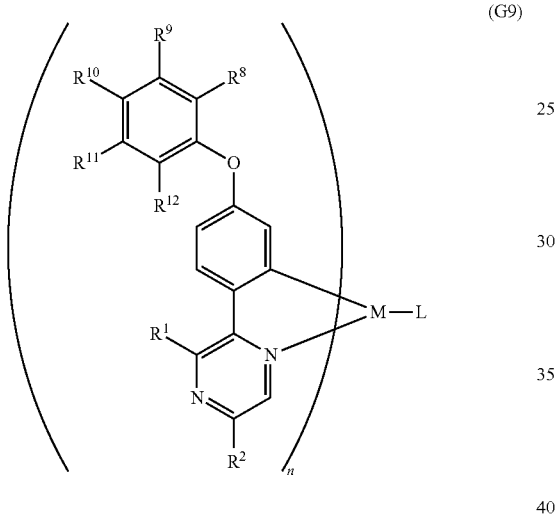

(G9)

In the above general formula (G9), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ represents hydrogen or an alkyl group having 1 to 4 carbon atoms. Further, $R^8$, $R^9$, $R^{10}$, $R^{11}$, and $R^{12}$ separately represent any of hydrogen, an alkyl group having 1 to 4 carbon atoms, an alkoxy group having 1 to 4 carbon atoms, a halogen group, a trifluoromethyl group, and a phenyl group. Note that a phenyl group may be bonded to the alkyl group. In addition, M is a central metal and represents either a Group 9 element or a Group 10 element. Further, L represents a monoanionic ligand. In addition, n is 2 when the central metal M is a Group 9 element, or n is 1 when the central metal M is a Group 10 element.

The organometallic complex represented by the above general formula (G9) is easy to synthesize and thus preferable.

Another embodiment of the present invention is an organometallic complex in which the monoanionic ligand (L) in any of the general formulae (G6) to (G9) is any of a monoanionic bidentate chelate ligand having a β-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen. More preferably, the monoanionic ligand (L) is a monoanionic ligand represented by any of the following structural formulae (L1) to (L8).

[Chemical formulae 14]

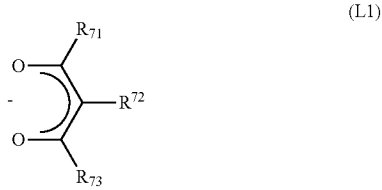

(L1)

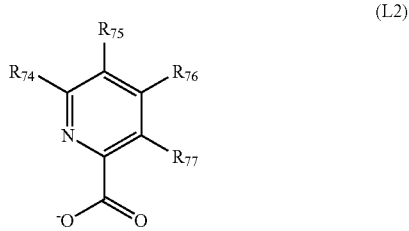

(L2)

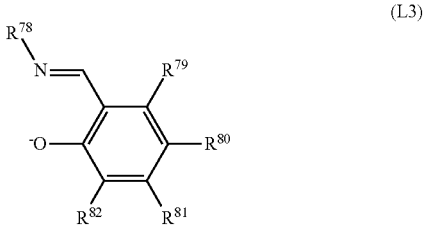

(L3)

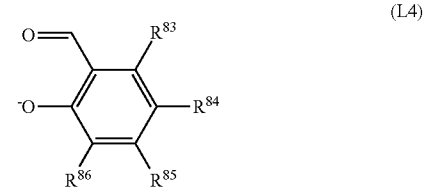

(L4)

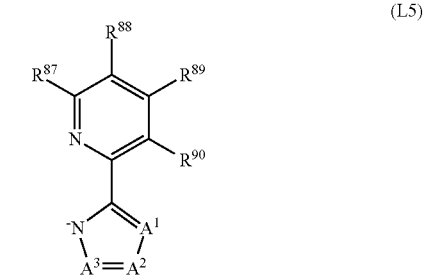

(L5)

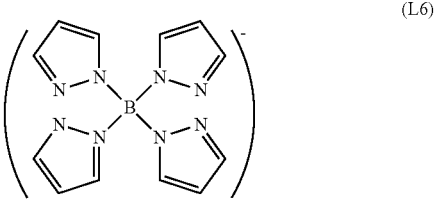

(L6)

In the above structural formulae (L1) to (L6), $R^{71}$ to $R^{90}$ separately represent any of hydrogen, an alkyl group having 1 to 4 carbon atoms, a halogen group, a haloalkyl group, an alkoxy group having 1 to 4 carbon atoms, and an alkylthio group having 1 to 4 carbon atoms. In addition, $A^1$, $A^2$, and $A^3$ separately represent nitrogen N or carbon C—R, and R represents hydrogen, an alkyl group having 1 to 4 carbon atoms, a halogen group, a haloalkyl group having 1 to 4 carbon atoms, or a phenyl group.

The monoanionic ligands represented by the above structural formulae (L1) to (L6) have high coordination ability and are inexpensively available, and the time and cost for the synthesis can be saved accordingly.

Further, one embodiment of the present invention is an organometallic complex represented by the following general formula (G10).

[Chemical formula 15]

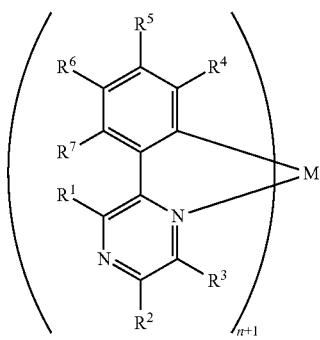

(G10)

In the above general formula (G10), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ and $R^3$ separately represent hydrogen or an alkyl group having 1 to 4 carbon atoms. Furthermore, at least one of the substituent groups $R^4$, $R^5$, $R^6$, and $R^7$ has a structure represented by the general formula (G2) below, and the other or others of the substituent groups separately represent any of hydrogen, an alkyl group having 1 to 4 carbon atoms, an alkoxy group having 1 to 4 carbon atoms, a halogen group, a trifluoromethyl group, and a phenyl group. Note that a phenyl group may be bonded to the allyl group. In addition, M is a central metal and represents either a Group 9 element or a Group 10 element. In addition, n is 2 when the central metal M is a Group 9 element, or n is 1 when the central metal M is a Group 10 element.

[Chemical formula 16]

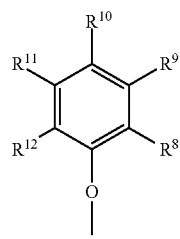

(G2)

In the above general formula (G2), $R^8$, $R^9$, $R^{10}$, $R^{11}$, and $R^{12}$ separately represent any of hydrogen, an alkyl group having 1 to 4 carbon atoms, an alkoxy group having 1 to 4 carbon atoms, a halogen group, a trifluoromethyl group, and a phenyl group. Note that a phenyl group may be bonded to the alkyl group.

The organometallic complex represented by the above general formula (G10) is easy to synthesize and thus preferable.

Further, one embodiment of the present invention is an organometallic complex represented by the following general formula (G11).

[Chemical formula 17]

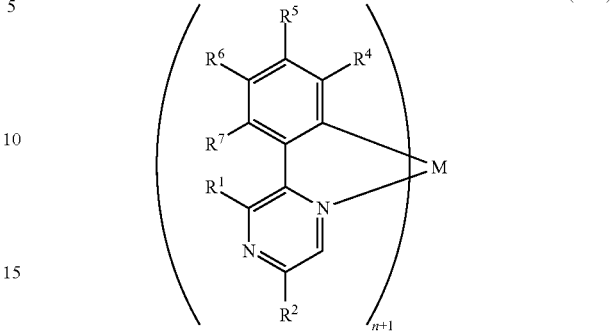

(G11)

In the above general formula (G11), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ represents hydrogen or an alkyl group having 1 to 4 carbon atoms. Furthermore, at least one of the substituent groups the functional substituent groups, $R^4$, $R^5$, $R^6$, and $R^7$ has a structure represented by the general formula (G2) below, and the other or others of the substituent groups have any of hydrogen, an alkyl group having 1 to 4 carbon atoms, an alkoxy group having 1 to 4 carbon atoms, a halogen group, a trifluoromethyl group, and a phenyl group. Note that a phenyl group may be bonded to the alkyl group. In addition, M is a central metal and represents either a Group 9 element or a Group 10 element. In addition, n is 2 when the central metal M is a Group 9 element, or n is 1 when the central metal M is a Group 10 element.

[Chemical formula 18]

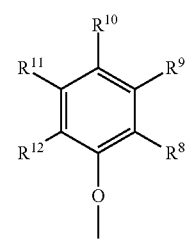

(G2)

In the above general formula (G2), $R^8$, $R^9$, $R^{10}$, $R^{11}$, and $R^{12}$ separately represent any of hydrogen, an alkyl group having 1 to 4 carbon atoms, an alkoxy group having 1 to 4 carbon atoms, a halogen group, a trifluoromethyl group, and a phenyl group. Note that an alkyl group may be substituted to the phenyl group.

The organometallic complex represented by the above general formula (G11) is easy to synthesize and thus preferable.

Further, one embodiment of the present invention is an organometallic complex represented by the following general formula (G12).

[Chemical formula 19]

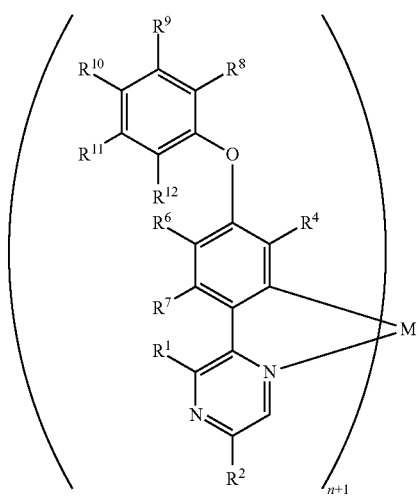

(G12)

In the above general formula (G12), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ represents hydrogen or an alkyl group having 1 to 4 carbon atoms. Furthermore, $R^4$, $R^6$, and $R^7$ separately represent any of hydrogen, an alkyl group having 1 to 4 carbon atoms, an alkoxy group having 1 to 4 carbon atoms, a halogen group, a trifluoromethyl group, and a phenyl group. Further, $R^8$, $R^9$, $R^{10}$, $R^{11}$, and $R^{12}$ separately represent any of hydrogen, an alkyl group having 1 to 4 carbon atoms, an alkoxy group having 1 to 4 carbon atoms, a halogen group, a trifluoromethyl group, and a phenyl group. Note that a phenyl group may be bonded to the alkyl group. In addition, M is a central metal and represents either a Group 9 element or a Group 10 element. In addition, n is 2 when the central metal M is a Group 9 element, or n is 1 when the central metal M is a Group 10 element.

The organometallic complex represented by the above general formula (G12) is easy to synthesize and thus preferable.

Further, one embodiment of the present invention is an organometallic complex represented by the following general formula (G13).

[Chemical formula 20]

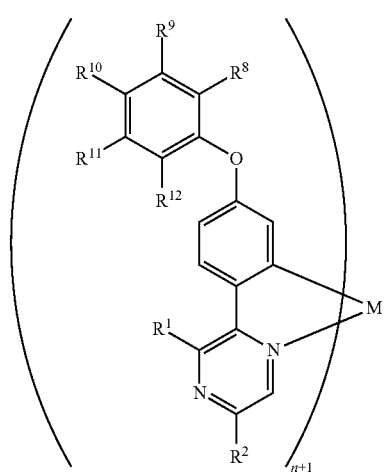

(G13)

In the above general formula (G13), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ represents hydrogen or an alkyl group having 1 to 4 carbon atoms. Further, $R^8$, $R^9$, $R^{10}$, $R^{11}$, and $R^{12}$ separately represent any of hydrogen, an alkyl group having 1 to 4 carbon atoms, an alkoxy group having 1 to 4 carbon atoms, a halogen group, a trifluoromethyl group, and a phenyl group. Note that a phenyl group may be bonded to the alkyl group. In addition, M is a central metal and represents either a Group 9 element or a Group 10 element. In addition, n is 2 when the central metal M is a Group 9 element, or n is 1 when the central metal M is a Group 10 element.

The organometallic complex represented by the above general formula (G13) is easy to synthesize and thus preferable.

Another embodiment of the present invention is an organometallic complex in which the central metal M, in any of the above organometallic complexes according to embodiments of the present invention, is iridium or platinum.

Owing to the presence of a heavy atom such as iridium or platinum in the organometallic complex, a spin flip due to the heavy atom effect easily occurs. This increases the probability that an electron at the excited singlet level will be transferred by intersystem crossing to the excited triplet level, so that the above organometallic complex can emit phosphorescence efficiently, which is preferable.

Another embodiment of the present invention is a light-emitting element including any of the above organometallic complexes as a light-emitting substance.

By including any of the organometallic complexes as the light-emitting substance for a light-emitting element, a light-emitting element capable of efficient phosphorescence can be provided. Further, with use of any of the organometallic complexes that emit yellow phosphorescence with high luminosity, a light-emitting element showing excellent visibility can be provided.

Another embodiment of the present invention is a light-emitting device including the above light-emitting element.

By including the above light-emitting element, a light-emitting device having low power consumption can be provided. Further, a light-emitting device in which any of the organometallic complexes that emit yellow phosphorescence with high luminosity is used has high added value with characteristics such as high luminance, capability of brilliantly displaying dark yellow or bright green, and excellent visibility.

Note that the term "light-emitting device" in this specification covers an electronic device including a light-emitting element and a lighting device including a light-emitting element, and therefore refers to an image display device, a light-emitting device, or a light source (including a lighting device). In addition, the light-emitting device includes all the following modules: a module in which a connector, such as a flexible printed circuit (FPC), a tape automated bonding (TAB) tape, or a tape carrier package (TCP), is attached to a light-emitting device, a module in which a printed wiring board is provided at the end of a TAB tape or a TCP, and a module in which an integrated circuit (IC) is directly mounted on a light-emitting device by a chip-on-glass (COG) method.

In this specification, an EL layer refers to a layer provided between a pair of electrodes in a light-emitting element. Thus, a light-emitting layer containing an organic compound that is a light-emitting substance which is interposed between electrodes is one mode of the EL layer.

In this specification, when Substance A is dispersed in a matrix formed of Substance B, Substance B forming the matrix is called a host material and Substance A dispersed in the matrix is called a guest material. Note that Substance A and Substance B may be separately a single substance or a mixture of two or more kinds of substances.

Further, the expression "A and B are connected to each other" in this specification refers to the case where A and B are electrically connected to each other (i.e., A and B are connected to each other with another element or another circuit interposed therebetween), where A and B are functionally connected to each other (i.e., A and B are functionally connected to each other with another circuit interposed therebetween), or where A and B are directly connected to each other (i.e., A and B are connected to each other without any other element or circuit interposed therebetween).

According to the present invention, an organometallic complex whose phosphorescence characteristics can be adjusted by varying the structure of a ligand can be provided.

Alternatively, a light-emitting element having high emission efficiency by varying the structure of a ligand can be provided.

Alternatively, an organometallic complex capable of emitting yellow phosphorescence with high luminosity can be provided.

Alternatively, an organometallic complex capable of emitting phosphorescence for which the time and cost for the synthesis are saved can be provided.

Alternatively, a highly efficient light-emitting element using any of the above organometallic complexes can be provided.

Alternatively, a light-emitting device with high added value using the above light-emitting element can be provided.

DETAILED DESCRIPTION OF THE INVENTION

Figure 1:
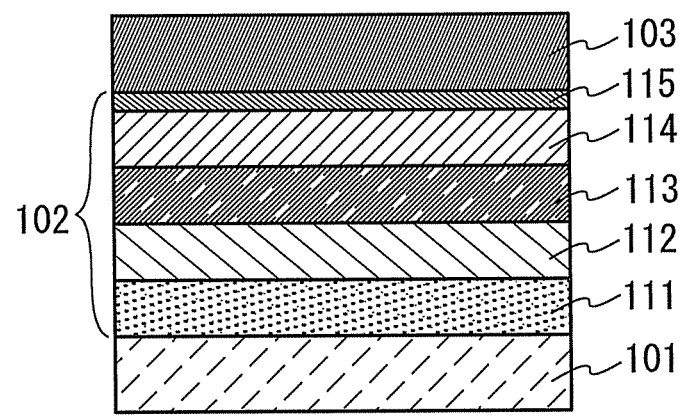
FIG. 1 illustrates a light-emitting element which is one embodiment of the present invention.

Embodiments will be described in detail with reference to the drawings. Note that the invention is not limited to the description given below, and it will be easily understood by those skilled in the art that various changes and modifications can be made without departing from the spirit and scope of the invention. Therefore, the invention should not be construed as being limited to the description in the following embodiments. Note that in the structures of the invention described below, the same portions or portions having similar functions are denoted by the same reference numerals in different drawings, and description of such portions is not repeated.

(Embodiment 1)

In Embodiment 1, organometallic complexes which are embodiments of the present invention will be described.

[Synthesis Method of Phenylpyrazine Derivative Represented by the General Formula (G0) and Specific Preferred Examples of Organometallic Complex Having Phenylpyrazine Derivative Represented by the General Formula (G0)]

A phenylpyrazine derivative represented by the general formula (G0) below can be synthesized by a simple synthesis scheme as follows. For example, as illustrated in a scheme (a) below, phenylboronic acid (A1) is coupled with a halogenated pyrazine compound (A2), so that the phenylpyrazine derivative can be obtained. Alternatively, as illustrated in a scheme (a') below, aryl diketone (A1') is reacted with diamine (A2'), so that the phenylpyrazine derivative can be obtained. Note that in the general formula (G0) below, $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ and $R^3$ separately represent hydrogen or an alkyl group having 1 to 4 carbon atoms. Furthermore, $R^4$, $R^5$, $R^6$, and $R^7$ separately represent any of hydrogen, an alkyl group having 1 to 4 carbon atoms, an alkoxy group having 1 to 4 carbon atoms, a halogen group, a trifluoromethyl group, and a phenyl group. Note that a phenyl group may be bonded to the alkyl group. Further, X in the following scheme (a) represents a halogen element.

[Chemical formula 21]

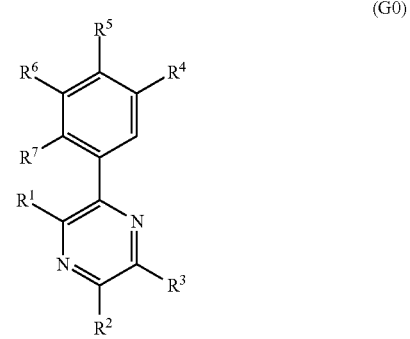

-continued

[Chemical formulae 22]

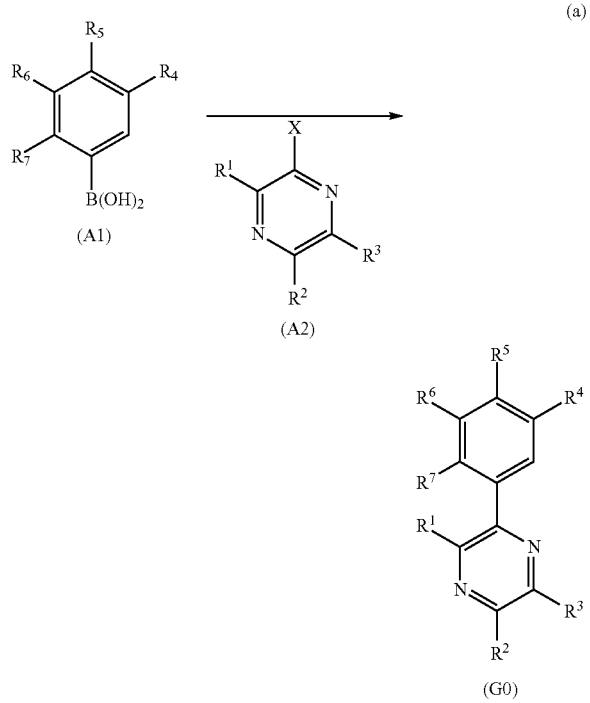

[Chemical formulae 23]

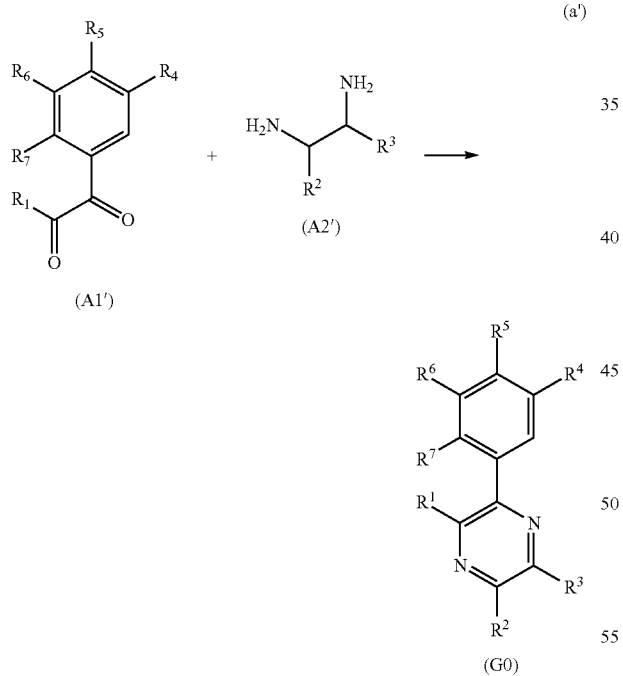

One embodiment of the present invention is an organometallic complex which has the structure represented by the general formula (G1) below and has a bulky structure (or a high volume structure) formed in such a way that the phenylpyrazine derivative, which is prepared by the above synthesis method and represented by the general formula (G0), is ortho-metalated by an ion of a Group 9 metal or of a Group 10 metal. The organometallic complex having the structure represented by the general formula (G1) below has high heat resistance due to the bulky structure, and phosphorescence characteristics which can be adjusted by varying the structure of a ligand. Thus, the light-emitting characteristics can be fine-tuned according to the required characteristics of a display device, providing applicability to a variety of display devices.

[Chemical formula 24]

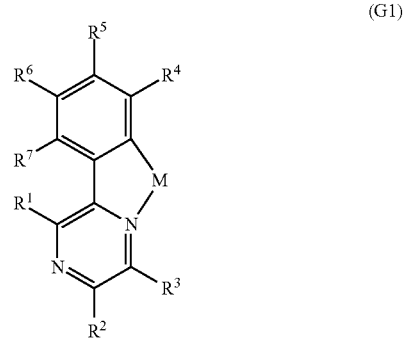

In the above general formula (G1), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ and $R^3$ separately represent hydrogen or an alkyl group having 1 to 4 carbon atoms. Furthermore, at least one of substituent groups $R^4$, $R^5$, $R^6$, and $R^7$ includes a substituent group represented by a general formula (G2) below, and the other or others of the substituent groups represent any of hydrogen, an alkyl group having 1 to 4 carbon atoms, an alkoxy group having 1 to 4 carbon atoms, a halogen group, a trifluoromethyl group, and a phenyl group. Note that a phenyl group may be bonded to the alkyl group. In addition, M is a central metal and represents either a Group 9 element or a Group 10 element.

[Chemical formula 25]

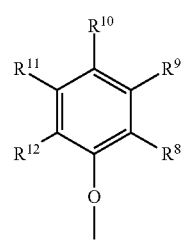

Since a wide variety of substances as the compounds (A1), (A2), (A1'), and (A2') in the scheme (a) and the scheme (a') are commercially available or can be synthesized, a great variety of substances as the phenylpyrazine derivative represented by the general formula (G0) can be synthesized. Consequently, the organometallic complex, which has a structure represented by the general formula (G1) and is formed in such a way that the general formula (G0) is ortho-metalated by an ion of a Group 9 metal or of a Group 10 metal, also shows variations with a wide variety of ligands.

One embodiment of the present invention is an organometallic complex having the structure represented by the general formula (G3) below, which is among the variations with a wide variety of ligands. The general formula (G3) below is a structure in which the substituent group $R^3$ in the general formula (G1) is hydrogen and by which the steric hindrance of the pyrazine derivative can be reduced. The synthesis yield of the organometallic complex can therefore be enhanced; accordingly, the price of the synthesized organometallic complex can be reduced.

[Chemical formula 26]

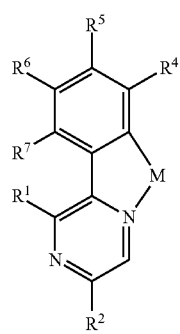

(G3)

In the above general formula (G3), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ represents hydrogen or an alkyl group having 1 to 4 carbon atoms. Furthermore, at least one of the substituent groups $R^4$, $R^5$, $R^6$, and $R^7$ has the structure represented by the general formula (G2), and the other or others of the substituent groups separately represent any of hydrogen, an alkyl group having 1 to 4 carbon atoms, an alkoxy group having 1 to 4 carbon atoms, a halogen group, a trifluoromethyl group, and a phenyl group. Note that a phenyl group may be bonded to the alkyl group. In addition, M is a central metal and represents either a Group 9 element or a Group 10 element.

One embodiment of the present invention is an organometallic complex having a structure represented by the general formula (G4) below. The general formula (G4) below is a structure in which the substituent group $R^3$ in the general formula (G1) is hydrogen and the substituent group $R^5$ is the substituent group represented by the general formula (G2) and which can emit yellow phosphorescence with high luminosity. Accordingly, a light-emitting device having high added value can be fabricated by using the organometallic complex represented by the following general formula (G4).

[Chemical formula 27]

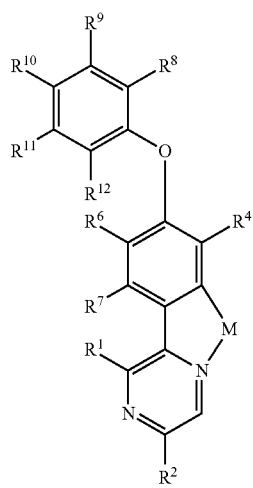

(G4)

In the above general formula (G4), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ represents hydrogen or an alkyl group having 1 to 4 carbon atoms. Furthermore, $R^4$, $R^6$, and $R^7$ separately represent any of hydrogen, an alkyl group having 1 to 4 carbon atoms, an alkoxy group having 1 to 4 carbon atoms, a halogen group, a trifluoromethyl group, and a phenyl group. Further, $R^8$, $R^9$, $R^{10}$, $R^{11}$, and $R^{12}$ separately represent any of hydrogen, an alkyl group having 1 to 4 carbon atoms, an alkoxy group having 1 to 4 carbon atoms, a halogen group, a trifluoromethyl group, and a phenyl group. Note that a phenyl group may be bonded to the alkyl group. In addition, M is a central metal and represents either a Group 9 element or a Group 10 element.

Further, one embodiment of the present invention is an organometallic complex having a structure represented by the general formula (G5) below. The general formula (G5) below is a structure in which the substituent groups $R^3$, $R^4$, $R^6$, and $R^7$ in the general formula (G1) are hydrogen and the substituent group $R^5$ is the substituent group represented by the general formula (G2) and which facilitates synthesis, and the time and cost for the synthesis can be saved accordingly.

[Chemical formula 28]

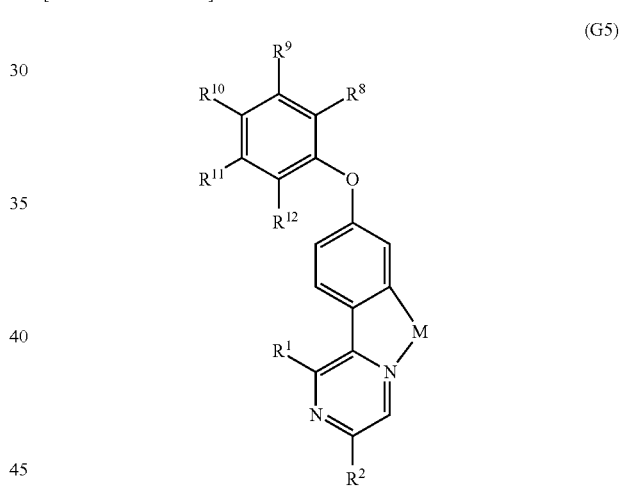

(G5)

In the above general formula (G5), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ represents hydrogen or an alkyl group having 1 to 4 carbon atoms. Further, $R^8$, $R^9$, $R^{10}$, $R^{11}$, and $R^{12}$ separately represent any of hydrogen, an alkyl group having 1 to 4 carbon atoms, an alkoxy group having 1 to 4 carbon atoms, a halogen group, a trifluoromethyl group, and a phenyl group. Note that a phenyl group may be bonded to the alkyl group. In addition, M is a central metal and represents either a Group 9 element or a Group 10 element.

[Synthesis Method of Organometallic Complex Represented by General Formula (G6) And Specific Preferred Examples of Organometallic Complex Having Structure Represented by General Formula (G6)]

Next, a method of synthesizing the organometallic complex represented by the general formula (G6) below, which is a specific preferred example of the organometallic complex having the structure represented by the general formula (G1), will be described.

[Chemical formula 29]

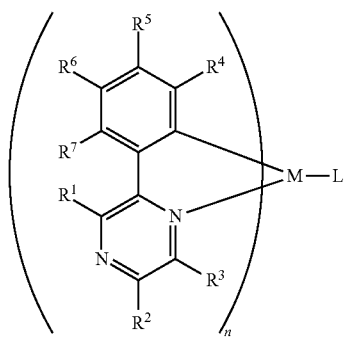

(G1)

First, as illustrated in a synthesis scheme (b) below, the phenylpyrazine derivative represented by the general formula (G0) and a compound of a Group 9 metal or a Group 10 metal which contains a halogen (e.g., a metal halide or a metal complex) are heated with an alcohol-based solvent (e.g., glycerol, ethylene glycol, 2-methoxyethanol, or 2-ethoxyethanol) alone or a mixed solvent of water and one or more kinds of such alcohol-based solvents, so that a binuclear complex (B) can be obtained, which is a kind of organometallic complex including the structure represented by the general formula (G1). There is no particular limitation on a heating means, and an oil bath, a sand bath, or an aluminum block may be used. Further, heating with microwaves can be used.

Examples of the compounds of Group 9 or Group 10 metal which contains halogen include, but not limited to, rhodium chloride hydrate, palladium chloride, iridium chloride hydrate, iridium chloride hydrochloride hydrate, potassium tetrachloroplatinate(II), and the like. Note that in the synthesis scheme (b) below, M is a central metal and represents either a Group 9 element or a Group 10 element, and X represents a halogen element. In addition, n is 2 when the central metal M is a Group 9 element, or n is 1 when the central metal M is a Group 10 element.

[Chemical formulae 30]

(b)

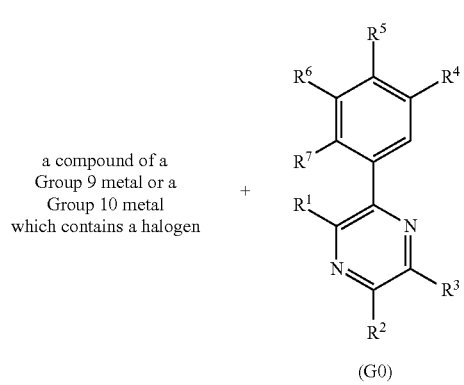

(G0)

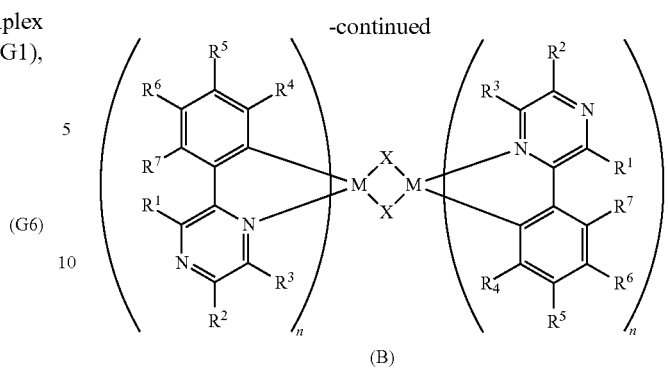

(B)

Furthermore, as illustrated in a synthesis scheme (c) below, the binuclear complex (B) obtained by the above synthesis scheme (b) is reacted with HL which is a material of a monoanionic ligand, so that a proton of HL is eliminated and the monoanionic ligand is ortho-metalated by the central metal M; thus, the organometallic complex represented by the general formula (G6) which is one embodiment of the present invention can be obtained. There is no particular limitation on a heating means, and an oil bath, a sand bath, or an aluminum block may be used. Further, heating with microwaves can be used. Note that in the synthesis scheme (c), the central metal M represents either a Group 9 element or a Group 10 element, and X represents a halogen element. In addition, n is 2 when the central metal M is a Group 9 element, or n is 1 when the central metal M is a Group 10 element.

[Chemical formulae 31]

(c)

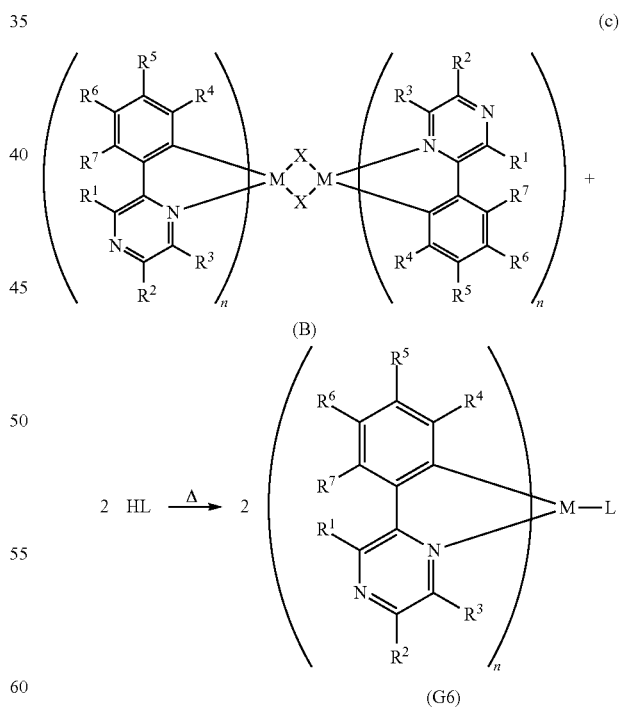

The organometallic complex represented by the general formula (G6) below, which can be synthesized according to the scheme (b) and the scheme (c) as described above, is one embodiment of the present invention. The general formula (G6) below is a specific example of the organometallic complex having the structure of the general formula (G1), and is easy to synthesize and therefore preferable.

[Chemical formula 32]

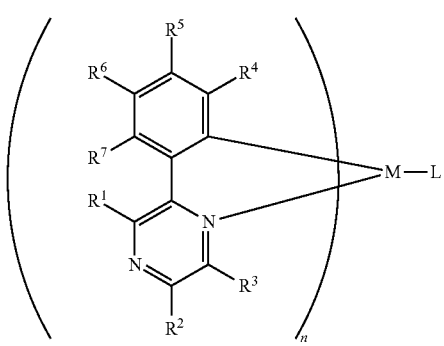

(G6)

In the above general formula (G6), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ and $R^3$ separately represent hydrogen or an alkyl group having 1 to 4 carbon atoms. Furthermore, at least one of the substituent groups $R^4$, $R^5$, $R^6$, and $R^7$ has the substituent group represented by the general formula (G2), and the other or others of the substituent groups represent any of hydrogen, an alkyl group having 1 to 4 carbon atoms, an alkoxy group having 1 to 4 carbon atoms, a halogen group, a trifluoromethyl group, and a phenyl group. Note that a phenyl group may be bonded to the alkyl group. In addition, M is a central metal and represents either a Group 9 element or a Group 10 element. Further, L represents a monoanionic ligand. In addition, n is 2 when the central metal M is a Group 9 element, or n is 1 when the central metal M is a Group 10 element.

Note that the general formula (G6) also shows variations with a wide variety of ligands, since the organometallic complex, which has the structure represented by the general formula (G1) and is formed in such a way that the general formula (G0) is ortho-metalated by an ion of a Group 9 metal or of a Group 10 metal, shows variations with a wider variety of ligands due to the variations of the compounds (A1), (A2), (A1'), and (A2') used in the scheme (a) and the scheme (a'), as described above.

One embodiment of the present invention is an organometallic complex having a structure represented by the general formula (G7) below, which is among the variations with a wide variety of ligands. The general formula (G7) below is a specific example of the organometallic complex having the structure of the general formula (G3), and is easy to synthesize and therefore preferable.

[Chemical formula 33]

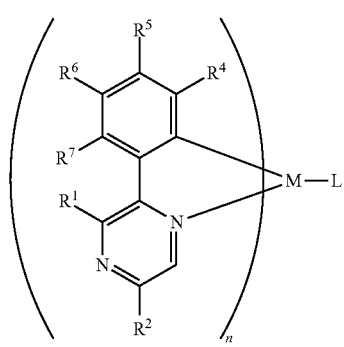

(G7)

In the above general formula (G7), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ represents hydrogen or an alkyl group having 1 to 4 carbon atoms. Furthermore, at least one of the substituent groups $R^4$, $R^5$, $R^6$, and $R^7$ has the structure represented by the general formula (G2), and the other or others of the substituent groups separately represent any of hydrogen, an alkyl group having 1 to 4 carbon atoms, an alkoxy group having 1 to 4 carbon atoms, a halogen group, a trifluoromethyl group, and a phenyl group. Note that a phenyl group may be bonded to the alkyl group. In addition, M is a central metal and represents either a Group 9 element or a Group 10 element. Further, L represents a monoanionic ligand. In addition, n is 2 when the central metal M is a Group 9 element, or n is 1 when the central metal M is a Group 10 element.

Further, one embodiment of the present invention is an organometallic complex having a structure represented by the general formula (G8) below. The general formula (G8) below is a specific example of the organometallic complex having the structure of the general formula (G4), and is easy to synthesize and therefore preferable.

[Chemical formula 34]

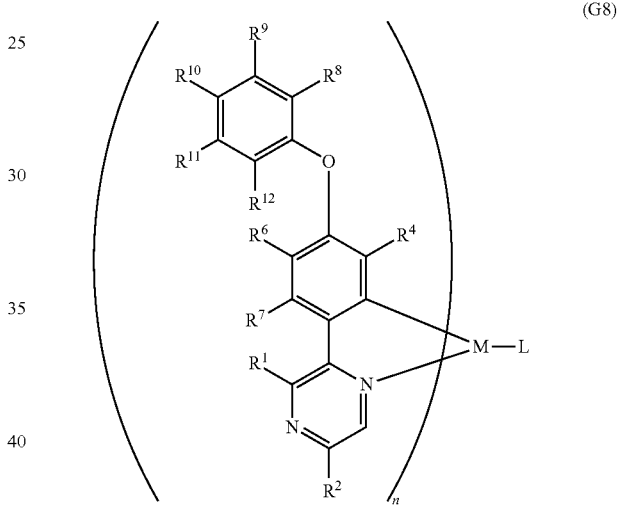

(G8)

In the above general formula (G8), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ represents hydrogen or an alkyl group having 1 to 4 carbon atoms. Furthermore, $R^4$, $R^6$, and $R^7$ separately represent any of hydrogen, an alkyl group having 1 to 4 carbon atoms, an alkoxy group having 1 to 4 carbon atoms, a halogen group, a trifluoromethyl group, and a phenyl group. Further, $R^8$, $R^9$, $R^{10}$, $R^{11}$, and $R^{12}$ separately represent any of hydrogen, an alkyl group having 1 to 4 carbon atoms, an alkoxy group having 1 to 4 carbon atoms, a halogen group, a trifluoromethyl group, and a phenyl group. Note that a phenyl group may be bonded to the alkyl group. In addition, M is a central metal and represents either a Group 9 element or a Group 10 element. Further, L represents a monoanionic ligand. In addition, n is 2 when the central metal M is a Group 9 element, or n is 1 when the central metal M is a Group 10 element.

Further, one embodiment of the present invention is an organometallic complex having a structure represented by the general formula (G9) below. The general formula (G9) below is a specific example of the organometallic complex having the structure of the general formula (G5), and is easy to synthesize and therefore preferable.

[Chemical formula 35]

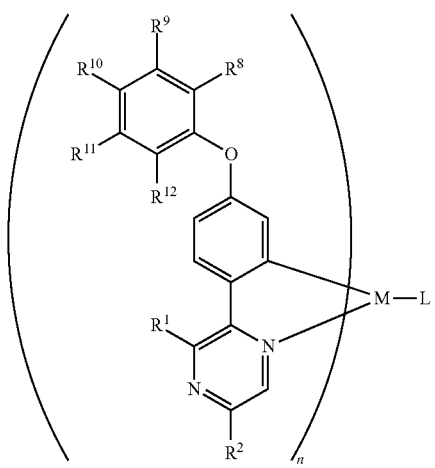
(G9)

In the above general formula (G9), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ represents hydrogen or an alkyl group having 1 to 4 carbon atoms. Further, $R^8$, $R^9$, $R^{10}$, $R^{11}$, and $R^{12}$ separately represent any of hydrogen, an alkyl group having 1 to 4 carbon atoms, an alkoxy group having 1 to 4 carbon atoms, a halogen group, a trifluoromethyl group, and a phenyl group. Note that a phenyl group may be bonded to the alkyl group. In addition, M is a central metal and represents either a Group 9 element or a Group 10 element. Further, L represents a monoanionic ligand. In addition, n is 2 when the central metal M is a Group 9 element, or n is 1 when the central metal M is a Group 10 element.

Each monoanionic ligand (L) in the above general formulae (G6) to (G9) is preferably any of a monoanionic bidentate chelate ligand having a β-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen. More preferably, the monoanionic ligand L is a monoanionic ligand represented by any of the structural formulae (L1) to (L6) below. These ligands have high coordination ability and are inexpensively available, and the time and cost for the synthesis can be saved accordingly.

[Chemical formulae 36]

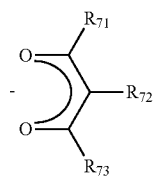
(L1)

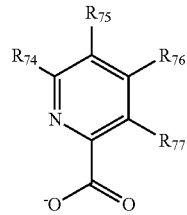
(L2)

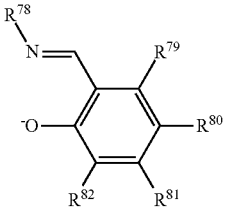
(L3)

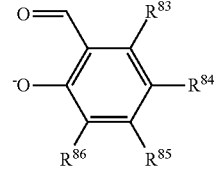
(L4)

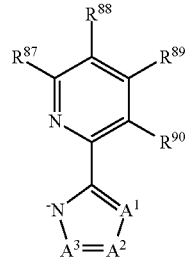
(L5)

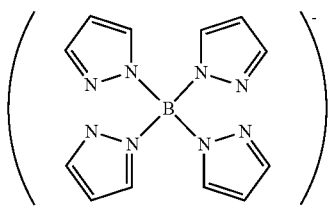
(L6)

In the above structural formulae (L1) to (L6), $R^{71}$ to $R^{90}$ separately represent any of hydrogen, an alkyl group having 1 to 4 carbon atoms, a halogen group, a haloalkyl group, an alkoxy group having 1 to 4 carbon atoms, and an alkylthio group having 1 to 4 carbon atoms. In addition, $A^1$, $A^2$, and $A^3$ separately represent nitrogen N or carbon C—R, and R represents hydrogen, an alkyl group having 1 to 4 carbon atoms, a halogen group, a haloalkyl group having 1 to 4 carbon atoms, or a phenyl group.

[Synthesis Method of Organometallic Complex Represented by General Formula (G10) and Specific Preferred Examples of Organometallic Complex Having Structure Represented by General Formula (G10)]

Next, a method of synthesizing the organometallic complex represented by the general formula (G10) below, which is a specific preferred example of the organometallic complex having the structure represented by the general formula (G1), will be described.

[Chemical formula 37]

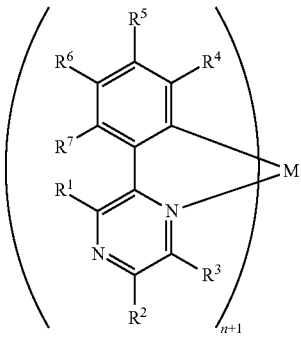

(G10)

As shown in a synthesis scheme (d) below, the phenylpyrazine derivative represented by the general formula (G0) is mixed with a compound of a Group 9 metal or a Group 10 metal which contains a halogen (e.g., rhodium chloride hydrate, palladium chloride, iridium chloride hydrate, ammonium hexachloroiridate, or potassium tetrachloroplatinate) or with an organometallic complex compound of a Group 9 metal or a Group 10 metal (e.g., an acetylacetonate complex or a diethylsulfide complex) and the mixture is then heated, so that the organometallic complex represented by the above general formula (G10) which is one embodiment of the present invention can be obtained. Further, this heating process may be performed after the phenylpyrazine derivative represented by the general formula (G0) and the compound of a Group 9 metal or a Group 10 metal which contains a halogen or the organometallic complex compound of a Group 9 metal or a Group 10 metal are dissolved in an alcohol-based solvent (e.g., glycerol, ethylene glycol, 2-metoxyethanol, or 2-ethoxyethanol). Note that in the scheme (d), M represents a Group 9 element or a Group 10 element. In addition, n is 2 when the central metal M is a Group 9 element, or n is 1 when the central metal M is a Group 10 element.

[Chemical formulae 38]

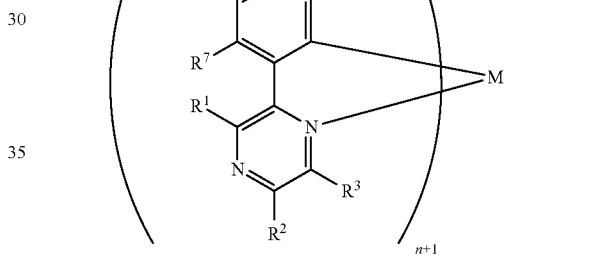

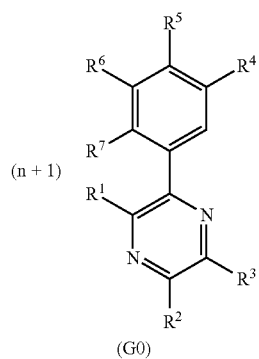

(G0)

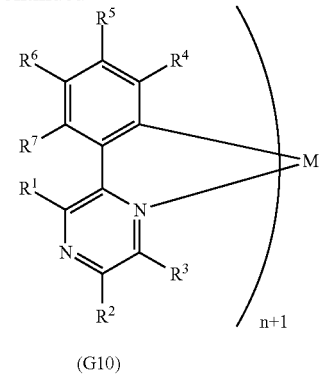

(G10)

The organometallic complex represented by the general formula (G10) below, which can be synthesized according to the scheme (d) as described above, is one embodiment of the present invention. The general formula (G10) below is a specific example of the organometallic complex having the structure of the general formula (G1), and is easy to synthesize and therefore preferable.

[Chemical formula 39]

(G10)

Note that in the above general formula (G10), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ and $R^3$ separately represent hydrogen or an alkyl group having 1 to 4 carbon atoms. Furthermore, at least one of the substituent groups $R^4$, $R^5$, $R^6$, and $R^7$ has the structure represented by the general formula (G2), and the other or others of the substituent groups separately represent any of hydrogen, an alkyl group having 1 to 4 carbon atoms, an alkoxy group having 1 to 4 carbon atoms, a halogen group, a trifluoromethyl group, and a phenyl group. Note that a phenyl group may be bonded to the alkyl group. In addition, M is a central metal and represents either a Group 9 element or a Group 10 element. In addition, n is 2 when the central metal M is a Group 9 element, or n is 1 when the central metal M is a Group 10 element.

Note that the general formula (G10) synthesized with use of the general formulae (G6) and (G0) also shows variations with a wide variety of ligands, since the organometallic complex, which has the structure represented by the general formula (G1) and is formed in such a way that the general formula (G0) is ortho-metalated by an ion of a Group 9 metal or of a Group 10 metal, shows variations with a wider variety of ligands due to the variations of the compounds (A1), (A2), (A1'), and (A2') used in the scheme (a) and the scheme (a'), as described above.

One embodiment of the present invention is an organometallic complex having a structure represented by the general formula (G11) below, which is among the variations with a wide variety of ligands. The general formula (G11) below is a specific example of the organometallic complex having the structure of the general formula (G3), and is easy to synthesize and therefore preferable.

[Chemical formula 40]

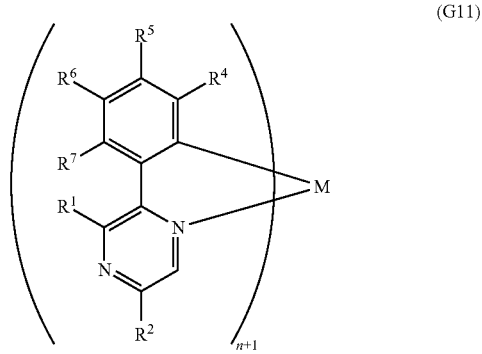

(G11)

In the above general formula (G11), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ represents hydrogen or an alkyl group having 1 to 4 carbon atoms. Furthermore, at least one of the substituent groups the functional substituent groups, $R^4$, $R^5$, $R^6$, and $R^7$ has the structure represented by the general formula (G2), and the other or others of the substituent groups have any of hydrogen, an alkyl group having 1 to 4 carbon atoms, an alkoxy group having 1 to 4 carbon atoms, a halogen group, a trifluoromethyl group, and a phenyl group. Note that a phenyl group may be bonded to the alkyl group. In addition, M is a central metal and represents either a Group 9 element or a Group 10 element. In addition, n is 2 when the central metal M is a Group 9 element, or n is 1 when the central metal M is a Group 10 element.

Further, one embodiment of the present invention is an organometallic complex having a structure represented by the general formula (G12) below. The general formula (G12) below is a specific example of the organometallic complex having the structure of the general formula (G4), and is easy to synthesize and therefore preferable.

[Chemical formula 41]

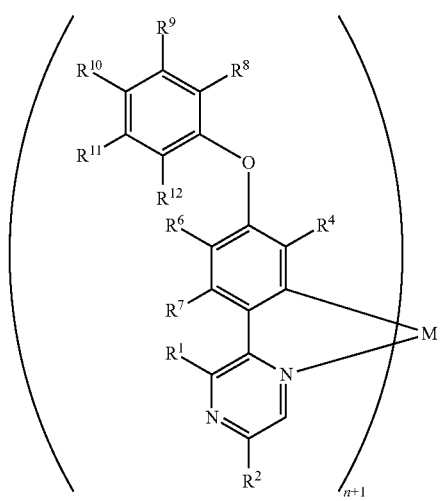

(G12)

In the above general formula (G12), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ represents hydrogen or an alkyl group having 1 to 4 carbon atoms. Furthermore, $R^4$, $R^6$, and $R^7$ separately represent any of hydrogen, an alkyl group having 1 to 4 carbon atoms, an alkoxy group having 1 to 4 carbon atoms, a halogen group, a trifluoromethyl group, and a phenyl group. Further, $R^8$, $R^9$, $R^{10}$, $R^{11}$, and $R^{12}$ separately represent any of hydrogen, an alkyl group having 1 to 4 carbon atoms, an alkoxy group having 1 to 4 carbon atoms, a halogen group, a trifluoromethyl group, and a phenyl group. Note that a phenyl group may be bonded to the alkyl group. In addition, M is a central metal and represents either a Group 9 element or a Group 10 element. In addition, n is 2 when the central metal M is a Group 9 element, or n is 1 when the central metal M is a Group 10 element.

Further, one embodiment of the present invention is an organometallic complex having a structure represented by the general formula (G13) below. The general formula (G13) below is a specific example of the organometallic complex having the structure of the general formula (G5), and is easy to synthesize and therefore preferable.

[Chemical formula 42]

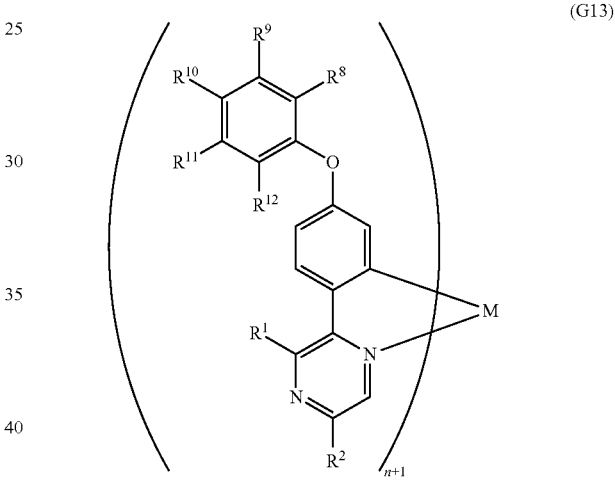

(G13)

In the above general formula (G13), $R^1$ represents any of an alkyl group having 1 to 4 carbon atoms, an alkoxy group having 1 to 4 carbon atoms, and an alkoxycarbonyl group having 1 to 5 carbon atoms. Further, $R^2$ represents hydrogen or an alkyl group having 1 to 4 carbon atoms. Further, $R^8$, $R^9$, $R^{10}$, $R^{11}$, and $R^{12}$ separately represent any of hydrogen, an alkyl group having 1 to 4 carbon atoms, an alkoxy group having 1 to 4 carbon atoms, a halogen group, a trifluoromethyl group, and a phenyl group. Note that a phenyl group may be bonded to the alkyl group. In addition, M is a central metal and represents either a Group 9 element or a Group 10 element. In addition, n is 2 when the central metal M is a Group 9 element, or n is 1 when the central metal M is a Group 10 element.

Although examples of the synthesis methods and specific examples of the organometallic complexes are described above, organometallic complexes which are disclosed embodiments of the present invention may be synthesized by another synthesis method.

Note that, for more efficient emission of phosphorescence, the central metal is preferably a metal that provides a heavy atom effect. Therefore, a feature of one embodiment of the present invention is that the central metal M in the above organometallic complexes which are embodiments of the present invention is iridium or platinum. Owing to the presence of a heavy atom such as iridium or platinum in the organometallic complex, a spin flip due to the heavy atom effect easily occurs. This increases the probability that an electron at the excited singlet level will be transferred by intersystem crossing to the excited triplet level, so that the above organometallic complex can emit phosphorescence efficiently, which is preferable.

The organometallic complexes which are embodiments of the present invention are each formed by combining the central metal M and the monoanionic ligand L described above, as appropriate. Specific structural formulae of the organometallic complexes which are embodiments of the present invention are given in structural formulae (100) to (148) below. Note that the present invention is not limited to these examples.

[Chemical formulae 43]

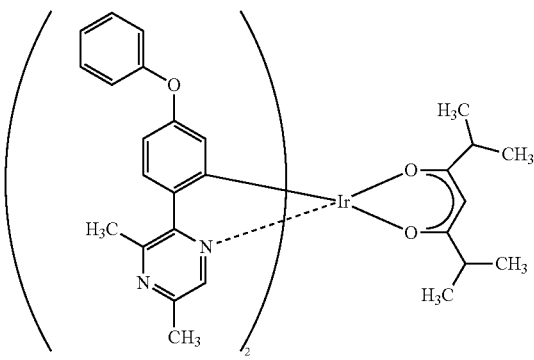

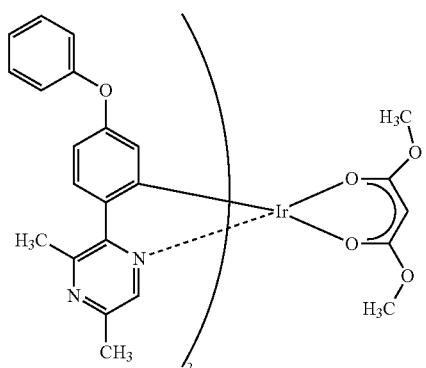

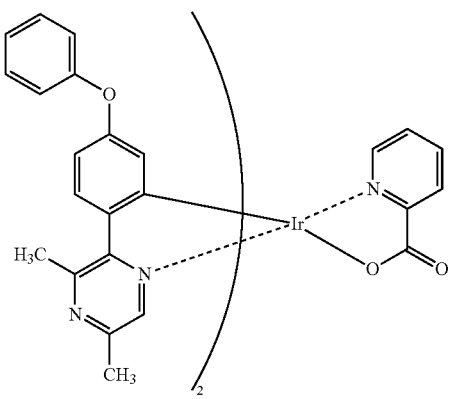

[Chemical formulae 44]

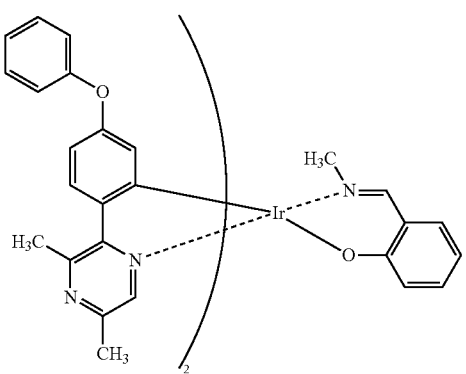

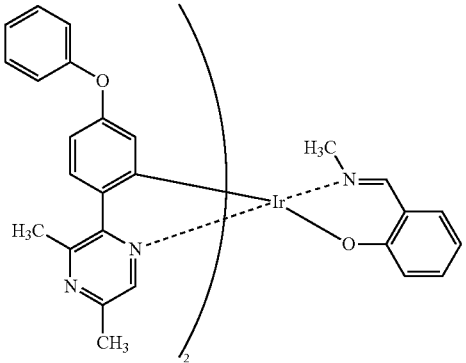

(107) 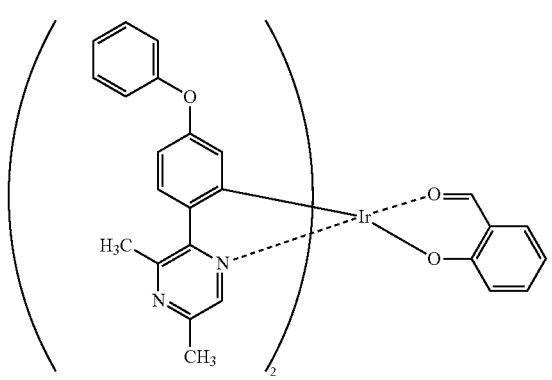
(108) 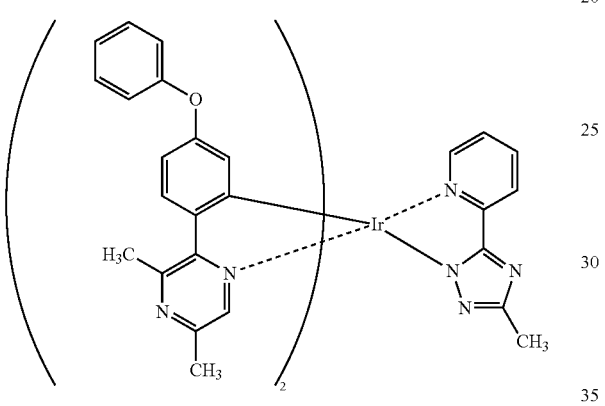
(109) 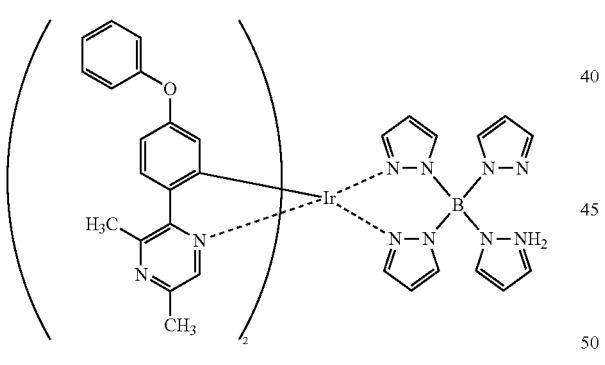
(110) 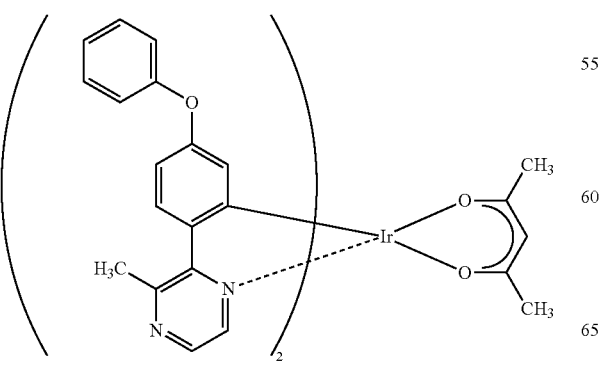
(111) 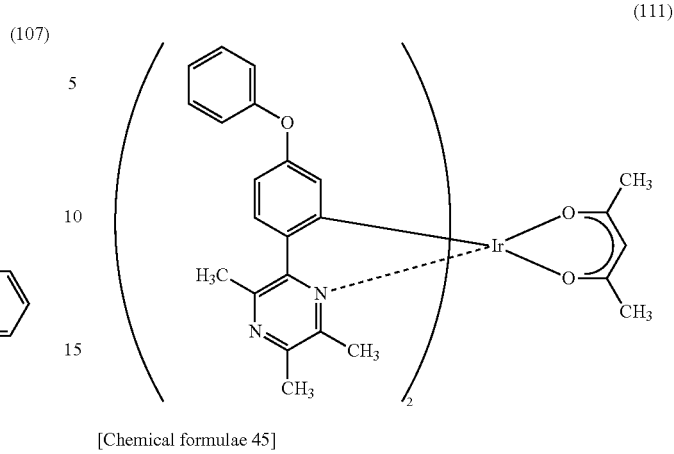
[Chemical formulae 45]
(112) 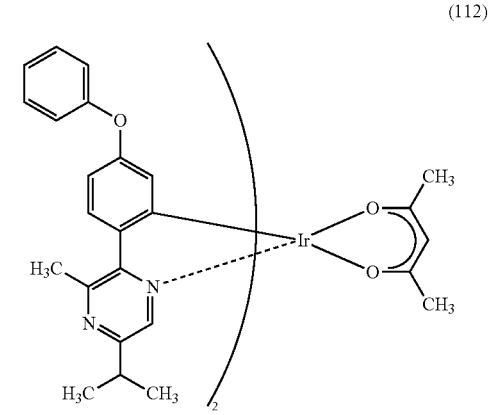
(113) 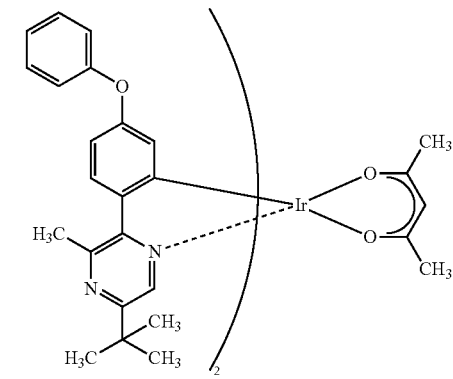
(114) 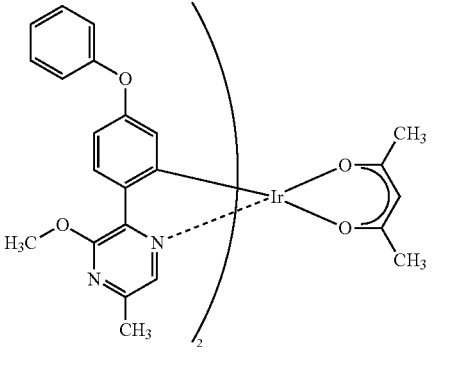

(115)
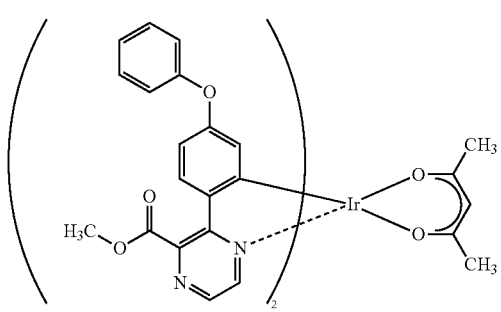
(116)
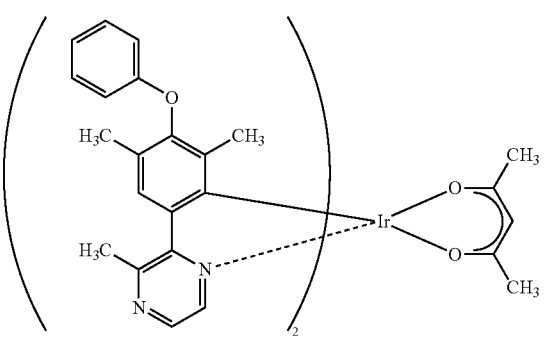
(117)
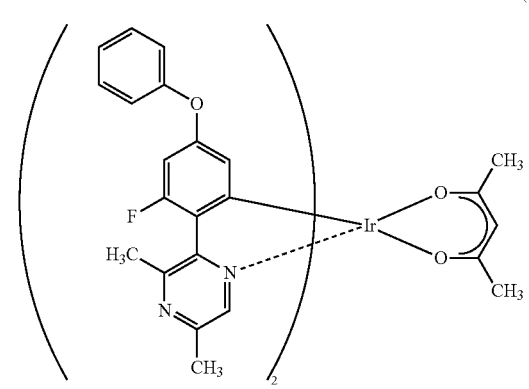
[Chemical formulae 46]
(118)
(119)
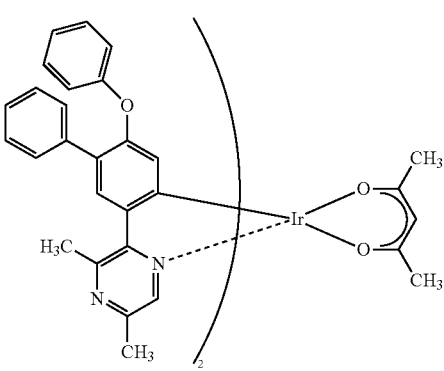
(120)
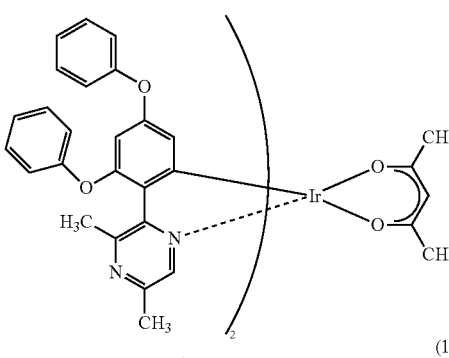
(121)
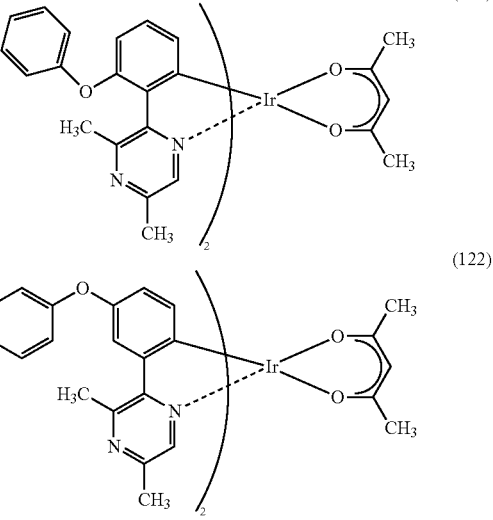
(122)
(123)
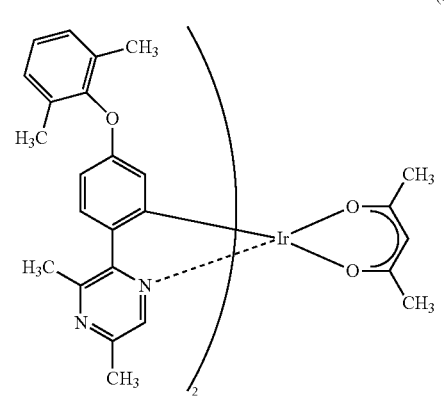

-continued
[Chemical formulae 47]
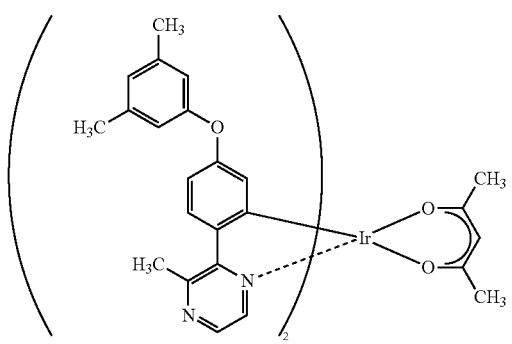
(124)
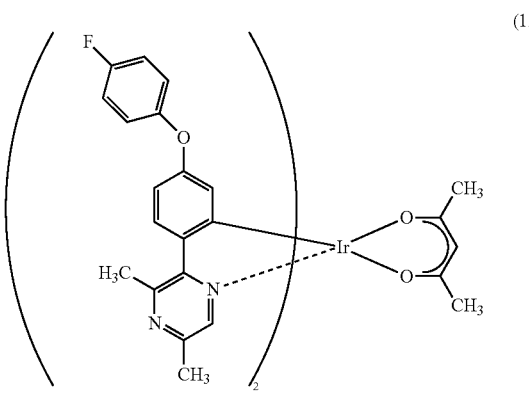
(125)
(126)
(127)
-continued
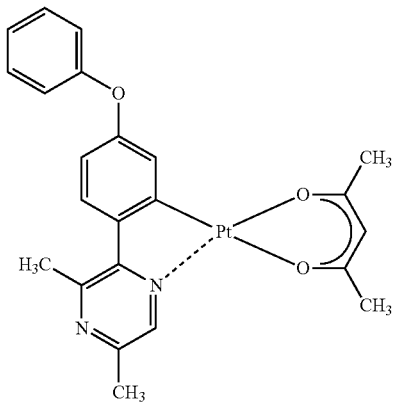
(128)
[Chemical formulae 48]
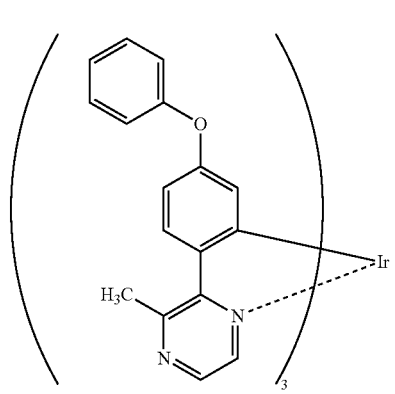
(129)
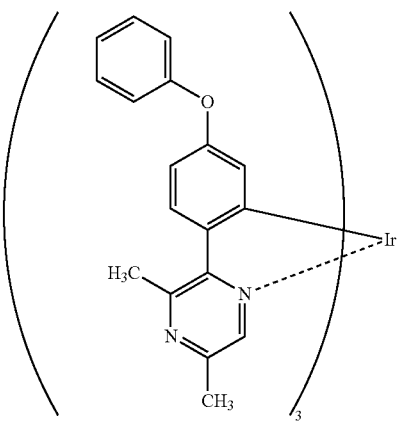
(130)
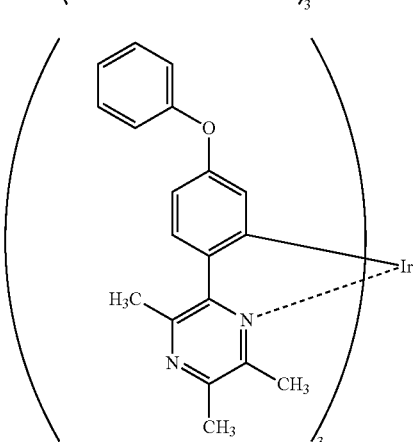
(131)

(132) 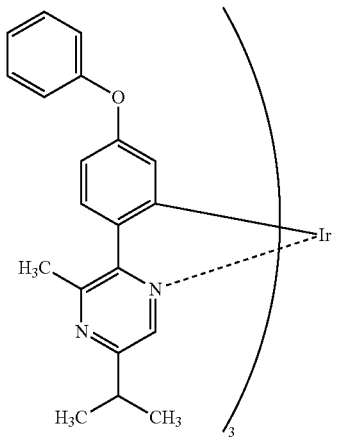
(133) 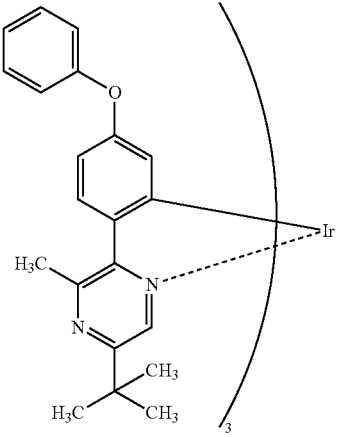
[Chemical formulae 49]
(134) 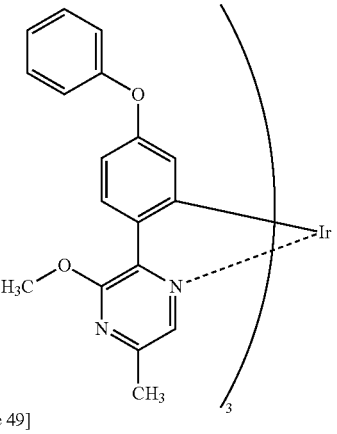
(135) 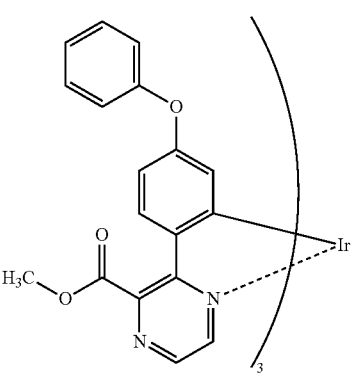
(136) 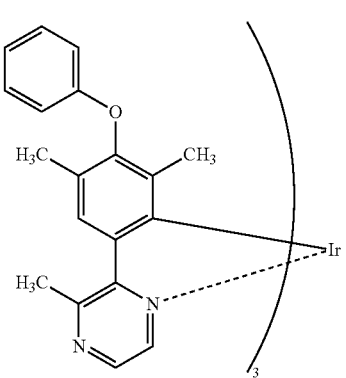
(137) 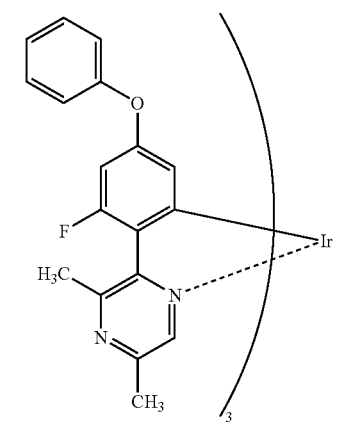
(138)
(139) 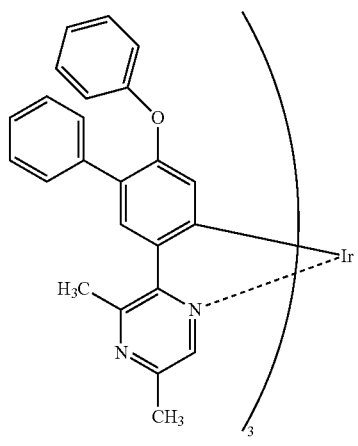

(140) 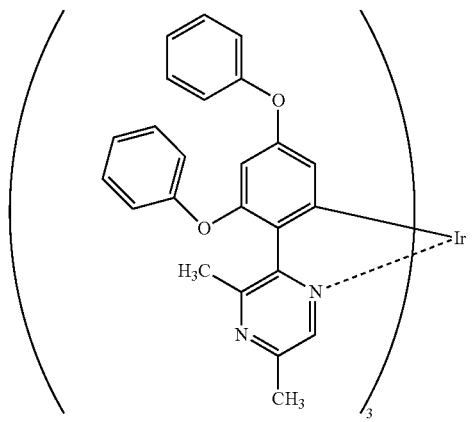
[Chemical formulae 50]
(141) 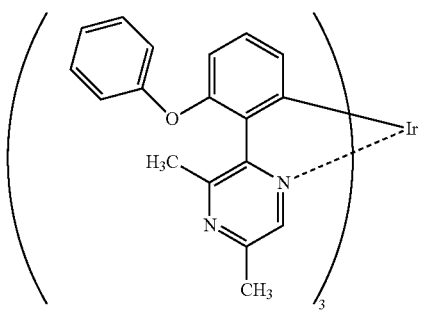
(142) 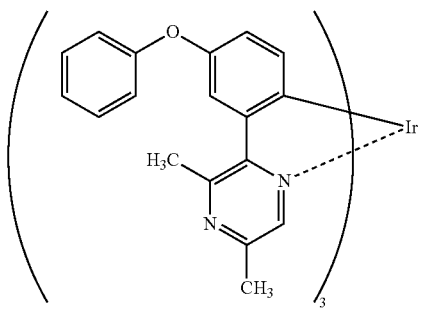
(143) 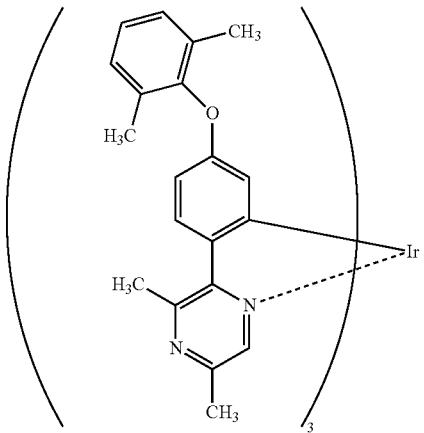
(144) 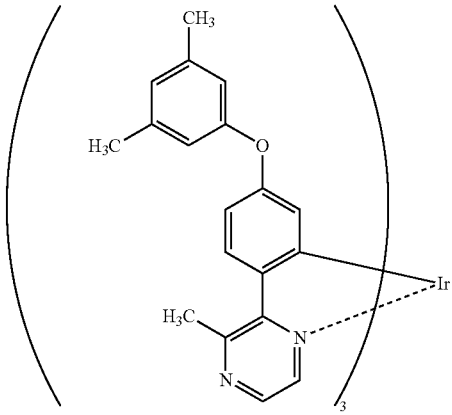
(145) 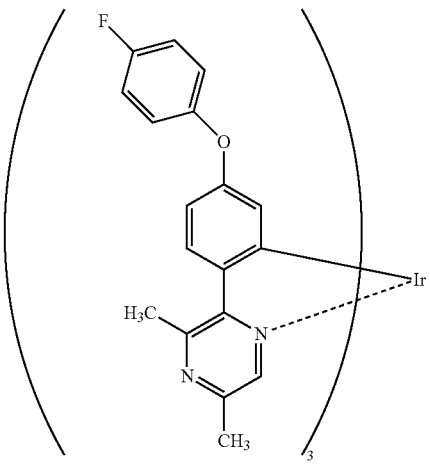
(146) 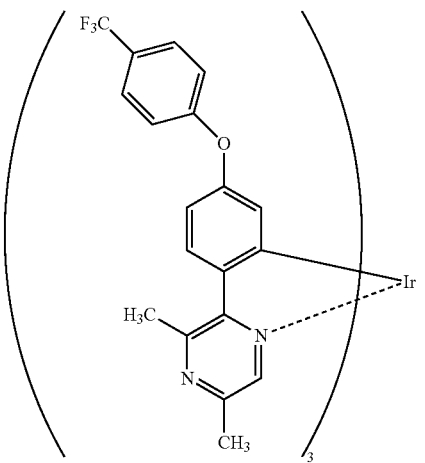

[Chemical formulae 51]

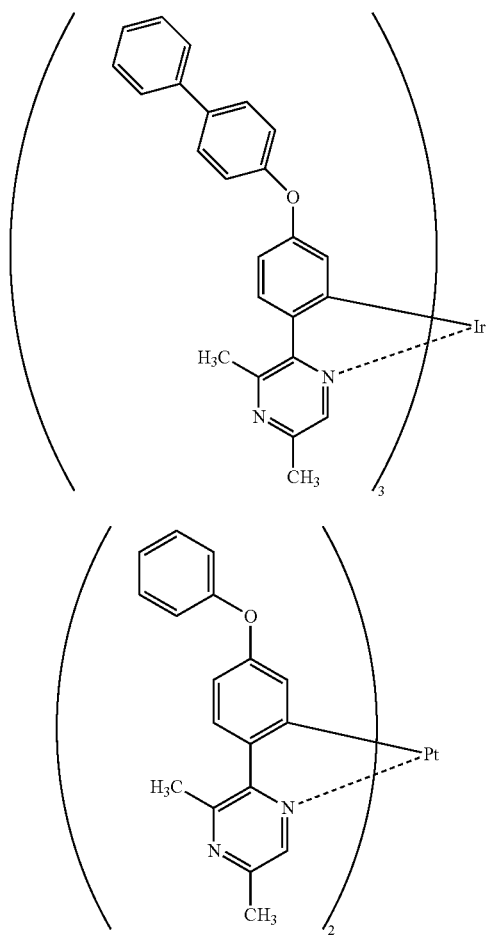

(147)

(148)

Depending on the type of the ligand, there can be stereoisomers of the organometallic complexes represented by the above structural formulae (100) to (148), and all these isomers are included in the category of the organometallic complexes which are embodiments of the present invention.

Further, the above-described organometallic complexes which are embodiments of the present invention can each be used as a sensitizer owing to its capability of intersystem crossing. Furthermore, since the organometallic complexes are capable of emitting phosphorescence, they can each be used as a light-emitting material or a light-emitting substance for a light-emitting element.

(Embodiment 2)

In Embodiment 2, as one embodiment of the present invention, a light-emitting element in which an organometallic complex is used for a light-emitting layer will be described with reference to FIG. 1.

FIG. 1 illustrates a light-emitting element in which an EL layer 102 including a light-emitting layer 113 is interposed between a first electrode 101 and a second electrode 103. The light-emitting layer 113 contains any of the organometallic complexes which are embodiments of the present invention and described in Embodiment 1.

By application of a voltage to such a light-emitting element, holes injected from the first electrode 101 side and electrons injected from the second electrode 103 side recombine in the light-emitting layer 113 to raise the organometallic complex to an excited state. Then, light is emitted when the organometallic complex in the excited state returns to the ground state. Thus, the organometallic complex of one embodiment of the present invention functions as a light-emitting substance in the light-emitting element. Note that in the light-emitting element described in this embodiment, the first electrode 101 functions as an anode and the second electrode 103 functions as a cathode.

When the first electrode 101 functions as an anode, any of metals, alloys, or electrically conductive compounds, mixtures or stacked layers thereof, and the like which has a high work function (specifically, a work function of 4.0 eV or more) is preferably used for the first electrode 101. Specific examples are indium oxide-tin oxide (ITO: indium tin oxide), indium oxide-tin oxide containing silicon or silicon oxide, indium oxide-zinc oxide (IZO: indium zinc oxide), indium oxide containing tungsten oxide and zinc oxide, and the like. Other than these, gold (Au), platinum (Pt), nickel (Ni), tungsten (W), chromium (Cr), molybdenum (Mo), iron (Fe), cobalt (Co), copper (Cu), palladium (Pd), titanium (Ti), or the like can be used.

Alternatively, an electrically conductive high molecule (an electrically conductive polymer) can be used for the first electrode 101. Specifically, PEDOT (polyethylenedioxythiophene) and the like can be given.

When a layer included in the EL layer 102 which is formed in contact with the first electrode 101 is formed using a later described composite material formed by combining an organic compound and an electron acceptor (an acceptor), as a substance used for the first electrode 101, any of a variety of metals, alloys, and electrically-conductive compounds, a mixture thereof, and the like can be used regardless of the work function; for example, aluminum (Al), silver (Ag), an alloy containing aluminum (e.g., Al—Si), or the like can also be used.

Note that the first electrode 101 can be formed by, for example, a sputtering method, an evaporation method (including a vacuum evaporation method), or the like. Alternatively, a coating method, a printing method, an inkjet method, or the like can be used.

The EL layer 102 formed over the first electrode 101 has at least the light-emitting layer 113 and is formed to include any of the organometallic complexes which are embodiments of the present invention. For part of the EL layer 102, a known substance can be used, and either a low molecular compound or a high molecular compound can be used. Note that substances forming the EL layer 102 may consist of organic compounds or may include an inorganic compound as a part.

Further, as illustrated in FIG. 1, the EL layer 102 may include a hole-injection layer 111 containing a substance having a high hole-injection property, a hole-transport layer 112 containing a substance having a high hole-transport property, an electron-transport layer 114 containing a substance having a high electron-transport property, an electron-injection layer 115 containing a substance having a high electron-injection property, and the like in appropriate combination in addition to the light-emitting layer 113.

The hole-injection layer 111 is a layer containing a substance having a high hole-injection property. Examples of the substance having a high hole-injection property which can be used are metal oxides, such as molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide. Alternatively, phthalocyanine-based compounds, such as phthalocyanine (abbreviation: $H_2Pc$) and copper(II) phthalocyanine (abbreviation: CuPc), can be used.

Other examples of the substance that can be used are aromatic amine compounds which are low molecular organic compounds, such as 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1).

Still other examples of the substance that can be used are high molecular compounds (e.g., oligomers, dendrimers, and polymers), such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl) benzidine] (abbreviation: Poly-TPD), and high molecular compounds to which acid is added, such as poly(3,4-ethylenedioxythiophene)/poly(styrenesulfonic acid) (PEDOT/PSS), and polyaniline/poly(styrenesulfonic acid) (PAni/PSS).

For the hole-injection layer 111, the composite material formed by combining an organic compound and an electron acceptor (also referred to as an acceptor, a generic name for a compound in the state where an electron is easily received, among compounds serving for electron transfer reaction) may be used. Such a composite material is excellent in injection and transport of holes because the action of the electron acceptor enables holes to be generated in the hole-injection layer 111. In this case, the organic compound is preferably a material excellent in transport of the generated holes (a substance having a high hole-transport property).

Examples of the organic compound used for the composite material are a variety of compounds, such as aromatic amine compounds, carbazole derivatives, aromatic hydrocarbons, and high molecular compounds (e.g., oligomers, dendrimers, and polymers). The organic compound used for the composite material is preferably organic compounds having a high hole-transport property, and specifically preferably a substance having a hole mobility of $10^{-6}$ cm$^2$/Vs or more. Note that other than these substances, any substance that has a property of transporting more holes than electrons may be used. Organic compounds that can be used for the composite material will be specifically described below.

Examples of the organic compound that can be used for the composite material are aromatic amine compounds, such as TDATA, MTDATA, DPAB, DNTPD, DPA3B, PCzPCA1, PCzPCA2, PCzPCN1, 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), and 4-phenyl-4'-(9-phenylfluoren-9-yl) triphenylamine (abbreviation: BPAFLP), and carbazole derivatives, such as 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)phenyl]-10-phenylanthracene (abbreviation: CzPA), 9-phenyl-3-[4-(10-phenyl-9-anthryl)phenyl]-9H-carbazole (abbreviation: PCzPA), and 1,4-bis[4-(N-carbazolyl)phenyl-2,3,5,6-tetraphenylbenzene.

Other examples of the organic compound that can be used are aromatic hydrocarbon compounds, such as 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butylanthracene, 9,10-bis[2-(1-naphthyl)phenyl]anthracene, and 2,3,6,7-tetramethyl-9,10-di(1-naphthyl)anthracene.

Other examples of the organic compound that can be used are aromatic hydrocarbon compounds, such as 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), and 9,10-bis[4-(2,2-diphenylvinyl)phenyl]anthracene (abbreviation: DPVPA).

Further, examples of the electron acceptor are organic compounds, such as 7,7,8,8-tetracyano-2,3,5,6-tetrafluoroquinodimethane (abbreviation: F$_4$-TCNQ) and chloranil, transition metal oxides, and oxides of metals that belong to Groups 4 to 8 in the periodic table. Specific preferred examples include vanadium oxide, niobium oxide, tantalum oxide, chromium oxide, molybdenum oxide, tungsten oxide, manganese oxide, and rhenium oxide because their electron-acceptor properties are high. Among these, molybdenum oxide is especially preferable since it is stable in the air and its hygroscopic property is low and is easily treated.

The composite material may be formed using the above-described electron acceptor and the above-described high molecular compound, such as PVK, PVTPA, PTPDMA, or Poly-TPD, and used for the hole-injection layer 111.

The hole-transport layer 112 is a layer that contains a substance having a high hole-transport property. As the substance having a high hole-transport property, the following aromatic amine compounds can be given: NPB, TPD, BPAFLP, 4,4'-bis[N-(9,9-dimethylfluoren-2-yl)-N-phenylamino]biphenyl (abbreviation: DFLDPBi), 4,4'-bis[N-(spiro-9,9'-bifluoren-2-yl)-N-phenylamino]biphenyl (abbreviation: BSPB), and the like. The substances mentioned here are mainly substances that have a hole mobility of $10^{-6}$ cm$^2$/Vs or more. Note that other than the above substances, any substance that has a property of transporting more holes than electrons may be used. Further, the layer containing a substance having a high hole-transport property is not limited to a single layer, and may be a stack of two or more layers containing any of the above substances.

For the hole-transport layer 112, a carbazole derivative, such as CBP, CzPA, or PCzPA, or an anthracene derivative, such as t-BuDNA, DNA, or DPAnth, may be used.

For the hole-transport layer 112, a high molecular compound, such as PVK, PVTPA, PTPDMA, or Poly-TPD, can be used.

The light-emitting layer 113 is a layer containing any of the organometallic complexes which are embodiments of the present invention, and preferably a layer in which the organometallic complex which is one embodiment of the present invention is dispersed as a guest material in a substance as a host material which has higher triplet excitation energy than the organometallic complex which is one embodiment of the present invention; thus, quenching of light emission from the organometallic complex caused depending on the concentration can be prevented. Note that the triplet excitation energy indicates an energy gap between a ground state and a triplet excited state.

The substance (i.e. host material) used for dispersing any of the above-described organometallic complexes is preferably, but not limited to, any of compounds having an arylamine skeleton, such as 2,3-bis(4-diphenylaminophenyl)quinoxaline (abbreviation: TPAQn) and NPS, carbazole derivatives such as CBP and 4,4',4"-tris(N-carbazolyl)triphenylamine (abbreviation: TCTA), and metal complexes such as bis[2-(2-hydroxyphenyl)pyridinato]zinc (abbreviation: $Znpp_2$), bis[2-(2-hydroxyphenyl)benzoxazolato]zinc (abbreviation: $Zn(BOX)_2$), bis(2-methyl-8-quinolinolato)(4-phenylphenolato)aluminum (abbreviation: BAlq), and tris(8-quinolinolato)aluminum (abbreviation: $Alq_3$). Alternatively, a high molecular compound such as PVK can be used.

The electron-transport layer 114 is a layer containing a substance having a high electron-transport property. For the electron-transport layer 114, metal complexes such as $Alq_3$, tris(4-methyl-8-quinolinolato)aluminum (abbreviation: $Almq_3$), bis(10-hydroxybenzo[h]-quinolinato)beryllium (abbreviation: $BeBq_2$), BAlq, $Zn(BOX)_2$, and bis[2-(2-hydroxyphenyl)benzothiazolato]zinc (abbreviation: $Zn(BTZ)_2$) can be given.

Other examples of the substance that can be used are heteroaromatic compounds, such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzoxazol-2-yl)stilbene (abbreviation: BzOs).

A high molecular compound, such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can also be used.

The substances described above are mainly substances having an electron mobility of $10^{-6}$ cm$^2$/Vs or more. Note that other than the above substances, any substance that has a property of transporting more electrons than holes may be used for the electron-transport layer.

Further, the electron-transport layer 114 is not limited to a single layer, and may be a stack of two or more layers containing any of the above substances are stacked.

The electron-injection layer 115 is a layer that contains a substance having a high electron-injection property. Examples of the substance that can be used for the electron-injection layer 115 are alkali metals, alkaline-earth metals, and compounds thereof, such as lithium (Li), cesium (Cs), calcium (Ca), lithium fluoride (LiF), cesium fluoride (CsF), calcium fluoride ($CaF_2$), and lithium oxide (LiOx), rare earth-metal compounds, such as erbium fluoride ($ErF_3$), and the above-mentioned substances for forming the electron-transport layer 114.

Alternatively, the composite material formed by combining an organic compound and an electron donor (also referred to as a donor, a generic name for a compound in the state which easily releases an electron, among compounds serving for electron transfer reaction) may be used for the electron-injection layer 115. Such a composite material is excellent in injection and transport of electrons because the action of the electron donor enables electrons to be generated in the organic compound. In this case, the organic compound is preferably a material excellent in transport of the generated electrons; specifically, the above-described substances for forming the electron-transport layer 114 (e.g., a metal complex or a heteroaromatic compound) can be used, for example. The electron donor can be a substance exhibiting an electron-donating property for the organic compound. Specific examples of the electron donor are alkali metals, alkaline-earth metals, and rare earth-metals, such as lithium, cesium, magnesium, calcium, erbium, and ytterbium. Alkali metal oxides and alkaline-earth metal oxides are preferable, examples of which are lithium oxide, calcium oxide, barium oxide, and the like, and a Lewis base such as magnesium oxide or an organic compound such as tetrathiafulvalene (abbreviation: TTF) can be used.

Note that the hole-injection layer 111, the hole-transport layer 112, the light-emitting layer 113, the electron-transport layer 114, and the electron-injection layer 115 which are described above can each be formed by a method, such as an evaporation method (including a vacuum evaporation method), a coating method, a printing method, or an inkjet method.

When the second electrode 103 functions as a cathode, any of metals, alloys, electrically conductive compounds, mixtures thereof, and the like which has a low work function (specifically, a work function of 3.8 eV or less) is preferably used for the second electrode 103. Specific examples of the substance that can be used are elements that belong to Groups 1 and 2 in the periodic table, that is, alkali metals such as lithium (Li) and cesium (Cs), alkaline earth-metals such as magnesium (Mg), calcium (Ca), and strontium (Sr), alloys thereof (e.g., Mg—Ag and Al—Li), rare earth-metals such as europium (Eu) and ytterbium (Yb), alloys thereof, aluminum, silver, and the like.

Alternatively, an electrically conductive high molecule (an electrically conductive polymer) can be used for the second electrode 103. Specifically, PEDOT (polyethylenedioxythiophene) and the like can be given.

When a layer included in the EL layer 102 which is formed in contact with the second electrode 103 is formed using the composite material formed by combining the organic compound and the electron donor (donor), which are described above, a variety of electrically conductive materials such as Al, Ag, ITO, and indium oxide-tin oxide containing silicon or silicon oxide can be used regardless of the work function.

Note that when the second electrode 103 is formed, a vacuum evaporation method, a sputtering method, or the like can be used. Alternatively, a coating method, a printing method, an inkjet method, or the like can be used.

In the above-described light-emitting element, a current flows due to a potential difference generated between the first electrode 101 and the second electrode 103 and holes and electrons recombine in the EL layer 102, so that light is emitted. Then, this light emission is extracted outside through one or both of the first electrode 101 and the second electrode 103. Therefore, one or both of the first electrode 101 and the second electrode 103 are electrodes having a property of transmitting visible light (specifically, preferably a visible light transmittance greater than or equal to 50%, more preferably greater than or equal to 80%).

Note that by use of the light-emitting element described in this embodiment, a passive matrix light-emitting device or an active matrix light-emitting device in which driving of the light-emitting element is controlled by a thin film transistor (TFT) can be fabricated.

In fabrication of an active matrix light-emitting device, there is no particular limitation on the structure of the TFT; for example, a staggered TFT or an inverted staggered TFT can be used as appropriate. In addition, a driver circuit formed in a TFT substrate may be formed with an n-type TFT and a p-type TFT, or with either an n-type TFT or a p-type TFT. Further, there is no particular limitation on the crystallinity of a semiconductor film used for the TFT; for example, an amorphous semiconductor film, a crystalline semiconductor film, an oxide semiconductor film, an organic semiconductor film, or the like can be used.

According to this embodiment, a light-emitting element including the light-emitting layer 113 that emits phosphorescence highly efficiently, which is one embodiment of the present invention, can be fabricated as described above. Thus, a light-emitting element with high light emission efficiency can be obtained. Further, a light-emitting element that emits yellow light emission with high luminance can also be obtained, when any of the organometallic complexes capable of emitting yellow phosphorescence with high luminance, which are embodiments of the present invention, is used for the light-emitting layer 113, for example.

Note that in Embodiment 2, any of the structures described in Embodiment 1 can be used in appropriate combination.

(Embodiment 3)

The light-emitting element which is one embodiment of the present invention may have a plurality of light-emitting layers. The plurality of light-emitting layers is provided and light is emitted from each light-emitting layer, so that light emission in which a plurality of light emissions is mixed can be obtained. Thus, for example, white light emission can be obtained. In Embodiment 3, a mode of a light-emitting element having a plurality of light-emitting layers will be described with reference to FIG. 2.

Figure 2:
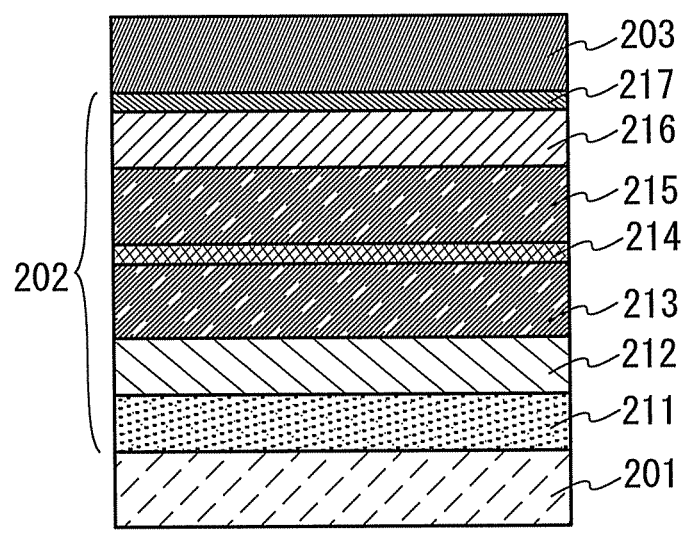
FIG. 2 illustrates a light-emitting element which is one embodiment of the present invention.

In FIG. 2, an EL layer 202 is provided between a first electrode 201 and a second electrode 203, and a first light-emitting layer 213 and a second light-emitting layer 215 are provided in the EL layer 202. A mixture of light emission from the first light-emitting layer 213 and light emission from the second light-emitting layer 215 can be obtained. Note that there is preferably a separation layer 214 between the first light-emitting layer 213 and the second light-emitting layer 215. In the light-emitting element described in this embodiment, the first electrode 201 functions as an anode and the second electrode 203 functions as a cathode.

When a voltage is applied so that the potential of the first electrode 201 is higher than that of the second electrode 203, a current flows between the first electrode 201 and the second electrode 203, and holes and electrons recombine in at least one of the first light-emitting layer 213, the second light-emitting layer 215, and the separation layer 214. Generated excitation energy is distributed to both the first light-emitting layer 213 and the second light-emitting layer 215 to raise each of a first light-emitting substance contained in the first light-emitting layer 213 and a second light-emitting substance contained in the second light-emitting layer 215 to an excited state. The first and second light-emitting substances each in the excited state emit light while returning to the ground state.

The first light-emitting layer 213 contains the first light-emitting substance, typical examples of which are fluorescent compounds such as perylene, 2,5,8,11-tetra(tert-butyl) perylene (abbreviation: TBP), DPVBi, 4,4'-bis[2-(N-ethyl-carbazol-3-yl)vinyl]biphenyl (abbreviation: BCzVBi), BAlq, and bis(2-methyl-8-quinolinolato)galliumchloride (abbreviation: $Gamq_2Cl$), and phosphorescent compounds such as bis{2-[3,5-bis(trifluoromethyl)phenyl]pyridinato-N, $C^{2'}$}iridium(III)picolinate (abbreviation: $Ir(CF_3\ ppy)_2(pic)$), bis[2-(4,6-difluorophenyl)pyridinato-N,$C^{2'}$]iridium(III) acetylacetonate (abbreviation: FIr(acac)), bis[2-(4,6-difluorophenyl)pyridinato-N,$C^{2'}$]iridium(III)picolinate (abbreviation: FIrpic), and bis[2-(4,6-difuluorophenyl) pyridinato-N, $C^{2'}$]iridium(III)tetra(1-pyrazolyl)borate (abbreviation: FIr6), to emit light having an emission spectrum with a peak at 450 nm to 510 nm (i.e. blue light to blue green light).

In addition, when the first light-emitting substance is a fluorescent compound, the first light-emitting layer 213 preferably has a structure in which the first light-emitting substance is dispersed as a guest material in a substance as a first host material which has higher singlet excitation energy than the first light-emitting substance. Alternatively, when the first light-emitting substance is a phosphorescent compound, the first light-emitting layer 213 preferably has a structure in which the first light-emitting substance is dispersed as a guest material in a substance as the first host material which has higher triplet excitation energy than the first light-emitting substance. As the first host material, DNA, t-BuDNA, or the like can be used other than NPB, CBP, TCTA, and the like described above. Note that the singlet excitation energy is an energy difference between a ground state and a singlet excited state. In addition, the triplet excitation energy is an energy difference between a ground state and a triplet excited state.

The second light-emitting layer 215 includes any of the organometallic complexes which are embodiments of the present invention and emits yellow light. The second light-emitting layer 215 can have the same structure as the light-emitting layer 113 described in Embodiment 2.

Specifically, the separation layer 214 can be formed using TPAQn, NPB, CBP, TCTA, $Znpp_2$, ZnBOX or the like described above. Such provision of the separation layer 214 can prevent a defect in which only one of the first light-emitting layer 213 and the second light-emitting layer 215 has excessively high emission intensity. Note that although not necessarily needed, the separation layer 214 can be provided as appropriate to adjust the ratio in emission intensity of the first light-emitting layer 213 to the second light-emitting layer 215.

Although any of the organometallic complexes which are embodiments of the present invention and another light-emitting substance are used for the second light-emitting layer 215 and the first light-emitting layer 213, respectively, in Embodiment 3, any of the organometallic complexes which are embodiments of the present invention and another light-emitting substance may be used for the first light-emitting layer 213 and the second light-emitting layer 215, respectively.

Further, although the light-emitting element in which two light-emitting layers are provided as illustrated in FIG. 2 is described in Embodiment 3, the number of the light-emitting layers is not limited to two and may be three, for example, so that light emissions from the light-emitting layers can be mixed. Thus, white light emission, for example, can be obtained.

Note that the first electrode 201 can have the same structure as the first electrode 101 described in Embodiment 2. Similarly, the second electrode 203 can have the same structure as the second electrode 103 described in Embodiment 2.

In Embodiment 3, the hole-injection layer 211, the hole-transport layer 212, the electron-transport layer 216, and the electron-injection layer 217 are provided, as illustrated in FIG. 2; as for structures of these layers, the structures of the respective layers described in Embodiment 2 can be applied. However, these layers are not necessarily needed and may be provided as appropriate according to element characteristics.

According to Embodiment 3, light emission in which a plurality of light emissions is mixed can be obtained as described above. Thus, a light-emitting element that emits white light as a whole can be obtained by making the emission colors of the first and second light-emitting layers complementary colors, for example. Note that the term "complementary colors" means a color relationship in which an achromatic color is obtained when the colors are mixed. In sum, white light emission can be obtained by a mixture of lights from substances whose emission colors are complementary colors.

For example, white light emission can be obtained when any of the organometallic complexes capable of emitting yellow phosphorescence with high luminance, which are embodiments of the present invention in this specification, is used for the first light-emitting layer and a material capable of emitting blue light is used for the second light-emitting layer.

Note that the structure described in Embodiment 3 can be combined with any of the structures described in Embodiment 1 or 2 as appropriate.

(Embodiment 4)

Figure 3:
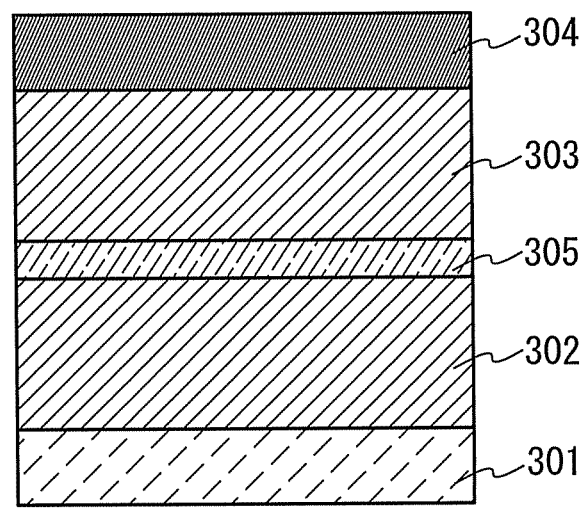
FIG. 3 illustrates a light-emitting element which is one embodiment of the present invention.

In Embodiment 4, as one embodiment of the present invention, a structure of a light-emitting element which includes a plurality of EL layers (hereinafter, referred to as a stacked-type element) will be described with reference to FIG. 3. This light-emitting element is a stacked-type light-emitting element having a plurality of EL layers (a first EL layer 302 and a second EL layer 303) between a first electrode 301 and a second electrode 304. Note that the number of the EL layers is two in this embodiment but may be three or more.

In this embodiment, the first electrode 301 functions as an anode, and the second electrode 304 functions as a cathode. Note that the first electrode 301 and the second electrode 304 can each have the same structures as in Embodiment 2. Further, all or any of the plurality of EL layers (the first EL layer 302 and the second EL layer 303) may have the same structure as the EL layer described in Embodiment 2. In other words, the structures of the first EL layer 302 and the second EL layer 303 may be the same as or different from each other.

Further, a charge generation layer 305 is provided between the plurality of EL layers (the first EL layer 302 and the second EL layer 303). The charge generation layer 305 has a function of injecting electrons into one of the EL layers and injecting holes into the other of the EL layers when a voltage is applied to the first electrode 301 and the second electrode 304. In this embodiment, the case where a voltage is applied so that the potential of the first electrode 301 is higher than that of the second electrode 304 is described; in this case, the charge generation layer 305 injects electrons into the first EL layer 302 and injects holes into the second EL layer 303.

Note that the charge generation layer 305 preferably has a property of transmitting visible light (specifically, preferably a visible light transmittance greater than or equal to 50%, more preferably greater than or equal to 80%) in terms of light extraction efficiency. Further, the charge generation layer 305 functions even if it has lower electrical conductivity than the first electrode 301 or the second electrode 304.

For the charge generation layer 305, a structure containing an organic compound having a high hole-transport property and an electron acceptor (an acceptor) should be used, or a structure containing an organic compound having a high electron-transport property and an electron donor (a donor) may be used. A structure in which both the structures are stacked may be used.

In the case of the structure in which the electron acceptor is added to the organic compound having a high hole-transport property, examples of the substance that can be used as the organic compound having a high hole-transport property are aromatic amine compounds such as NPS, TPD, TDATA, MTDATA, and 4,4'-bis[N-(spiro-9,9'-bifluoren-2-yl)-N-phenylamino]biphenyl (abbreviation: BSPB), and the like. The substances mentioned here are mainly substances that have a hole mobility of $10^{-6}$ cm$^2$/Vs or more. Note that other than the above substances, any substance that has a property of transporting more holes than electrons may be used.

In addition, examples of the electron acceptor are 7,7,8,8-tetracyano-2,3,5,6-tetrafluoroquinodimethane (abbreviation: F$_4$-TCNQ), chloranil, oxides of transition metals, and oxides of metals that belong to Groups 4 to 8 in the periodic table, and the like. Specific preferred examples include vanadium oxide, niobium oxide, tantalum oxide, chromium oxide, molybdenum oxide, tungsten oxide, manganese oxide, and rhenium oxide because of their high electron-acceptor properties. Among these, especially molybdenum oxide is preferable since it is stable in the air and its hygroscopic property is low and is easily treated.

Further, in the case of the structure in which the electron donor is added to the organic compound having a high electron-transport property, examples of the organic compound having a high electron-transport property which can be used are metal complexes having a quinoline skeleton or a benzoquinoline skeleton such as Alq, Almq$_3$, BeBq$_2$, and BAlq, metal complexes having an oxazole-based ligand or a thiazole-based ligand, such as Zn(BOX)$_2$ and Zn(BTZ)$_2$, and the like. Examples other than the metal complexes are PBD, OXD-7, TAZ, BPhen, BCP, and the like. The substances described here are mainly substances having an electron mobility of $10^{-6}$ cm$^2$/Vs or more. Note that other than the above substances, any organic compound that has a property of transporting more electrons than holes may be used.

Examples of the electron donor that can be used are alkali metals, alkaline-earth metals, rare-earth metals, metals that belong to Group 13 in the periodic table and oxides or carbonates thereof, and preferably specifically lithium (Li), cesium (Cs), magnesium (Mg), calcium (Ca), ytterbium (Yb), indium (In), lithium oxide, cesium carbonate, and the like. An organic compound such as tetrathianaphthacene may be used as the electron donor.

By forming the charge generation layer 305 with any of the above materials, it is possible to suppress an increase in drive voltage caused when the EL layers are stacked.

Although the light-emitting element having two EL layers is described in this embodiment, a light-emitting element in which three or more EL layers are stacked can also be used. When a plurality of EL layers with a charge generation layer interposed therebetween are arranged between a pair of electrodes, as in the light-emitting element of this embodiment, light emission in a high luminance region can be obtained. Thus, current density can be kept low, and an element having a long lifetime can be realized.

Since a voltage drop due to the resistance of an electrode material can be reduced by using this embodiment as described above, uniform light emission in a large area can be obtained. Moreover, owing to the capability of low-voltage driving, a light-emitting device with low power consumption can be realized.

Furthermore, by making the emission colors of the EL layers different, light emission with a desired color can be obtained. For example, white light emission can be obtained by a mixture of lights emitted from the first and second EL layers whose emission colors are made complementary colors, as in Embodiment 2.

Note that the structure described in this embodiment can be combined with any of the structures described in Embodiments 1 to 3 as appropriate.

(Embodiment 5)

In Embodiment 5, as one embodiment of the present invention, one mode of a light-emitting element in which an organometallic complex is used as a sensitizer will be described with reference to FIG. 1.

FIG. 1 illustrates the light-emitting element in which the EL layer 102 including the light-emitting layer 113 is interposed between the first electrode 101 and the second electrode 103. The light-emitting layer 113 includes any of the organometallic complexes which are embodiments of the present invention and a fluorescent compound that can emit light having a longer wavelength than light emitted from this organometallic complex.

In such a light-emitting element, holes injected from the first electrode 101 and electrons injected from the second electrode 103 side recombine in the light-emitting layer 113 to raise the fluorescent compound to an excited state. When the fluorescent compound in the excited state returns to the ground state, light is emitted. At this time, the organometallic complex which is one embodiment of the present invention acts as a sensitizer for the fluorescent compound, and increases the number of fluorescent compound molecules in a singlet excited state. With use of the organometallic complex of the present invention as a sensitizer in this manner, a light-emitting element having high emission efficiency can be obtained. Note that in the light-emitting element of Embodiment 5, the first electrode 101 functions as an anode and the second electrode 103 function as a cathode.

The light-emitting layer 113 includes the organometallic complex which is one embodiment of the present invention and the fluorescent compound that can emit light having a longer wavelength than light emitted from this organometallic complex. Preferably, the organometallic complex and the fluorescent compound are dispersed as guests in a substance used as a host material which has higher singlet excitation energy than that of the fluorescent substance as well as higher triplet excitation energy than that of the organometallic complex.

Note that there is no particular limitation on the substance (i.e. host material) used to disperse the organometallic complex and the fluorescent compound, and the substances given as examples of the host material in Embodiment 2, or the like can be used.

Although there is also no particular limitation on the fluorescent compound, preferable examples thereof are compounds which can emit red light to infrared light such as 4-dicyanomethylene-2-isopropyl-6-[2-(1,1,7,7-tetramethyljulolidin-9-yl)ethenyl]-4H-pyran (abbreviation: DCJTI), magnesium phthalocyanine, magnesium porphyrin, phthalocyanine and the like.

Note that the first electrode 101 described in Embodiment 5 can have the same structure as the first electrode described in Embodiment 2 and the second electrode 103 in this embodiment can have the same structure as the second electrode described in Embodiment 2.

Further, the hole-injection layer 111, the hole-transport layer 112, the electron-transport layer 114, and the electron-injection layer 115 are provided as illustrated in FIG. 1 in Embodiment 5, and as for structures of these layers, the structures of the respective layers described in Embodiment 2 can be applied. However, these layers are not necessarily needed, and can be provided as appropriate depending on element characteristics.

As described above, according to Embodiment 5, any of the organometallic complexes which are embodiments of the present invention can each be used as a sensitizer so that light emission with high efficiency can be obtained.

Note that the structure described in Embodiment 5 can be combined with any of the structures described in Embodiments 1 to 4 as appropriate.

(Embodiment 6)

In Embodiment 6, as one embodiment of the present invention, a passive matrix light-emitting device and an active matrix light-emitting device each of which is a light-emitting device fabricated using a light-emitting element will be described.

Examples of the passive matrix light-emitting device are illustrated in FIGS. 4A to 4D and FIG. 5.

In the passive matrix (also called simple matrix) light-emitting device, a plurality of anodes arranged in stripes (in stripe form) is provided to intersect at right angles with a plurality of cathodes arranged in stripes. At intersections of the anodes and the cathodes, a light-emitting layer is interposed. Thus, light is emitted from a pixel at the intersection of an anode which is selected (to which a voltage is applied) and a cathode which is selected.

Figure 4A:
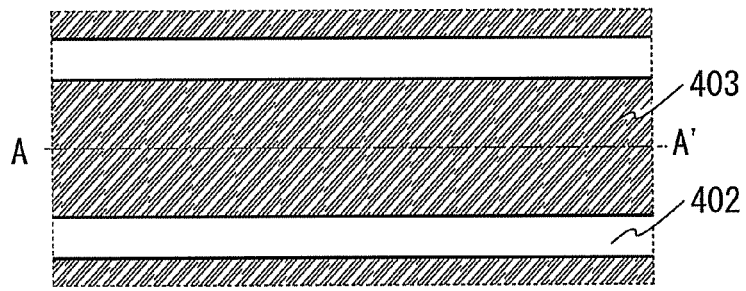
FIGS. 4A to 4D illustrate a passive matrix light-emitting device.
Figure 4B:
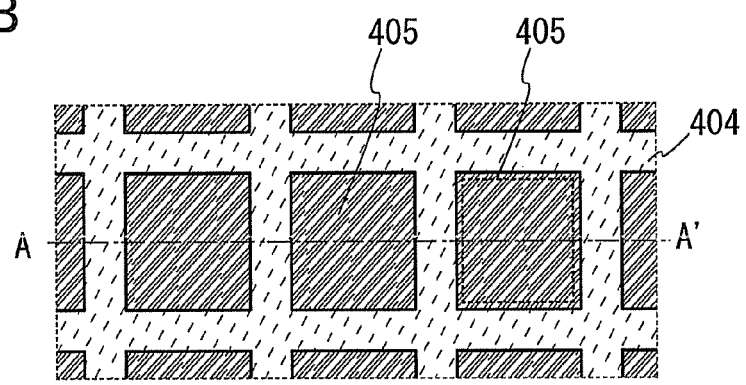
Figure 4C:
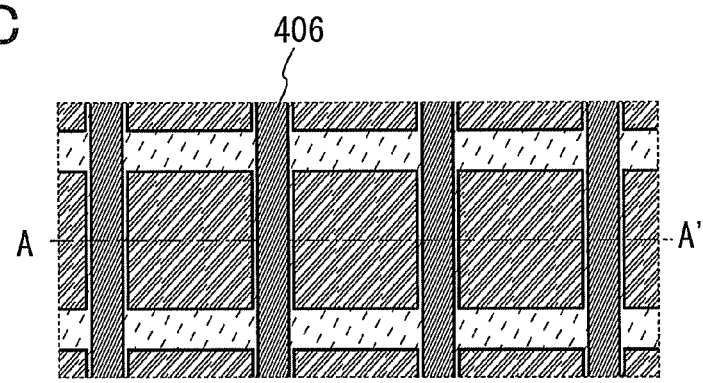
Figure 4D:
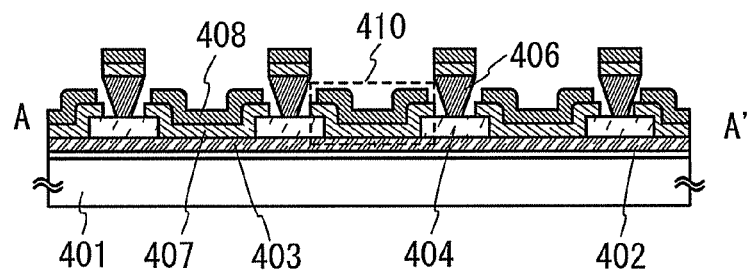

FIGS. 4A to 4C are top views of a pixel portion before sealing, and FIG. 4D is a cross-sectional view taken along a dashed line A-A' in FIG. 4C.

First, over a substrate 401, an insulating layer 402 is formed as a base insulating layer. Note that the base insulating layer 402 is not necessarily formed if not needed. Over the insulating layer 402, a plurality of first electrodes 403 is arranged in stripes at regular intervals (see FIG. 4A).

Next, a first partition 404 having openings each corresponding to a pixel is provided over the first electrodes 403. Note that the first partition 404 having the openings is formed of an insulating material (a photosensitive or nonphotosensitive organic material (e.g., polyimide, acrylic, polyamide, polyimide amide, resist, or benzocyclobutene) or an SOG film (e.g., a $SiO_x$ film containing an alkyl group). Note that openings corresponding to the pixels serve as light-emitting regions 405 (see FIG. 4B).

Next, over the first partition 404 having the openings, a plurality of second partitions 406 which are reversely tapered and parallel to each other is provided to intersect with the first electrodes 403 (see FIG. 4C). The second partitions 406 which are reversely tapered are formed by a photolithography method.

After the second partitions 406 which are reversely tapered are formed as illustrated in FIG. 4C, an EL layer 407 and a second electrode 408 are sequentially formed as illustrated in FIG. 4D. Note that the sum of the heights of the first partition 404 having the openings and the second partition 406 which is reversely tapered is set to exceed the sum of the thicknesses of the EL layer 407 and the second electrode 408. Consequently, as illustrated in FIG. 4D, a plurality of divided regions each including the EL layer 407 and the second electrode 408 is formed. Note that the plurality of divided regions 410 is electrically isolated from one another.

The second electrodes 408 are electrodes that extend in the direction in which they intersect with the first electrodes 403 and that are arranged in stripes to be parallel to one another. Although a part of a material for forming the EL layer 407 and a part of a conductive layer for forming the second electrode 408 are formed even over the second partition 406 which is reversely tapered, these parts are electrically isolated from the divided regions 410.

Note that there is no limitation on the first electrode 403 and the second electrode 408 in this embodiment as far as one of them is an anode and the other is a cathode. Further, the stack structure of the EL layer 407 can be adjusted as appropriate depending on the polarities of the electrodes.

Further, if necessary, a sealing material such as a sealing can or a glass substrate may be attached to the substrate 401 to perform sealing with an adhesive such as a sealant so that a light-emitting element is placed in the sealed space. This can prevents deterioration of the light-emitting element. Note that the sealed space may be filled with a filler or a dry inert gas. Further, a desiccant or the like is put between the substrate and the sealing material to prevent deterioration of the light-emitting element due to moisture or the like, and accordingly, the desiccant removes a minute amount of moisture to perform sufficient desiccation. Note that the desiccant can be a substance that absorbs moisture by chemical adsorption, such as an oxide of an alkaline-earth metal typified by calcium oxide or barium oxide. As a desiccant other than the above, a substance that adsorbs moisture by physical adsorption, such as zeolite or silica gel, may be used.

Figure 5:
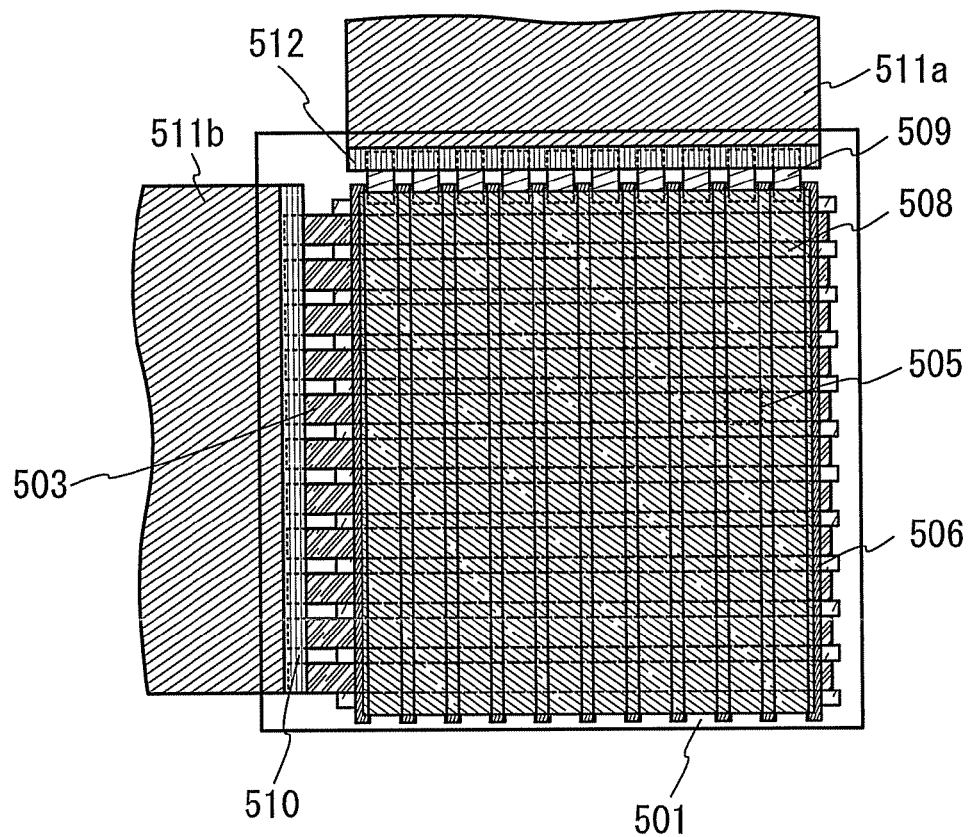
FIG. 5 illustrates a passive matrix light-emitting device.

FIG. 5 is a top view of the passive matrix light-emitting device using a structure illustrated in FIG. 4D, on which an FPC and the like are mounted.

In FIG. 5, scan lines and data lines intersect at right angles in the pixel portion (corresponding to the light-emitting region in FIG. 4B) for displaying images.

Here, the first electrode 403 in FIGS. 4A to 4D corresponds to a scan line 503 in FIG. 5, the second electrode 408 in FIGS. 4A to 4D corresponds to a data line 508 in FIG. 5, and the second partition 406 which is reversely tapered corresponds to a second partition 506. The EL layer 407 in FIGS. 4A to 4D is interposed between the data lines 508 and the scan lines 503, and an intersection indicated as a region 505 corresponds to one pixel.

Note that the data lines 508 are electrically connected at their ends to connection wirings 509, and the connection wirings 509 are connected to an FPC 511*a* via an input terminal 512. In addition, the scan lines 503 are connected to an FPC 511*b* via an input terminal 510.

If necessary, an optical film such a polarizing plate, a circularly polarizing plate (including an elliptically polarizing plate), a retardation plate (a quarter-wave plate or a half-wave plate) or a color filter, or a micro lens array may be provided as appropriate on the emission side. Note that the polarizing plate or the circularly polarizing plate may be provided with an anti-reflection film. For example, projections and depressions are provided on a surface of the emission side to diffuse reflected light caused by light entering the emission side from the outside of the light-emitting device so that glare can be reduced (also referred to as an anti-glare treatment). Further, devising the form of the projections and depressions provided on a surface of the emission side (e.g., regular arrangement of hemicycle lenses) can enhance the efficiency of light extraction from the light-emitting layer to the outside (so-called light extraction efficiency).

Note that, although FIG. 5 illustrates an example in which a driver circuit is not provided over the substrate 501, an IC chip including a driver circuit may be mounted on the substrate 501.

When the IC chip is mounted, in the peripheral (outside) region of the pixel portion, ICs, in which a driver circuit for transmitting a signal to the pixel portion is formed, are mounted on the data line side and/or the scan line side by a COG method. As the mounting technique other than the COG method, a TCP or a wire bonding method may be used. The TCP is obtained by mounting an IC on a TAB tape in such a way that the TAB tape is connected to a wiring over an element formation substrate and the IC is mounted. The ICs on the data line side and the scan line side may be formed using a silicon substrate, or may be obtained by formation of a driver circuit with a TFT over a glass substrate, a quartz substrate, or a plastic substrate.

Figure 6A:
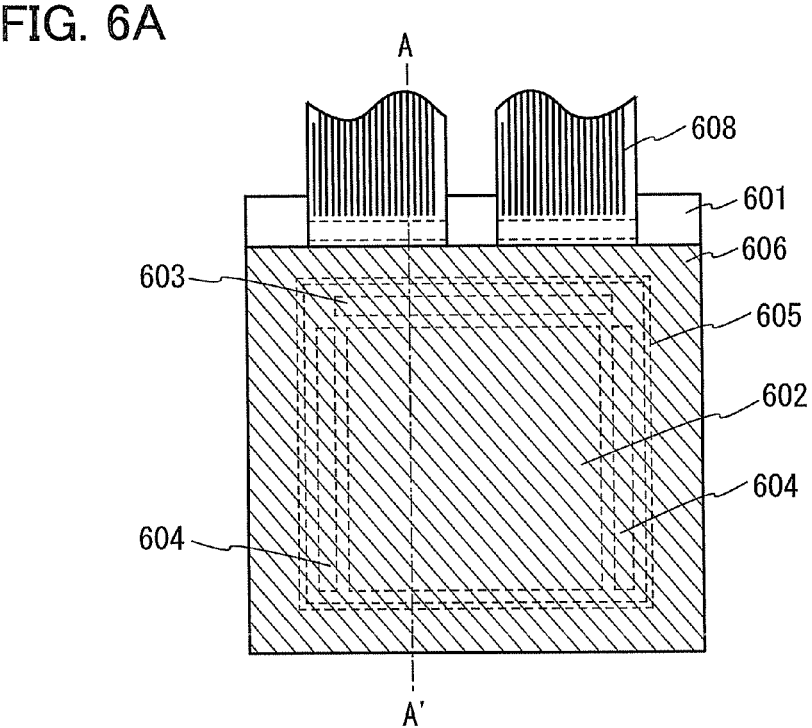
FIGS. 6A and 6B illustrate an active matrix light-emitting device.
Figure 6B:
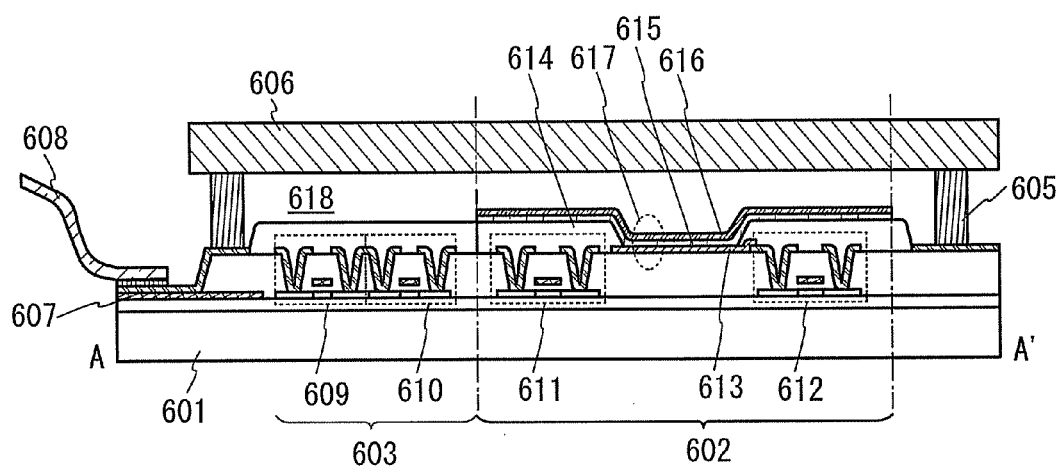

Next, an example of the active matrix light-emitting device will be described with reference to FIGS. 6A and 6B. Note that FIG. 6A is a top view illustrating the light-emitting device and FIG. 6B is a cross-sectional view taken along an alternate long and short dashed line A-A' in FIG. 6A. The active matrix light-emitting device according to this embodiment includes a pixel portion 602 provided over an element substrate 601, a driver circuit portion (source side driver circuit) 603, and a driver circuit portion (gate side driver circuit) 604. The pixel portion 602, the driver circuit portion (source side driver circuit) 603, and the driver circuit portion (gate side driver circuit) 604 are sealed between the element substrate 601 and the sealing substrate 606 by the sealing material 605.

Note that FIG. 6B, which is a cross-sectional view taken along the alternate long and short dashed line A-A', illustrates only part of the cross section of the pixel portion 602 and part of the driver circuit portion (source side driver circuit) 603, because the whole of the cross sections are difficult to illustrate.

In addition, over the element substrate 601, a lead wiring 607 for connecting an external input terminal, through which a signal (e.g., a video signal, a clock signal, a start signal, and a reset signal) or a potential from the outside is transmitted to the driver circuit portion (source side driver circuit) 603 and the driver circuit portion (gate side driver circuit) 604, is provided. Here, an example in which an FPC (flexible printed circuit) 608 is provided as the external input terminal is described. Although only the FPC is illustrated here, a printed wiring board (PWB) may be attached to this FPC. The light-emitting device in this specification includes not only a light-emitting device itself but also a light-emitting device provided with an FPC or a PWB.

Next, a cross-sectional structure of the light-emitting device will be described with reference to FIG. 6B. The driver circuit portion and the pixel portion are formed over the element substrate 601, and here the driver circuit portion (source side driver circuit) 603 and the pixel portion 602 are illustrated.

The driver circuit portion (source side driver circuit) 603 is an example where a CMOS circuit, which is a combination of an n-channel TFT 609 and a p-channel TFT 610, is formed. Note that the driver circuit portion may be formed with any of a variety of circuits such as a CMOS circuit, a PMOS circuit, or an NMOS circuit. Although a driver integrated type in which the driver circuit is formed over the substrate is illustrated in this embodiment, the driver circuit may not necessarily be formed over the substrate, and the driver circuit can be formed outside, not over the substrate.

The pixel portion 602 includes a plurality of pixels each of which includes a switching TFT 611, a current control TFT 612, and an anode 613 electrically connected to a wiring (a source electrode or a drain electrode) of the current control TFT 612. Note that an insulator 614 is formed to cover an end portion of the anode 613. Here, the insulator 614 is formed using a positive photosensitive acrylic resin.

The insulator 614 is preferably foamed so as to have a curved surface with curvature at an upper end portion or a lower end portion thereof in order to obtain favorable coverage by a film which is to be stacked over the anode 613 and the insulator 614. For example, in the case where a positive photosensitive acrylic resin is used as a material of the insulator 614, the insulator 614 is preferably formed so as to have a curved surface with a curvature radius (0.2 μm to 3 μm) at the upper end portion. Note that, for the insulator 614, either a negative photosensitive material that becomes insoluble in an etchant by light or a positive photosensitive material that becomes soluble in an etchant by light can be used, or an inorganic compound such as silicon oxide or silicon oxynitride can be used in addition to an organic compound.

An EL layer 615 and a cathode 616 are stacked over the anode 613. Note that when an ITO film is used as the anode 613, and a stacked film of a titanium nitride film and a film containing aluminum as its main component or a stacked film of a titanium nitride film, a film containing aluminum as its main component, and a titanium nitride film is used as the wiring of the current controlling TFT 612 which is connected to the anode 613, resistance as a wiring is low and favorable ohmic contact with the ITO film can be obtained. Note that, although not illustrated here, the cathode 616 is electrically connected to the FPC (flexible printed circuit) 608 which is an external input terminal.

It is preferable that in the EL layer 615, at least a light-emitting layer be provided, and in addition to the light-emitting layer, a hole-injection layer, a hole-transport layer, an electron-transport layer, and an electron-injection layer be provided as appropriate. A light-emitting element 617 has a stacked structure of the anode 613, the EL layer 615, and the cathode 616.

Although the cross-sectional view in FIG. 6B illustrates only one light-emitting element 617, a plurality of light-emitting elements is preferably arranged in matrix in the pixel portion 602. Light-emitting elements which emit three-color (R, G, and B) light are selectively formed in the pixel portion 602, so that a light-emitting device capable of full color display can be formed. Alternatively, a light-emitting device capable of full color display may be obtained in such a way that a light-emitting element that emits single-color light is formed in the pixel portion 602 and combined with a color filter.

Further, the sealing substrate 606 is attached to the element substrate 601 with the sealing material 605, so that the light-emitting element 617 is provided in a space 618 enclosed by the element substrate 601, the sealing substrate 606, and the sealing material 605. The space 618 may be filled with an inert gas (such as nitrogen or argon), or the sealing material 605.

Note that an epoxy-based resin is preferably used as the sealing material 605. Such a material preferably allows as little moisture and oxygen as possible to penetrate. As a material used for the sealing substrate 606, a plastic substrate formed of FRP (fiberglass-reinforced plastics), PVF (polyvinyl fluoride), polyester, acrylic, or the like can be used other than a glass substrate or a quartz substrate.

By using this embodiment, the light-emitting device can include a phosphorescent light-emitting element having high emission efficiency according to the present invention as described above; therefore, the power consumption of the light-emitting device can be reduced and the luminance thereof can be increased.

Furthermore, when a light-emitting element using any of the organometallic complexes which are embodiments of the present invention and emit yellow phosphorescence with high luminance is added to a pixel having elements emitting red light, green light, and blue light as sub-pixels to form a pixel including sub-pixels for four colors, red, green, blue, and yellow, a light-emitting device having excellent characteristics such as brilliant image display and high visibility can be provided.

Note that the structure described in this embodiment can be combined with any of the structures described in Embodiments 1 to 5 as appropriate.

(Embodiment 7)

In Embodiment 7, with reference to FIGS. 7A to 7E, FIG. 8, and FIGS. 9A and 9B, description is given of examples of a variety of electronic devices and lighting devices that are completed by using the light-emitting device according to one embodiment of the present invention.

Examples of the electronic devices to which the light-emitting device is applied are television devices (also referred to as TV or television receivers), monitors for computers and the like, cameras such as digital cameras and digital video cameras, digital photo frames, cellular phones (also referred to as portable telephone devices), portable game machines, portable information terminals, audio playback devices, large game machines such as pin-ball machines, and the like. Specific examples of these electronic devices and a lighting device are illustrated in FIGS. 7A to 7E.

Figure 7A:
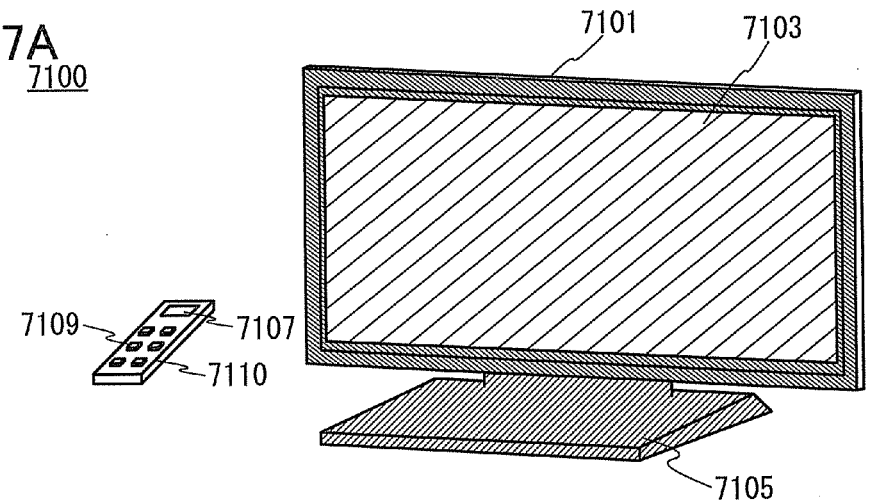
FIGS. 7A to 7E illustrate electronic devices.

FIG. 7A illustrates an example of a television device. In the television device 7100, a display portion 7103 is incorporated into a housing 7101. The display portion 7103 is capable of displaying images, and the light-emitting device can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the receiver, general television broadcasting can be received. Furthermore, when the television device 7100 is connected to a communication network by wired or wireless connection via the modem, one-way (from a transmitter to a receiver) or two-way (between a transmitter and a receiver, between receivers, or the like) data communication can be performed.

Figure 7B:
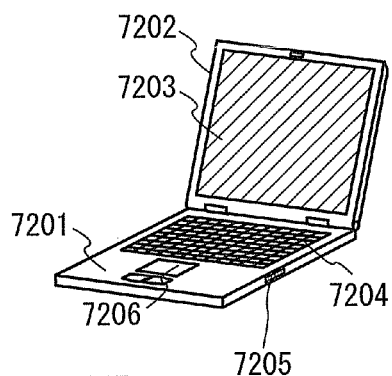

FIG. 7B illustrates a computer 7200 having a main body 7201, a housing 7202, a display portion 7203, a keyboard 7204, an external connecting port 7205, a pointing device 7206, and the like. This computer is manufactured by using the light-emitting device for the display portion 7203.

Figure 7C:
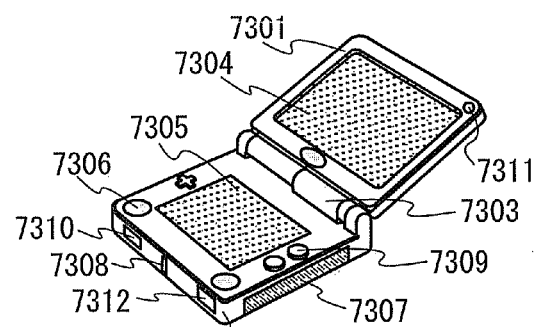

FIG. 7C illustrates a portable game machine 7300 having two housings, a housing 7301 and a housing 7302, which are connected with a joint portion 7303 so that the portable game machine can be opened or folded. A display portion 7304 is incorporated into the housing 7301 and a display portion 7305 is incorporated into the housing 7302. In addition, the portable game machine illustrated in FIG. 7C includes a speaker portion 7306, a recording medium insertion portion 7307, an LED lamp 7308, an input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), or a microphone 7312), and the like. It is needless to say that the structure of the portable games machine is not limited to the above as far as the light-emitting device can be used for at least either the display portion 7304 or the display portion 7305, or both, and may include other accessories arbitrarily. The portable game machine illustrated in FIG. 7C has a function of reading out a program or data stored in a storage medium to display it on the display portion, and a function of sharing information with another portable game machine by wireless communication. The portable game machine illustrated in FIG. 7C can have a variety of functions without limitation to the above.

Figure 7D:
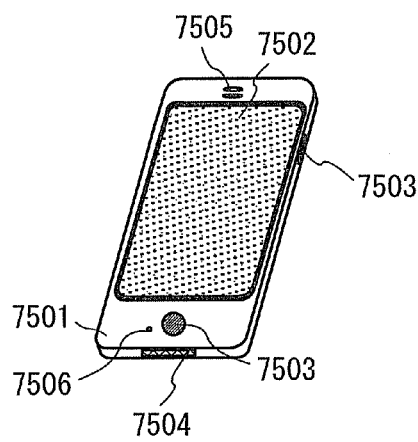

FIG. 7D illustrates an example of a cellular phone. The cellular phone 7400 is provided with operation buttons 7403, an external connection port 7404, a speaker 7405, a microphone 7406, and the like, in addition to a display portion 7402 incorporated into a housing 7401. Note that the cellular phone 7400 is manufactured using the light-emitting device for the display portion 7402.

When the display portion 7402 of the cellular phone 7400 illustrated in FIG. 7D is touched with a finger or the like, data can be input into the cellular phone 7400. Further, operations such as making a call and creating e-mail can be performed by touch on the display portion 7402 with a finger or the like.

There are mainly three screen modes of the display portion 7402. The first mode is a display mode mainly for displaying an image. The second mode is an input mode mainly for inputting information such as characters. The third mode is a display-and-input mode in which two modes of the display mode and the input mode are mixed.

For example, in the case of making a call or creating e-mail, a text input mode mainly for inputting text is selected for the display portion 7402 so that text displayed on a screen can be input. In this case, it is preferable to display a keyboard or number buttons on almost the entire screen of the display portion 7402.

When a detection device including a sensor for detecting inclination, such as a gyroscope or an acceleration sensor, is provided inside the cellular phone 7400, display on the screen of the display portion 7402 can be automatically changed by determining the orientation of the cellular phone 7400 (whether the cellular phone is placed horizontally or vertically for a landscape mode or a portrait mode).

The screen modes are switched by touch on the display portion 7402 or operation with the operation buttons 7403 of the housing 7401. Alternatively, the screen modes can be switched depending on kinds of images displayed on the display portion 7402. For example, when a signal for an image displayed on the display portion is data of moving images, the screen mode is switched to the display mode. When the signal is text data, the screen mode is switched to the input mode.

Moreover, in the input mode, if a signal detected by an optical sensor in the display portion 7402 is detected and the input by touch on the display portion 7402 is not performed during a certain period, the screen mode may be controlled so as to be switched from the input mode to the display mode.

The display portion 7402 can function as an image sensor. For example, an image of a palm print, a fingerprint, or the like is taken by touch on the display portion 7402 with the palm or the finger, so that personal authentication can be performed. Furthermore, by provision of a backlight or a sensing light source emitting a near-infrared light for the display portion, an image of a finger vein, a palm vein, or the like can also be taken.

Figure 7E:
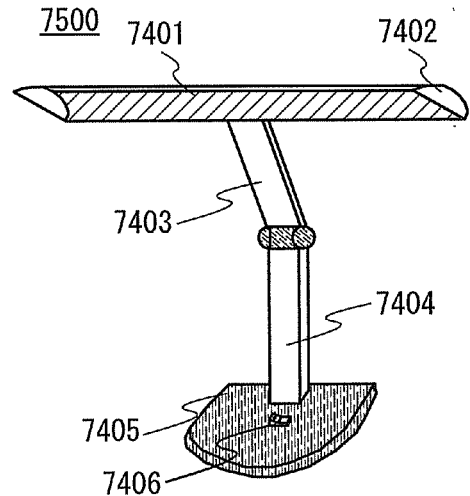

FIG. 7E illustrates a desk lamp 7500 including a lighting portion 7501, a shade 7502, an adjustable arm 7503, a support 7504, a base 7505, and a power switch 7506. The desk lamp is manufactured using the light-emitting device for the lighting portion 7501. Note that the "lighting device" also encompasses ceiling lights, wall lights, and the like.

Figure 8:
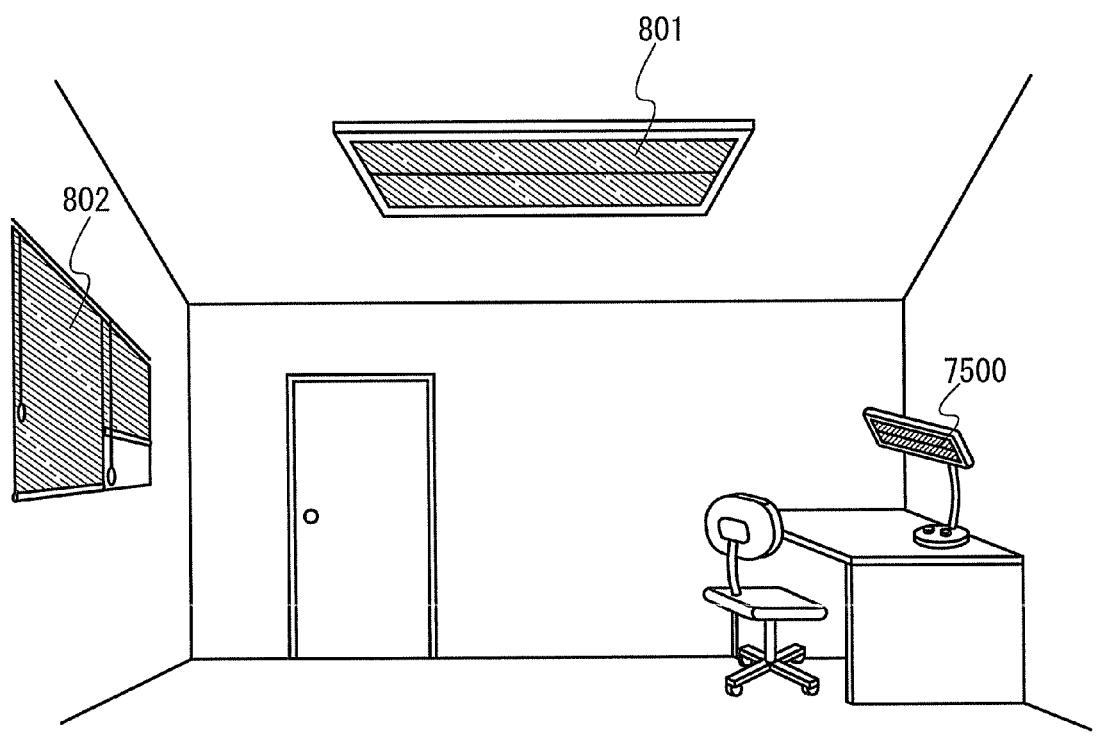
FIG. 8 illustrates lighting devices.

FIG. 8 illustrates an example in which the light-emitting device is used for an interior lighting device 801. Since the light-emitting device can have a larger area, it can be used as a lighting device having a large area. Furthermore, the light-emitting device can be used as a roll-type lighting device 802. As illustrated in FIG. 8, the desk lamp 7500 described with reference to FIG. 7E may be used together in a room provided with the interior lighting device 801.

As described above, with the light-emitting device provided with the light-emitting element according to the present invention, an electronic device or a lighting device each having high added value such as lower power consumption, higher luminance, brilliant image display, and excellent visibility can be obtained. The application range of the light-emitting device is wide so that the light-emitting device can be applied to electronic devices and lighting devices in a variety of fields.

Note that the structure described in this embodiment can be combined with any of the structures described in Embodiments 1 to 6 as appropriate.

(Embodiment 8)

Figure 9A:
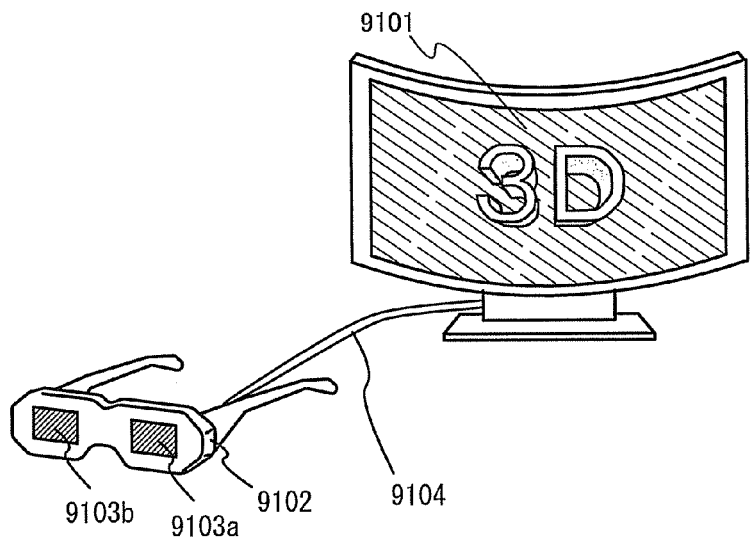
FIGS. 9A and 9B illustrate an electronic apparatus.
Figure 9B:
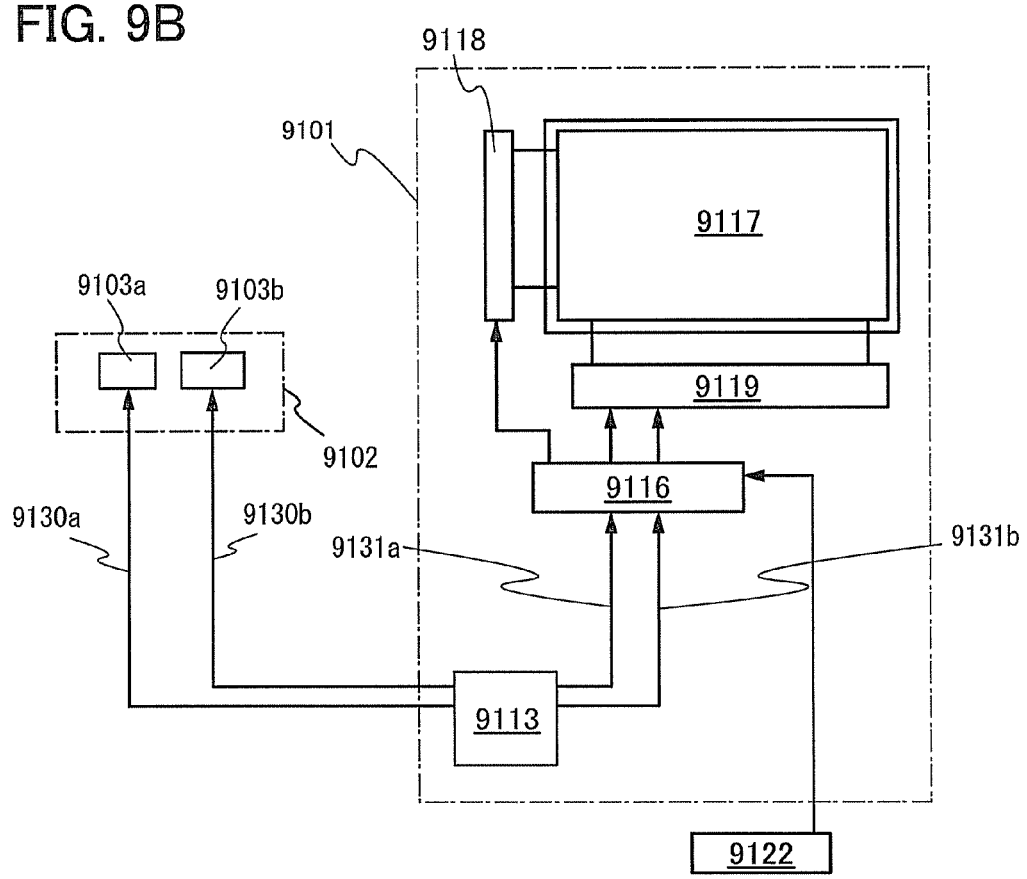

Referring to FIGS. 9A and 9B, this embodiment shows an example in which a display device that switches between an image for a left eye and an image for a right eye at high speed is used for visual recognition of a 3D image, which is a moving image or a still image, using dedicated glasses with which videos of the display device are synchronized.

FIG. 9A illustrates the appearance of a 3D image display device 9100, and a display portion 9101 and dedicated glasses 9102 are connected with a cable 9104. In the dedicated glasses 9102, shutters provided in a panel 9103a for a left eye and a panel 9103b for a right eye are alternately opened and closed; thus, an image displayed on the display portion 9101 can be seen as a 3D image by a user.

In addition, FIG. 9B is a block diagram illustrating a main structure of the display portion 9101 and the dedicated glasses 9102.

The display portion 9101 illustrated in FIG. 9B includes a display control circuit 9116, a display portion 9117, a timing generator 9113, a source line driver circuit 9118, an external operation unit 9122, and a gate line driver circuit 9119. A highly efficient light-emitting element using any of the organometallic complexes according to the present invention can be used for the display portion 9117. Note that an output signal changes in accordance with operation by the external operation unit 9122 such as a keyboard.

In the timing generator 9113, a start pulse signal and the like are formed, and a signal for synchronizing an image for a left eye and the shutter of the panel 9103a for a left eye, a signal for synchronizing an image for a right eye and the shutter of the panel 9103b for a right eye, and the like are formed.

A synchronization signal 9131a of the image for a left eye is input to the display control circuit 9116, so that the image for a left eye is displayed on the display portion 9117. At the same time, a synchronization signal 9130a for opening the shutter of the panel 9103a for a left eye is input to the panel 9103a for a left eye. In addition, a synchronization signal 9131b of the image for a right eye is input to the display control circuit 9116, so that the image for a right eye is displayed on the display portion 9117. At the same time, a synchronization signal 9130b for opening the shutter of the panel 9103b for a right eye is input to the panel 9103b for a right eye.

Further, since a field sequential method is employed, it is preferable that the timing generator 9113 input signals synchronized with the synchronization signals 9130a and 9130b to light-emitting elements as well.

According to this embodiment, a displayed image with higher luminance can be realized as described above, leading to suppression of the darkness of a screen which is one of the problems with 3D image display devices. Further, inclusion of the light-emitting element according to the present invention enables the response speed of each pixel to be greatly increased, leading to suppression of crosstalk generation which is one of the problems with 3D image display devices. Furthermore, the power consumption of 3D image display devices can also be reduced.

Note that this embodiment can be combined with any of the other embodiments described in this specification, as appropriate.

EXAMPLE 1

Synthesis Example 1

Example 1 gives a specific example of the synthesis of the organometallic complex represented by the structural formula (100) in Embodiment 1 which is one embodiment of the present invention, (acetylacetonato)bis[3,5-dimethyl-2-(4-phenoxyphenyl)pyrazinato]iridium(III) (abbreviation: [Ir(dmpoppr)₂(acac)]). A structure of [Ir(dmpoppr)₂(acac)] is illustrated below.

[Chemical formula 52]

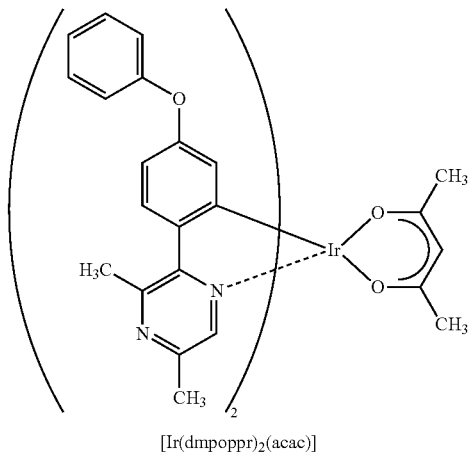

[Ir(dmpoppr)₂(acac)]

Step 1: Synthesis of
3,5-Dimethyl-2-(4-phenoxyphenyl)pyrazine
(abbreviation: Hdmpoppr)

First, into a recovery flask equipped with a reflux pipe were placed 1.35 g of 2-chloro-3,5-dimethylpyrazine, 2.02 g of 4-phenoxyphenylboronic acid, 1.00 g of sodium carbonate, 0.043 g of bis(triphenylphosphine)palladium(II)dichloride (abbreviation: Pd(PPh₃)₂Cl₂), 15 mL of water, and 15 mL of acetonitrile, and the air inside the flask was replaced with argon. Heating was performed by microwave irradiation (2.45 GHz, 100 W) of this reaction container for 10 minutes, so that reaction occurred. After that, water was added to this reaction solution, and extraction with dichloromethane was carried out. A solution of the obtained extract was washed with water and dried over magnesium sulfate. After the drying, the solution was filtered. After the solvent of this solution was distilled, the obtained residue was washed with methanol, so that the pyrazine derivative which was the object of the synthesis, Hdmpoppr, was obtained (a white powder in a yield of 89%). Note that a microwave synthesis system (Discover, produced by CEM Corporation) was used for the microwave irradiation. The synthesis scheme of Step 1 is illustrated in the following formulae (e).

[Chemical formulae 53]

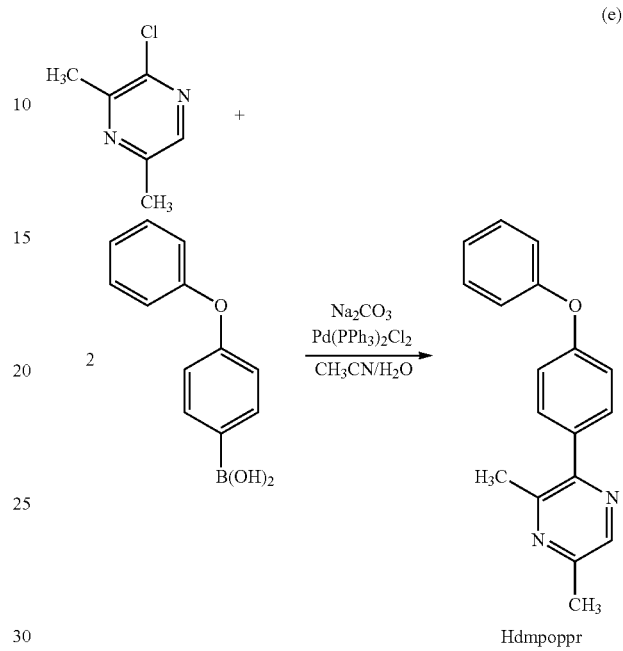

(e)

Step 2: Synthesis of Di-μ-chloro-bis[bis{3,5-dimethyl-2-(4-phenoxyphenyl)pyrazinato}iridium(III)] (abbreviation: [Ir(dmpoppr)₂Cl]₂)

Next, into a recovery flask equipped with a reflux pipe were placed 9 mL of 2-ethoxyethanol, 3 mL of water, 0.91 g of Hdmpoppr obtained in Step 1 above, and 0.45 g of iridium chloride hydrate (IrCl₃.H₂O), and the air in the flask was replaced with argon. Microwave irradiation (2.45 GHz, 100 W) was performed for 30 minutes, so that reaction occurred. The powder precipitated from the reaction solution was subjected to filtration and washed with ethanol to give a binuclear complex, [Ir(dmpoppr)₂Cl]₂ (a brown powder in a yield of 80%). The synthesis scheme of Step 2 is illustrated in the following formulae (f).

[Chemical formulae 54]

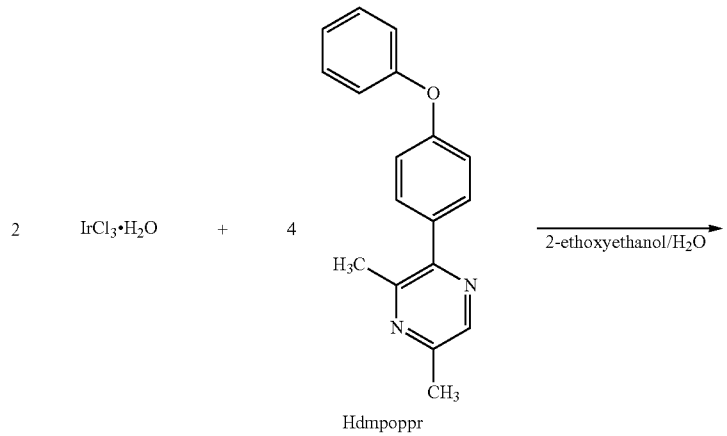

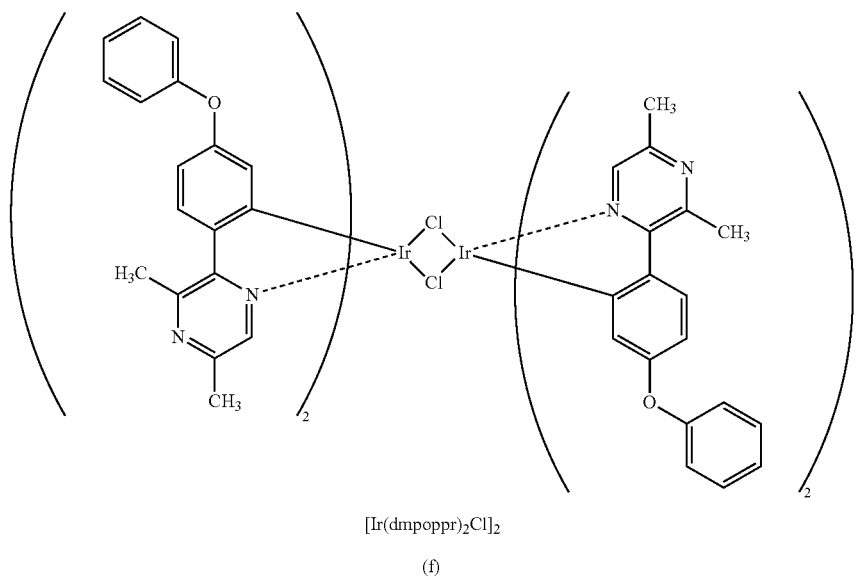

[Ir(dmpoppr)₂Cl]₂

(f)

Step 3: Synthesis of (Acetylacetonato)bis[3,5-dimethyl-2-(4-phenoxyphenyl)pyrazinato]iridium(III) (abbreviation: [Ir(dmpoppr)₂(acac)])

Furthermore, into a recovery flask equipped with a reflux pipe were placed 10 mL of 2-ethoxyethanol, 0.94 g of the binuclear complex obtained in Step 2 above, [Ir(dmpoppr)₂Cl]₂, 0.19 mL of acetylacetone, and 0.64 g of sodium carbonate, and the air in the flask was replaced with argon. After that, microwave irradiation (2.45 GHz, 100 W) was performed for 30 minutes, so that reaction occurred. The powder precipitated from the reaction solution was subjected to filtration and washed with ethanol, and then was dissolved in dichloromethane. This solution was filtered to remove an insoluble portion and concentrated. The obtained residue was recrystallized from a mixed solvent of dichloromethane and methanol, so that one of the organometallic complexes according to the present invention, [Ir(dmpoppr)₂(acac)], was obtained (an orange powder in a yield of 56%). The synthesis scheme of Step 3 is illustrated in the following formulae (h).

[Chemical formulae 55]

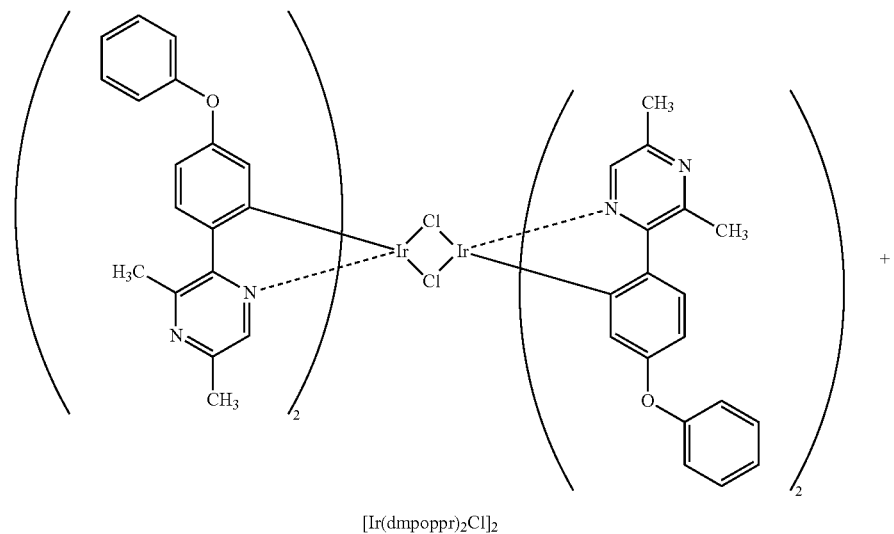

[Ir(dmpoppr)₂Cl]₂

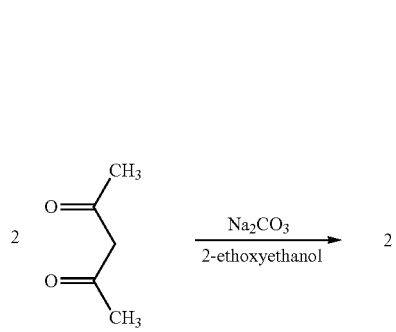 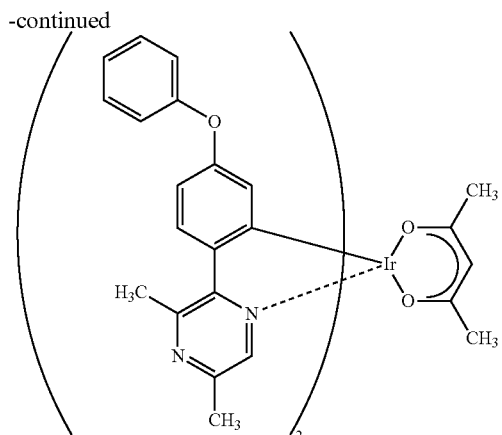

[Ir(dmpoppr)₂(acac)]

(g)

Figure 10:
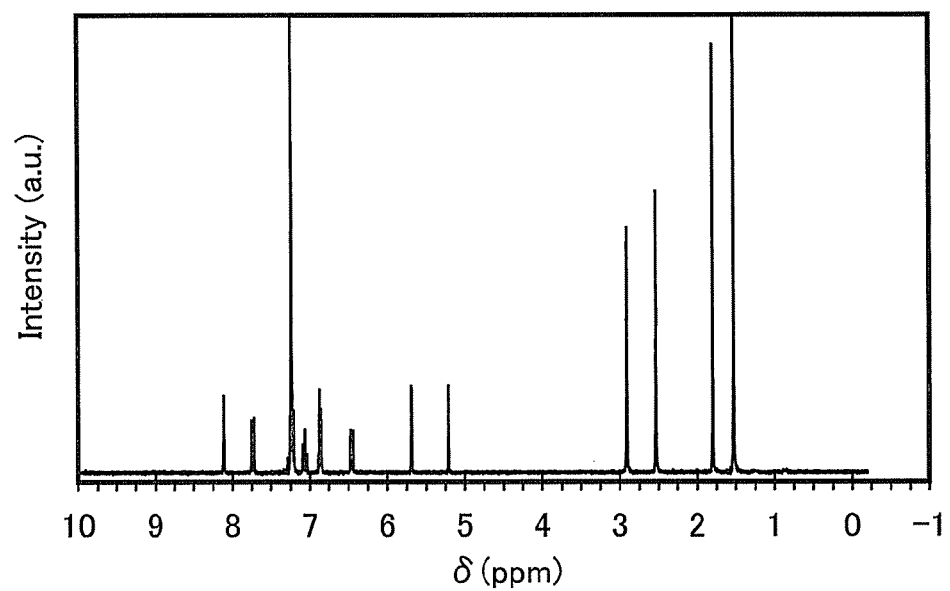
FIG. 10 shows a $^1$H NMR chart of an organometallic complex represented by a structural formula (100).

The results of the nuclear magnetic resonance (¹H NMR) spectroscopy, by which the orange powder obtained in Step 3 above was analyzed, are shown below. In addition, a ¹H-NMR chart is shown in FIG. 10. These results revealed that the organometallic complex represented by the above-described structural formula (100) which is one embodiment of the present invention, [Ir(dmpoppr)₂(acac)], was obtained in Synthesis Example 1.

¹H-NMR. δ (CDCl₃): 1.80 (s, 6H), 2.53 (s, 6H), 2.91 (s, 6H), 5.21 (s, 1H), 5.69 (d, 2H), 6.46 (dd, 2H), 6.87 (m, 4H), 7.07 (t, 2H), 7.21 (m, 4H), 7.74 (d, 2H), 8.11 (s, 2H).

Figure 11:
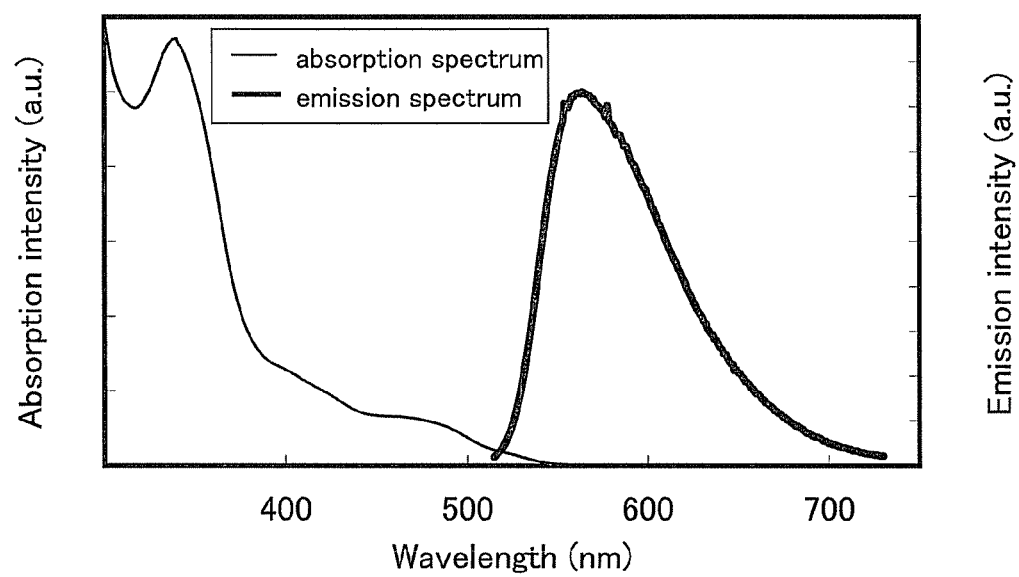
FIG. 11 shows an ultraviolet-visible absorption and emission spectra of an organometallic complex represented by a structural formula (100).

Next, an ultraviolet-visible absorption spectrum (hereinafter, simply referred to as an "absorption spectrum") of a dichloromethane solution of [Ir(dmpoppr)₂(acac)] and an emission spectrum thereof were measured. The measurement of the absorption spectrum was conducted at room temperature, for which an ultraviolet-visible light spectrophotometer (V550 type manufactured by Japan Spectroscopy Corporation) was used and the dichloromethane solution (0.053 mmol/L) was put in a quartz cell. In addition, the measurement of the emission spectrum was conducted at room temperature, for which a fluorescence spectrophotometer (FS920 manufactured by Hamamatsu Photonics Corporation) was used and the degassed dichloromethane solution (0.32 mmol/L) was put in a quartz cell. Measurement results of the obtained absorption and emission spectra are shown in FIG. 11, in which the horizontal axis represents wavelength and the vertical axis represents absorption intensity and emission intensity. In FIG. 11 where there are two solid lines, the thin line represents the absorption spectrum and the thick line represents the emission spectrum. Note that the absorption spectrum in FIG. 11 is the results obtained in such a way that the absorption spectrum measured by putting only dichloromethane in a quartz cell was subtracted from the absorption spectrum measured by putting the dichloromethane solution (0.053 mmol/L) in a quartz cell.

As shown in FIG. 11, the organometallic complex of one embodiment of the present invention, [Ir(dmpoppr)₂(acac)], has an emission peak at 564 nm, and yellow light emission was observed from the dichloromethane solution.

EXAMPLE 2

Synthesis Example 2

Example 2 gives a specific example of the synthesis of the organometallic complex represented by the structural formula (130) in Embodiment 1 which is one embodiment of the present invention, tris[3,5-dimethyl-2-(4-phenoxyphenyl)pyrazinato]iridium(III) (abbreviation: [Ir(dmpoppr)₃]). A structure of [Ir(dmpoppr)₃] is illustrated below.

[Chemical formula 56]

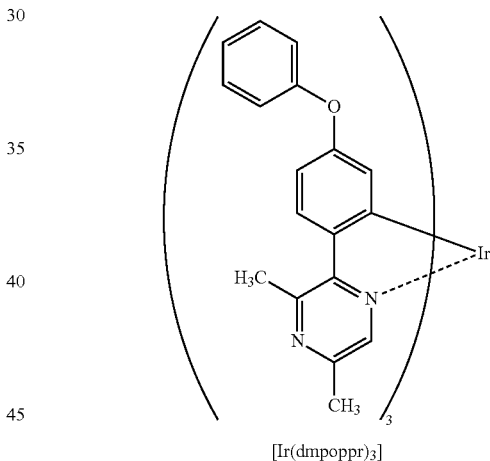

[Ir(dmpoppr)₃]

Synthesis of Tris[3,5-dimethyl-2-(4-phenoxyphenyl)pyrazinato]iridium(III) (abbreviation: [Irdmpoppr)₃])]

First, 1.42 g of the ligand prepared in Step 1 in Synthesis Example 1 above, Hdmpoppr, and 0.50 g of tris(acetylacetonato)iridium(III) were placed into a reaction container provided with a three-way cock, and the air in the reaction container was replaced with argon. After that, the mixture was heated at 250° C. for 43 hours to be reacted. The reactant was dissolved in dichloromethane, and this solution was filtered. After the solvent of the filtrate was distilled and the obtained residue was washed with ethyl acetate and then with methanol, recrystallization from dichloromethane gave the organometallic complex which is one embodiment of the present invention, [Ir(dmpoppr)₃] (an orange powder in a yield of 22%). The synthesis scheme is illustrated in the following formulae (f).

[Chemical formulae 57]

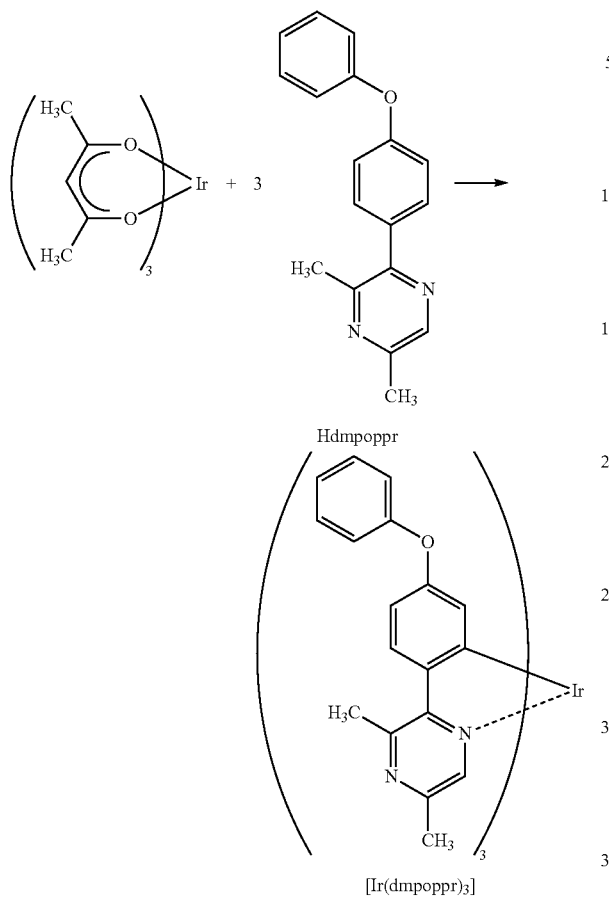

[Ir(dmpoppr)₃]

Figure 12:
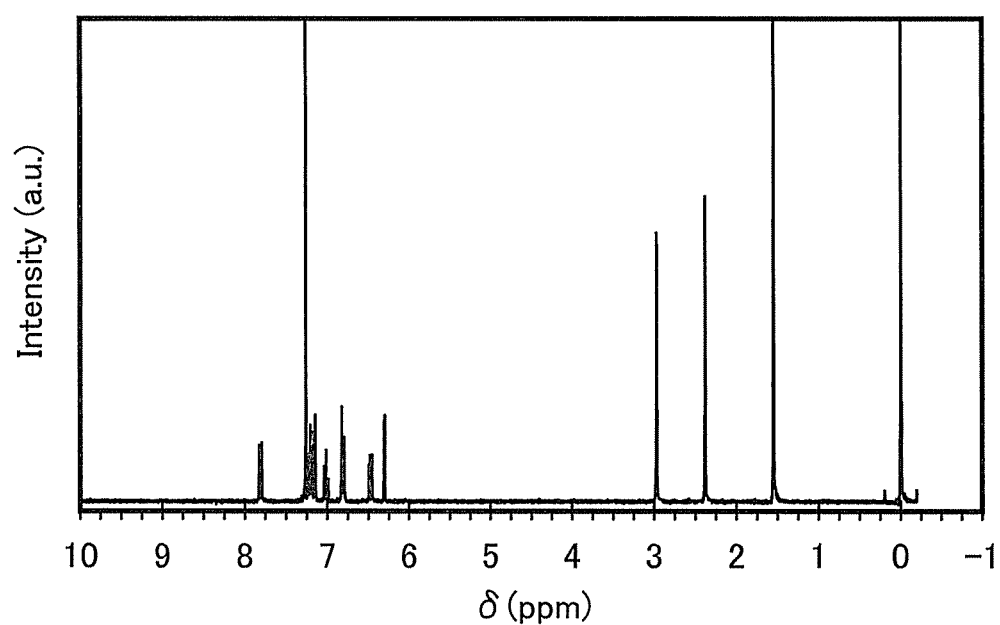
FIG. 12 shows a $^1$H NMR chart of an organometallic complex represented by a structural formula (130).

The results of the nuclear magnetic resonance (¹H NMR) spectroscopy, by which the orange powder obtained above was analyzed, are shown below. In addition, a ¹H-NMR chart is shown in FIG. 12. These results revealed that the organometallic complex represented by the above-described structural formula (130) which is one embodiment of the present invention, [Ir(dmpoppr)₃], was obtained in Synthesis Example 2.

$^1$H NMR. δ (CDCl$_3$): 2.38 (s, 9H), 2.97 (s, 9H), 6.31 (d, 3H), 6.47 (dd, 3H), 6.82 (d, 6H), 7.02 (t, 3H), 7.15 (s, 3H), 7.21 (t, 6H), 7.81 (d, 3H).

Figure 13:
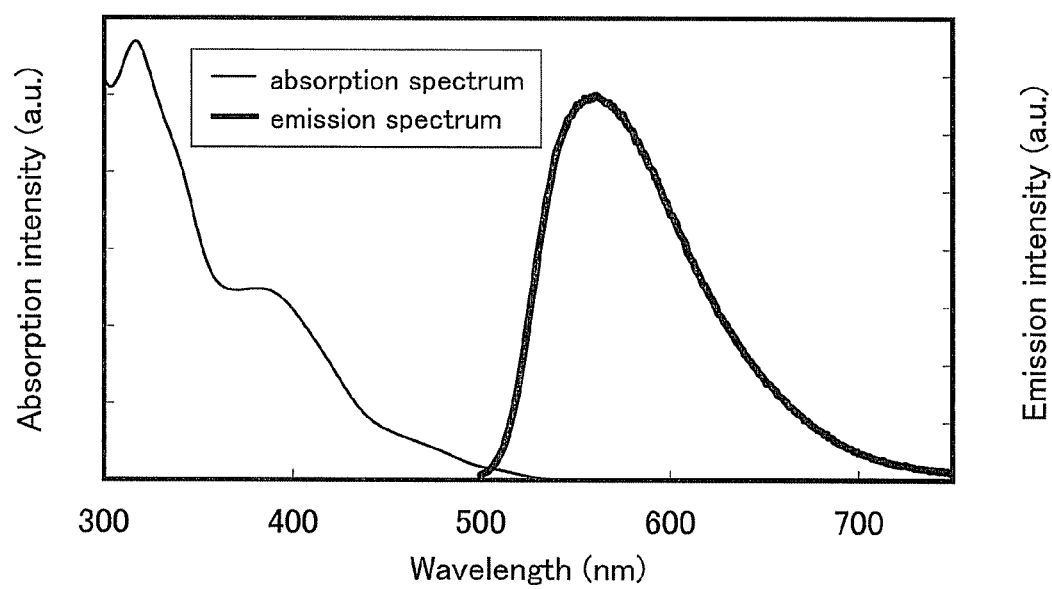
FIG. 13 shows an ultraviolet-visible absorption and emission spectra of an organometallic complex represented by a structural formula (130).

Next, an ultraviolet-visible absorption spectrum (hereinafter, simply referred to as an "absorption spectrum") of a dichloromethane solution of [Ir(dmpoppr)₃] and an emission spectrum thereof were measured. The measurement of the absorption spectrum was conducted at room temperature, for which an ultraviolet-visible light spectrophotometer (V550 type manufactured by Japan Spectroscopy Corporation) was used and the dichloromethane solution (0.083 mmol/L) was put in a quartz cell. In addition, the measurement of the emission spectrum was conducted at room temperature, for which a fluorescence spectrophotometer (FS920 manufactured by Hamamatsu Photonics Corporation) was used and the degassed dichloromethane solution (0.50 mmol/L) was put in a quartz cell. Measurement results of the obtained absorption and emission spectra are shown in FIG. 13, in which the horizontal axis represents wavelength and the vertical axis represents absorption intensity and emission intensity. In FIG. 13 where there are two solid lines, the thin line represents the absorption spectrum and the thick line represents the emission spectrum. Note that the absorption spectrum in FIG. 13 is the results obtained in such a way that the absorption spectrum measured by putting only dichloromethane in a quartz cell was subtracted from the absorption spectrum measured by putting the dichloromethane solution (0.083 mmol/L) in a quartz cell.

As shown in FIG. 13, the organometallic complex of one embodiment of the present invention, [Ir(dmpoppr)₃], has an emission peak at 561 nm, and yellow light emission was observed from the dichloromethane solution.

EXAMPLE 3

Figure 14:
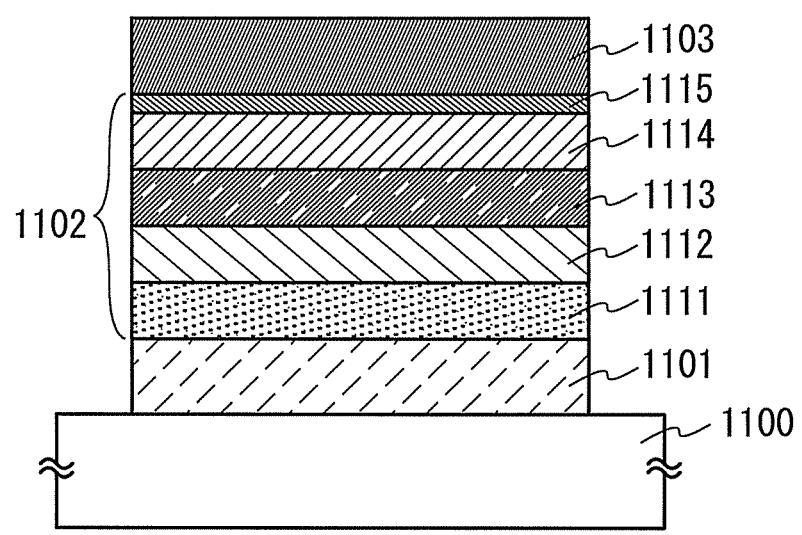
FIG. 14 illustrates a light-emitting element which is one embodiment of the present invention.

This example shows a light-emitting element (a light-emitting element 1) in which the organometallic complex that is one embodiment of the present invention and was synthesized in Example 1, [Ir(dmpoppr)₂(acac)] (structural formula (100)), is included as a light-emitting substance, and a light-emitting element (a light-emitting element 2) in which the organometallic complex that is one embodiment of the present invention and was synthesized in Example 2, [Ir(dmpoppr)₃] (structural formula (130)), is included as a light-emitting substance. Note that structures of other organic compounds used in this example are represented by structural formulae (i) to (iv) below. In addition, element structures of the light-emitting elements will be described on the basis of FIG. 14.

[Chemical formulae 58]

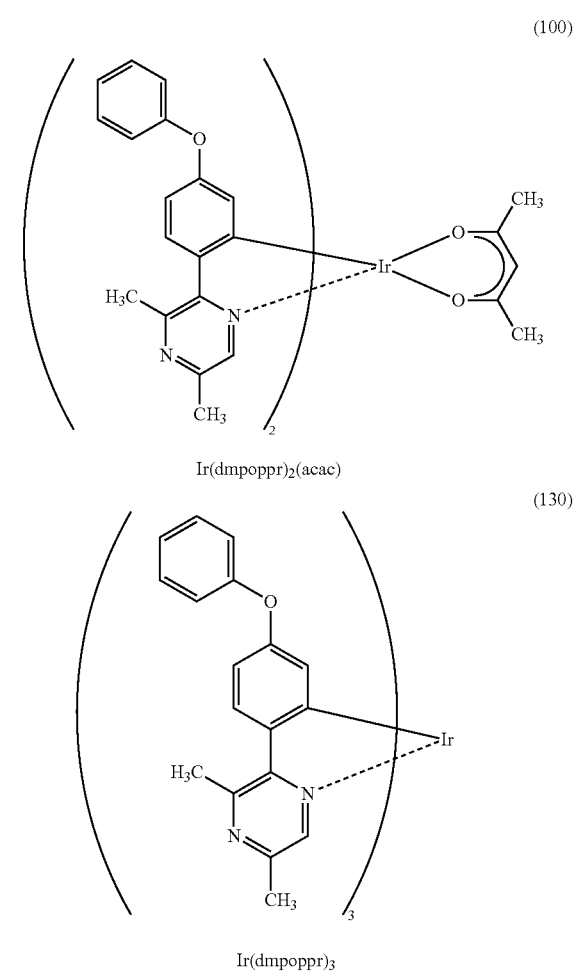

Ir(dmpoppr)₂(acac)

Ir(dmpoppr)₃

-continued (i)

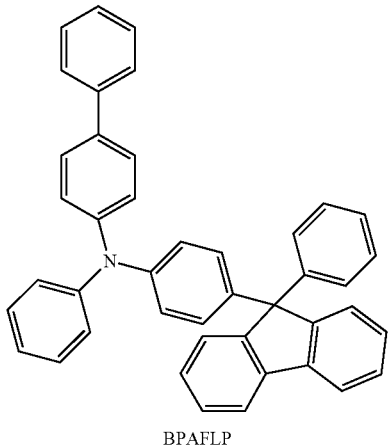

BPAFLP (ii)

2mDBTPDBq-II (iii)

PCBNBB

-continued (iv)

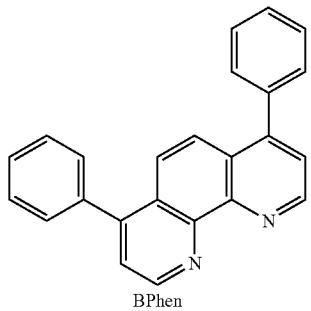

BPhen (Fabrication of Light-Emitting Element 1 and Light-Emitting Element 2)

First, as a first electrode 1101, a 110 nm thick film of indium tin oxide containing silicon oxide (ITSO) is formed over a substrate 1100 made of glass. Note that a surface of the ITSO film is covered with an insulating film so that a 2 mm square portion of the surface is exposed. Here, the first electrode 1101 is an electrode that functions as an anode of light-emitting elements (light-emitting elements 1 and 2).

Next, in pretreatment for forming the light-emitting elements over the substrate 1100, a surface of the substrate was washed with ozone water, baking was performed at 200° C. for one hour, and UV ozone treatment was then performed for 370 seconds.

After that, the substrate was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 was fixed to a holder provided in the vacuum evaporation apparatus so that the surface of the substrate on which the first electrode 1101 was formed faced downward. In the case described in this example, a hole-injection layer 1111, a hole-transport layer 1112, a light-emitting layer 1113, an electron-transport layer 1114, and an electron-injection layer 1115 which are included in an EL layer 1102 are sequentially formed.

After the pressure in the vacuum evaporation apparatus was reduced to $10^{-4}$ Pa, 4-phenyl-4'-(9-phenylfluoren-9-yl)triphenylamine (abbreviation: BPAFLP) represented by the above structural formula (i) and molybdenum oxide were co-evaporated so that the mass ratio of BPAFLP to molybdenum oxide was 4:2; thus, the hole-injection layer 1111 was formed. The thickness thereof was set to 40 nm. Note that co-evaporation is an evaporation method in which a plurality of different substances is concurrently vaporized from respective different evaporation sources.

Next, BPAFLP was evaporated to a thickness of 20 nm, so that the hole-transport layer 1112 was formed.

Next, for the light-emitting element 1, the light-emitting layer 1113 was formed by co-evaporation of 2-[3-(dibenzothiophen-4-yl)phenyl]dibenzo[f,h]quinoxaline (abbreviation: 2mDBTPDBq-II) represented by the above structural formula (ii), 4,4'-di(1-naphthyl)-4''-(9-phenyl-9H-carbazol-3-yl)triphenylamine (abbreviation: PCBNBB) represented by the above structural formula (iii), and (acetylacetonato)bis[2-(4-tert-butylphenyl)-3,5-diphenylpyrazinato)iridium(III) (abbreviation: [Ir(dmpoppr)$_2$(acac)]) represented by the above structural formula (100) on the hole-transport layer 1112 so that the mass ratio of 2mDBTPDBq-II to PCBNBB and [Ir(dmpoppr)$_2$(acac)] were 0.8:0.2:0.05. For the light-emitting element 2, the light-emitting layer 1113 was formed by co-evaporation of 2mDBTPDBq-II, PCBNBB, and tris[3,5-dimethyl-2-(4-phenoxyphenyl)pyrazinato]iridium(III) (abbreviation: [Ir(dmpoppr)$_3$]) represented by the above structural formula (130) on the hole-transport layer 1112 so that the mass ratio of 2mDBTPDBq-II to PCBNBB and [Ir(dmpoppr)$_3$] were 0.8:0.2:0.05. The thickness of the light-emitting layer in each of the light-emitting elements 1 and 2 was set to 40 nm.

Next, 2mDBTPDBq-II was evaporated to a thickness of 10 nm and then bathophenanthroline (abbreviation: BPhen) represented by the above structural formula (iv) was evaporated to a thickness of 20 nm, so that the electron-transport layer 1114 was formed. Furthermore, lithium fluoride was evaporated to a thickness of 2 nm on the electron-transport layer 1114, so that the electron-injection layer 1115 was formed.

Next, an aluminum film was formed to a thickness of 200 nm to form the second electrode 1103. Thus, the light-emitting elements (light-emitting elements 1 and 2) which are embodiments of the present invention were obtained. Note that the second electrode 1103 is an electrode that functions as a cathode. Note that in the above evaporation processes, evaporation was all performed by a resistance heating method.

Further, these light-emitting elements were sealed in a glove box under a nitrogen atmosphere to prevent from being exposed to the air.

[Operation Characteristics of Light-Emitting Element 1 and Light-Emitting Element 2]

Operation characteristics of the fabricated light-emitting elements (light-emitting elements 1 and 2) were measured. Note that the measurements were carried out at room temperature (in an atmosphere kept at 25° C.).

Figure 15:
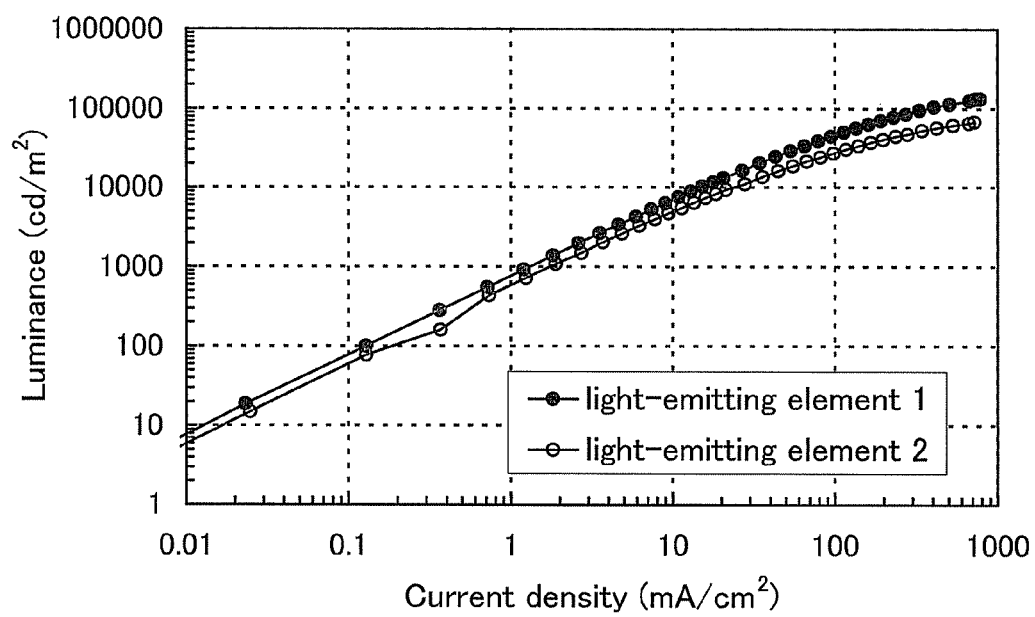
FIG. 15 shows luminance versus current density characteristics of light-emitting elements which are embodiments of the present invention.
Figure 16:
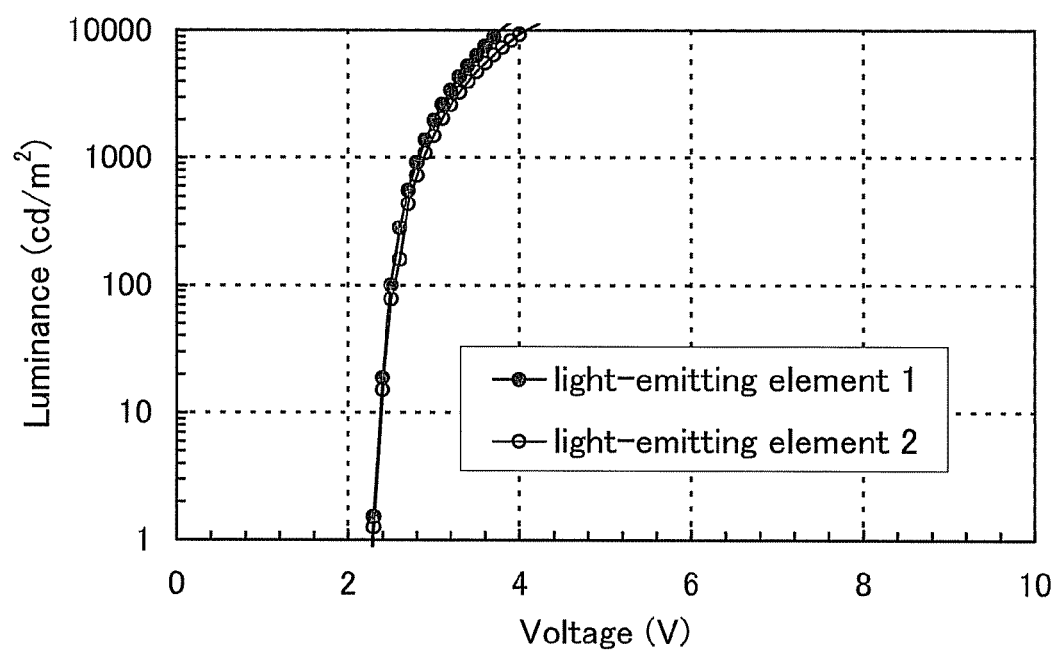
FIG. 16 shows luminance versus voltage characteristics of light-emitting elements which are embodiments of the present invention.

FIG. 15 shows luminance versus current density characteristics of the light-emitting elements. In FIG. 15, the vertical axis represents luminance (cd/m$^2$) and the horizontal axis represents current density (mA/cm$^2$). FIG. 16 shows luminance versus voltage characteristics of the light-emitting elements. In FIG. 16, the vertical axis represents luminance (cd/m$^2$) and the horizontal axis represents voltage (V). It can be confirmed from FIG. 15 and FIG. 16 that the light-emitting elements 1 and 2 each have high emission efficiency.

Figure 17:
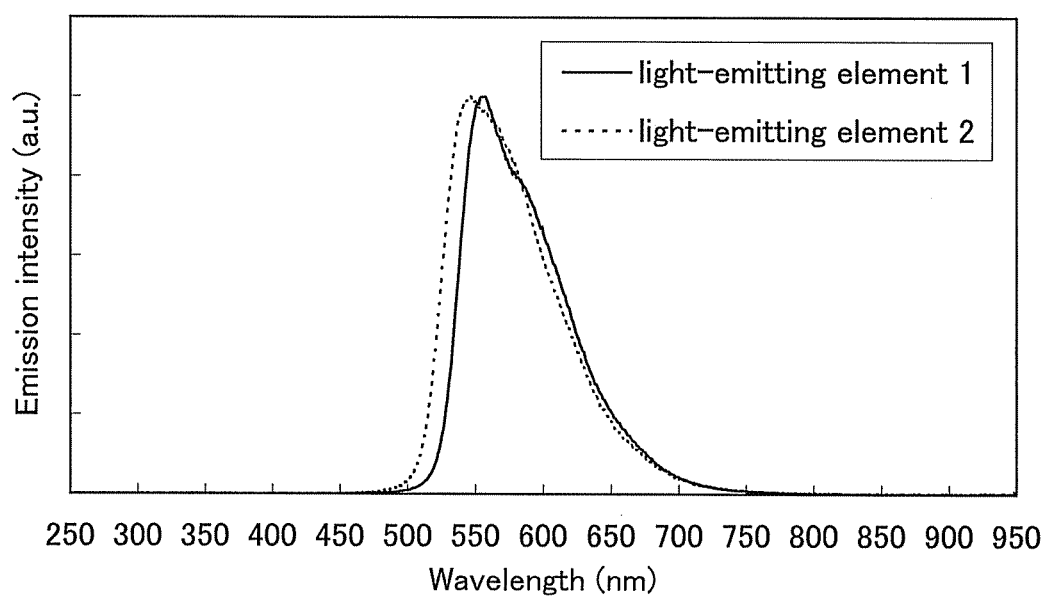
FIG. 17 shows emission spectra of light-emitting elements which are embodiments of the present invention.

FIG. 17 shows emission spectra obtained when current was supplied to the light-emitting elements at a current density of 25 mA/cm$^2$. The emission spectrum of the light-emitting element 1 has a peak at 556 nm as shown in FIG. 17, which indicates derivation from light emission of one of the organometallic complexes which are embodiments of the present invention ([Ir(dmpoppr)$_2$(acac)]). Further, the emission spectrum of the light-emitting element 2 has a peak at 546 nm, which indicates derivation from light emission of one of the organometallic complexes which are embodiments of the present invention [Ir(dmpoppr)$_3$]).

Reference Example 1

A method of synthesizing 4-phenyl-4'-(9-phenylfluoren-9-yl)triphenylamine (abbreviation: BPAFLP) used in the above Example will be specifically described. A structure of BPAFLP is illustrated below.

[Chemical formula 59]

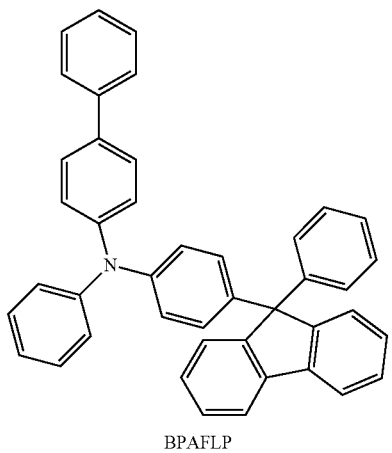

BPAFLP

Step 1: Method of Synthesizing
9-(4-Bromophenyl)-9-phenylfluorene

In a 100 mL three-neck flask, 1.2 g (50 mmol) of magnesium was heated and stirred for 30 minutes under reduced pressure to be activated. The activated magnesium was cooled to room temperature, and the flask was made to contain a nitrogen atmosphere. Then, several drops of dibromoethane were added, so that foam formation and heat generation were confirmed. After 12 g (50 mmol) of 2-bromobiphenyl dissolved in 10 mL of diethyl ether was slowly added dropwise to this mixture, the mixture was heated and stirred under reflux for 2.5 hours, so that a Grignard reagent was prepared.

Into a 500 mL three-neck flask were placed 10 g (40 mmol) of 4-bromobenzophenone and 100 mL of diethyl ether. After the Grignard reagent which was synthesized in advance was slowly added dropwise to this mixture, the mixture was heated and stirred under reflux for 9 hours.

After reaction, this mixture solution was filtered to give a residue. The obtained residue was dissolved in 150 mL of ethyl acetate, a 1N-hydrochloric acid solution was added thereto until the mixed solution became acid, and the mixture was stirred for 2 hours. The organic layer portion of this liquid was washed with water, and magnesium sulfate was added to remove moisture. This suspension was filtered, and the obtained filtrate was concentrated to give an oily substance.

Into a 500 mL recovery flask were placed this oily substance, 50 mL of glacial acetic acid, and 1.0 mL of hydrochloric acid. The mixture was stirred and heated at 130° C. for 1.5 hours under a nitrogen atmosphere to be reacted.

After the reaction, this reaction mixture solution was filtered to give a residue. The obtained residue was washed with water, an aqueous sodium hydroxide solution, water, and methanol in this order. Then, the mixture was dried, so that the substance which was the object of the synthesis was obtained as 11 g of a white powder in 69% yield. A reaction scheme of the above synthesis method is illustrated in the following formulae (x).

[Chemical formulae 60]

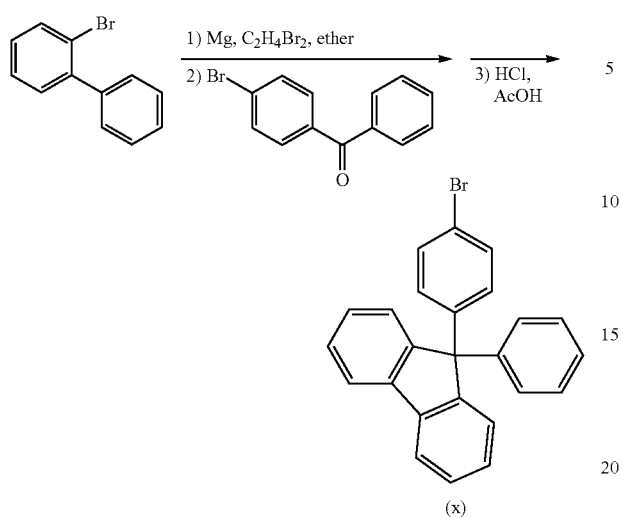

(x)

Step 2: Method of Synthesizing 4-Phenyl-4'-(9-phenylfluoren-9-yl)triphenylamine (abbreviation: BPAFLP)

Into a 100 mL three-neck flask were placed 3.2 g (8.0 mmol) of 9-(4-bromophenyl)-9-phenylfluorene, 2.0 g (8.0 mmol) of 4-phenyl-diphenylamine, 1.0 g (10 mmol) of sodium tert-butoxide, and 23 mg (0.04 mmol) of bis(dibenzylideneacetone)palladium(0), and the air in the flask was replaced with nitrogen. Then, 20 mL of dehydrated xylene was added to this mixture. After the mixture was degassed by being stirred under reduced pressure, 0.2 mL (0.1 mmol) of tri(tert-butyl)phosphine (a 10 wt % hexane solution) was added to the mixture. This mixture was stirred and heated at 110° C. for 2 hours under a nitrogen atmosphere to be reacted.

After the reaction, 200 mL of toluene was added to this reaction mixture, and this suspension was filtered through Florisil (produced by Wako Pure Chemical Industries, Ltd., Catalog No. 540-00135) and Celite (produced by Wako Pure Chemical Industries, Ltd., Catalog No. 531-16855). The obtained filtrate was concentrated, and the resulting substance was purified by silica gel column chromatography (a developing solvent, toluene:hexane=1:4). The obtained fraction was concentrated, and acetone and methanol were added to the mixture. The mixture was irradiated with ultrasonic waves and then recrystallized, so that the substance which was the object of the synthesis was obtained as 4.1 g of a white powder in 92% yield. A reaction scheme of the above synthesis method is illustrated in the following formulae (x').

[Chemical formulae 61]

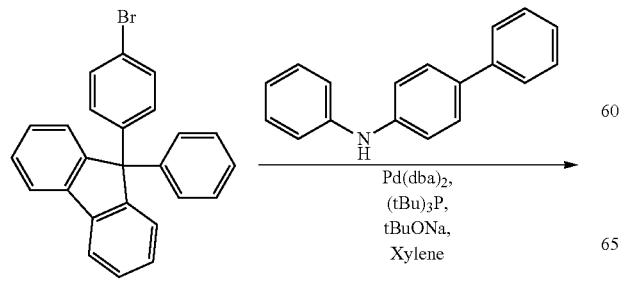

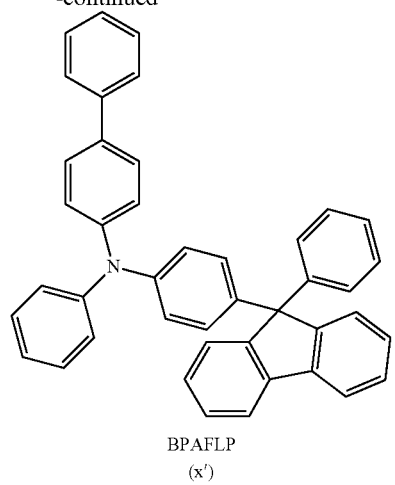

BPAFLP
(x')

The Rf values of the substance that was the object of the synthesis, 9-(4-bromophenyl)-9-phenylfluorene, and 4-phenyl-diphenylamine were respectively 0.41, 0.51, and 0.27, which were found by silica gel thin layer chromatography (TLC) (a developing solvent, ethyl acetate:hexane=1:10).

The compound obtained in Step 2 above was identified as 4-phenyl-4'-(9-phenylfluoren-9-yl)triphenylamine (abbreviation: BPAFLP), which was the object of the synthesis, by nuclear magnetic resonance (NMR) spectroscopy. $^1$H NMR data of the obtained substance are as follows.

$^1$H NMR (CDCl$_3$, 300 MHz): δ (ppm)=6.63-7.02 (m, 3H), 7.06-7.11 (m, 6H), 7.19-7.45 (m, 18H), 7.53-7.55 (m, 2H), 7.75 (d, J=6.9, 2H).

Reference Example 2

A method of synthesizing 2-[3-(dibenzothiophen-4-yl)phenyl]dibenzo[f,h]quinoxaline (abbreviation: 2mDBTP-DBq-II) used in the above example will be specifically described. A structure of 2mDBTPDBq-II is illustrated below.

[Chemical formula 62]

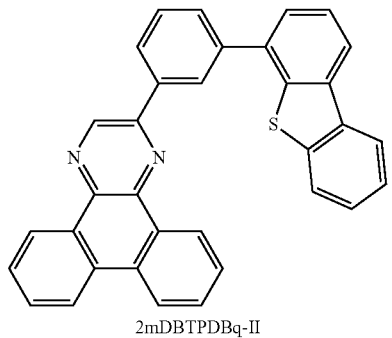

2mDBTPDBq-II

Synthesis of 2-[3-(Dibenzothiophen-4-yl)phenyl]dibenzo[f,h]quinoxaline (abbreviation: 2mDBTP-DBq-II)

A synthesis scheme of 2-[3-(dibenzothiophen-4-yl)phenyl]dibenzo[f,h]quinoxaline (abbreviation: 2mDBTPDBq-II) is illustrated in the following formulae (y).

[Chemical formulae 63]

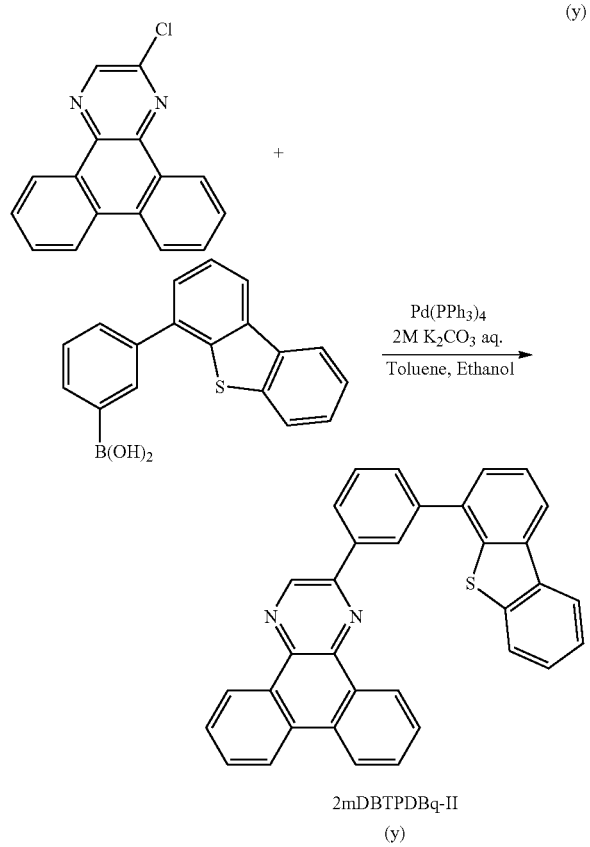

In a 2 L three-neck flask were placed 5.3 g (20 mmol) of 2-chlorodibenzo[f,h]quinoxaline, 6.1 g (20 mmol) of 3-(dibenzothiophen-4-yl)phenylboronic acid, 460 mg (0.4 mmol) of tetrakis(triphenylphosphine)palladium(0), 300 mL of toluene, 20 mL of ethanol, and 20 mL of a 2M potassium carbonate aqueous solution. This mixture was degassed by stirring under reduced pressure, and the air in the flask was replaced with nitrogen. This mixture was stirred under a nitrogen stream at 100° C. for 7.5 hours. After cooled to room temperature, the obtained mixture was filtered to give a white residue. The obtained residue was washed well with water and ethanol in this order, and then dried. The obtained solid was dissolved in about 600 mL of hot toluene, and the mixture was suction filtered through Celite and Florisil, so that a clear colorless filtrate was obtained. The obtained filtrate was concentrated and purified by silica gel column chromatography using about 700 mL of silica gel. The chromatography was carried out using toluene at a temperature of about 40° C. as a developing solvent. Acetone and ethanol were added to the solid obtained here and subjected to irradiation with ultrasonic waves. Then, the generated suspended solid was filtered and the obtained solid was dried, so that the object of the synthesis was obtained as 7.85 g of a white powder in a yield of 80%.

The above object of the synthesis was relatively soluble in hot toluene, but is a material that is easy to precipitate when cooled. Further, the substance was poorly soluble in other organic solvents such as acetone and ethanol. Hence, the utilization of these different degrees of solubility leads to a high-yield synthesis with a simple method as above. Specifically, after the reaction finished, the mixture was returned to room temperature and the precipitated solid was collected by filtration, so that most impurities were able to be easily removed. Further, by hot column chromatography with hot toluene as a developing solvent, even the object of the synthesis which is easy to precipitate was able to be readily purified.

By a train sublimation method, 4.0 g of the obtained white powder was purified in such a way that the white powder was heated at 300° C. under a pressure of 5.0 Pa with a flow rate of argon gas of 5 mL/min. After the sublimation, the object of the synthesis was obtained in a yield of 88% as 3.5 g of white powder in solid form and in fiber form, which was attached to a portion at about 230° C. to 240° C. in a reaction tube of a sublimation apparatus.

Nuclear magnetic resonance (NMR) spectroscopy identified this compound as 2-[3-(dibenzothiophen-4-yl)phenyl]dibenzo[f,h]quinoxaline (abbreviation: 2mDBTPDBq-II), which was the object of the synthesis. $^1$H NMR data of the obtained substance are shown below.

$^1$H NMR (CDCl$_3$, 300 MHz): δ (ppm)=7.45-7.52 (m, 2H), 7.59-7.65 (m, 2H), 7.71-7.91 (m, 7H), 8.20-8.25 (m, 2H), 8.41 (d, J=7.8 Hz, 1H), 8.65 (d, J=7.5 Hz, 2H), 8.77-8.78 (m, 1H), 9.23 (dd, J=7.2 Hz, 1.5 Hz, 1H), 9.42 (dd, J=7.8 Hz, 1.5 Hz, 1H), 9.48 (s, 1H).

This application is based on Japanese Patent Application serial No. 2010-233014 filed with the Japan Patent Office on Oct. 15, 2010, the entire contents of which are hereby incorporated by reference.

What is claimed is:

1. An organometallic complex represented by a formula (G6),

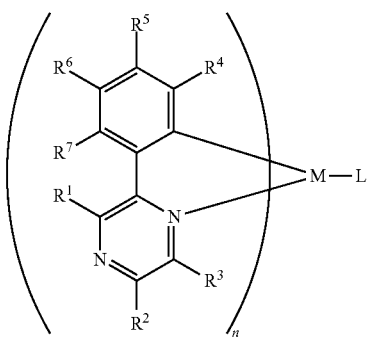

(G6)

wherein:

$R^1$ represents an alkyl group having 1 to 4 carbon atoms, an alkoxy group having 1 to 4 carbon atoms, an alkoxycarbonyl group having 1 to 5 carbon atoms, or a phenyl group;

$R^2$ and $R^3$ separately represent hydrogen, an alkyl group having 1 to 4 carbon atoms, or a phenyl group;

$R^4$, $R^5$, $R^6$, and $R^7$ separately represent hydrogen, an alkyl group having 1 to 4 carbon atoms, an alkoxy group having 1 to 4 carbon atoms, halogen, a trifluoromethyl group, and a phenyl group;

at least one of $R^4$, $R^5$, $R^6$, and $R^7$ has a structure represented by a formula (G2):

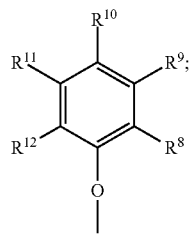
(G2)

M represents a Group 9 element or a Group 10 element;
L represents a monoanionic ligand;
n is 2 when M is a Group 9 element or 1 when M is a Group 10 element; and
$R^8$, $R^9$, $R^{10}$, $R^{11}$, , $R^{12}$ and separately represent hydrogen, an alkyl group having 1 to 4 carbon atoms, an alkoxy group having 1 to 4 carbon atoms, halogen, a trifluoromethyl group, or a phenyl group.

2. The organometallic complex according to claim 1, wherein the monoanionic ligand is a monoanionic bidentate chelate ligand having a β-diketone structure, a monoanionic bidentate chelate ligand having a carboxyl group, a monoanionic bidentate chelate ligand having a phenolic hydroxyl group, or a monoanionic bidentate chelate ligand in which two ligand elements are both nitrogen.

3. The organometallic complex according to claim 1, wherein the monoanionic ligand is a ligand selected from the group of consisting of structural formulae (L1) to (L6):

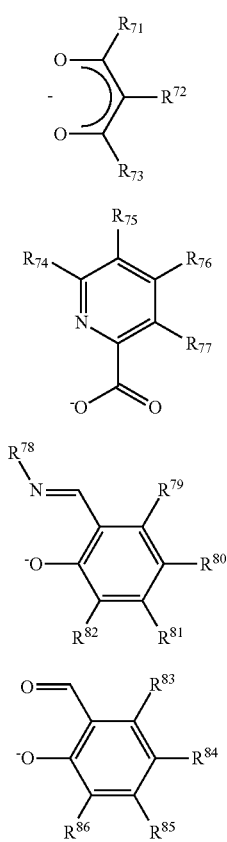

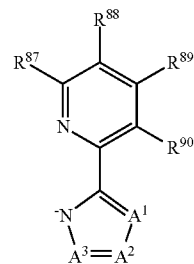
(L5)

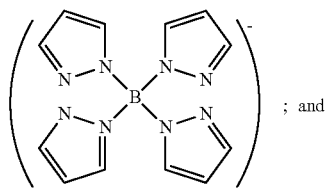
(L6)

; and wherein:
$R^{71}$ to $R^{90}$ separately represent hydrogen, an alkyl group having 1 to 4 carbon atoms, halogen, a haloalkyl group, an alkoxy group having 1 to 4 carbon atoms, an alkylthio group having 1 to 4 carbon atoms, or a phenyl group;
$A^1$, $A^2$, and $A^3$ separately represent nitrogen or C—R; and
R represents hydrogen, an alkyl group having 1 to 4 carbon atoms, halogen, a haloalkyl group having 1 to 4 carbon atoms, or a phenyl group.

4. The organometallic complex according to claim 1, wherein $R^3$ represents hydrogen.

5. The organometallic complex according to claim 1, wherein $R^5$ is a substituent represented by the formula (G2).

6. The organometallic complex according to claim 1, wherein M is iridium or platinum.

7. An organometallic complex represented by a formula (G8),

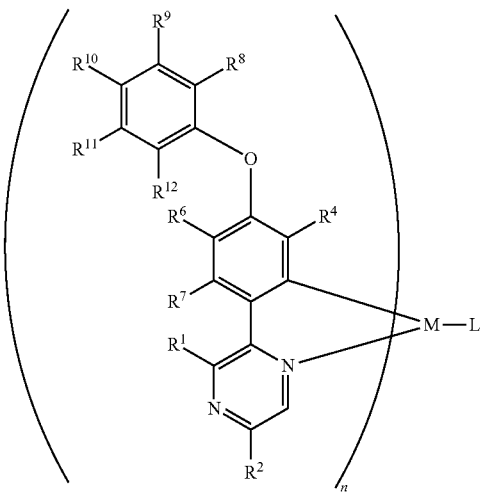
(G8)

wherein:
$R^1$ represents an alkyl group having 1 to 4 carbon atoms, an alkoxy group having 1 to 4 carbon atoms, an alkoxycarbonyl group having 1 to 5 carbon atoms, or a phenyl group;
$R^2$ represents hydrogen, an alkyl group having 1 to 4 carbon atoms, or a phenyl group;
$R^4$, $R^6$, and $R^7$ separately represent hydrogen, an alkyl group having 1 to 4 carbon atoms, an alkoxy group having 1 to 4 carbon atoms, halogen, a trifluoromethyl group, or a phenyl group;

$R^8$, $R^9$, $R^{10}$, $R^{11}$, and $R^{12}$ separately represent hydrogen, an alkyl group having 1 to 4 carbon atoms, an alkoxy group having 1 to 4 carbon atoms, halogen, a trifluoromethyl group, or a phenyl group;

M represents a Group 9 element or a Group 10 element;

L represents a monoanionic ligand; and n is 2 when M is a Group 9 element or 1 when M is a Group 10 element.

8. The organometallic complex according to claim 7, wherein the monoanionic ligand is a monoanionic bidentate chelate ligand having a β-diketone structure, a monoanionic bidentate chelate ligand having a carboxyl group, a monoanionic bidentate chelate ligand having a phenolic hydroxyl group, or a monoanionic bidentate chelate ligand in which two ligand elements are both nitrogen.

9. The organometallic complex according to claim 7, wherein the monoanionic ligand is a ligand selected from the group of consisting of structural formulae (L1) to (L6):

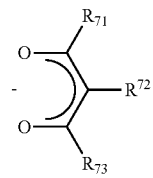

(L1)

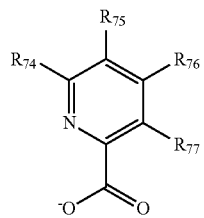

(L2)

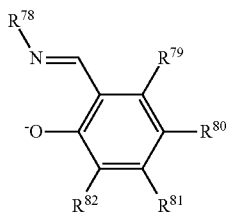

(L3)

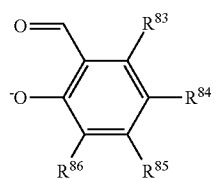

(L4)

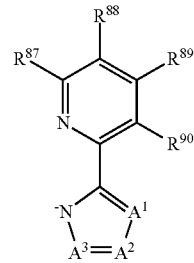

(L5)

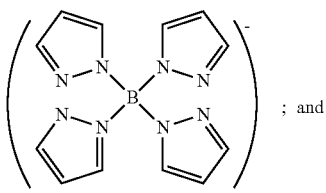

; and (L6)

wherein:

$R^{71}$ to $R^{90}$ separately represent hydrogen, an alkyl group having 1 to 4 carbon atoms, halogen, a haloalkyl group, an alkoxy group having 1 to 4 carbon atoms, an alkylthio group having 1 to 4 carbon atoms, or a phenyl group;

$A^1$, $A^2$, and $A^3$ separately represent nitrogen or C—R; and

R represents hydrogen, an alkyl group having 1 to 4 carbon atoms, halogen, a haloalkyl group having 1 to 4 carbon atoms, or a phenyl group.

10. The organometallic complex according to claim 7, wherein $R^4$, $R^6$, and $R^7$ separately represent hydrogen.

11. The organometallic complex according to claim 7, wherein M is iridium or platinum.

* * * * *

UNITED STATES PATENT AND TRADEMARK OFFICE
CERTIFICATE OF CORRECTION

PATENT NO. : 8,664,383 B2  Page 1 of 1
APPLICATION NO. : 13/242311
DATED : March 4, 2014
INVENTOR(S) : Hideko Inoue et al.

It is certified that error appears in the above-identified patent and that said Letters Patent is hereby corrected as shown below:

In the Specification:

Column 11, Line 36; Change "the allyl group." to --the alkyl group.--.

Column 47, Line 9; Change "and NPS," to --and NPB,--.

Column 51, Line 66; Change "such as NPS, TPD," to --such as NPB, TPD,--.

Column 56, Line 59; Change "foamed" to --formed--.

In the Claims:

Column 77, Line 17, Claim 1; Change "$R^8$, $R^9$, $R^{10}$, $R^{11}$, , $R^{12}$ and separately" to --$R^8$, $R^9$, $R^{10}$, $R^{11}$, and $R^{12}$ separately--.

Column 78, Line 22, Claim 3; Change "$R^{71}$ to $R^{90}$ separately" to --$R^{71}$ to $R^{90}$ separately--.

Column 80, Line 31, Claim 9; Change "$R^{71}$ to $R^{90}$ separately" to --$R^{71}$ to $R^{90}$ separately--.

Signed and Sealed this
Twenty-fourth Day of June, 2014

Michelle K. Lee
*Deputy Director of the United States Patent and Trademark Office*